United States Patent [19]

Cheng et al.

[11] Patent Number: 5,770,565

[45] Date of Patent: Jun. 23, 1998

[54] PEPTIDES FOR REDUCING OR INHIBITING BONE RESORPTION

[75] Inventors: Soan Cheng, San Diego; Ronald Ingram, Oceanside; Daniel Mullen; Juerg Tschopp, both of San Diego, all of Calif.

[73] Assignee: La Jolla Cancer Research Center, La Jolla, Calif.

[21] Appl. No.: 303,052

[22] Filed: Sep. 8, 1994

Related U.S. Application Data

[63] Continuation-in-part of Ser. No. 227,316, Apr. 13, 1994, abandoned.

[51] Int. Cl.[6] .......................... A61K 38/08; A61K 38/10; C07K 7/06; C07K 7/08
[52] U.S. Cl. ................................. 514/11; 514/12; 514/13; 514/14; 514/15; 514/16; 514/17; 530/324; 530/325; 530/326; 530/327; 530/328; 530/329
[58] Field of Search .................................... 514/9, 11, 12, 514/13, 14, 15, 16, 17; 530/317, 321, 324, 325, 326, 327, 328, 329

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,792,525 | 12/1988 | Ruoslahti et al. | 435/240.243 |
| 5,041,380 | 8/1991 | Ruoslahti et al. | 435/240.2 |
| 5,192,746 | 3/1993 | Lobl et al. | 514/11 |
| 5,227,469 | 7/1993 | Lazarus et al. | 530/324 |

FOREIGN PATENT DOCUMENTS

| | | | |
|---|---|---|---|
| 0425212 | 5/1991 | European Pat. Off. . | |
| 437 367 A2 | 7/1991 | European Pat. Off. | C07K 7/10 |
| 578083 | 1/1994 | European Pat. Off. | A16K 37/02 |
| 0618225 | 10/1994 | European Pat. Off. . | |
| WO89/05150 | 6/1989 | WIPO | A61K 37/02 |
| WO91/15515 | 10/1991 | WIPO | C07K 7/64 |
| WO 92/00995 | 1/1992 | WIPO . | |
| WO 95/0544 | 1/1995 | WIPO . | |
| WO 95/14714 | 6/1995 | WIPO . | |

OTHER PUBLICATIONS

Athanasou, N.A. et al., "Species Differences in the Immunophenotype of Osteoclasts and Mononuclear Phagocytes." Calcif. Tissue. Int. 50:427–432 (1992).

Reinholt, Finn P. et al., "Osteopontin –a Possible Anchor of Osteoclasts to Bone." Proc. Natl. Acad. Sci. USA. 87/4473–4475 (1990).

Van Dijk, Simon et al., "Evidence That a Non–RGD Domain in Rat Osteopontin is Involved in Cell Attachment." J. Bone and Mineral Res. 8:1499–1506 (1993).

Chenu, C. et al., "Cloning and Sequence Analysis of Bovine Bone Sialoprotein cDNA: Conservation of Acidic Domains, Tyrosine Sulfation Consensus Repeats, and RGD Cell Attachment Domain." J. Bone and Mineral Res. 9:417–421 (1994).

Denhardt, David T. and Guo, Xiaojia, "Osteopontin: A Protein with Diverse Functions." FASEB J. 7:1475–1482 (1993).

Nesbitt, Stephen et al., "Biochemical Characterization of Human Osteoclast Integrins." J. Biol. Chem. 268:16737–16745 (1993).

(List continued on next page.)

*Primary Examiner*—Jeffrey E. Russel
*Attorney, Agent, or Firm*—Campbell & Flores LLP

[57] ABSTRACT

The present invention provides Arg-Gly-Asp peptides that can reduce or inhibit the binding of osteoclasts to a matrix such as bone or can selectively alter integrin receptor binding. The invention also provides methods of using the Arg-Gly-Asp peptides to reduce or inhibit osteoclast binding to a matrix, to reduce or inhibit bone resorption in a subject and to alter $\alpha_v\beta_3$ binding.

38 Claims, 17 Drawing Sheets

OTHER PUBLICATIONS

Hughes, D.E. et al., "Integrin Expression in Human Bone." J. Bone & Mineral Res. 8:527–533 (1993).

Lakkakorpi, P.T. et al., "Vitronectin Receptor Has a Role in Bone Resorption but Does Not Mediate Tight Sealing Zone Attachment of Osteoclasts to the Bone Surface." J. Cell Biol. 115:1179–1186 (1991).

Ross, F. Patrick et al., "Interactions Between the Bone Matrix Proteins Osteopontin and Bone Sialoprotein and the Osteoclast Integrin $\alpha_v\beta$ Potentiate Bone Resorption." J. Biol. Chem. 268:9901–9907 (1993).

Chuntharapal, Anan et al., "Blocking Monoclonal Antibodies to $\alpha V\beta 3$ Integrin: A Unique Epitope of $\alpha V\beta 3$ Integrin is Present on Human Osteoclasts." Experimental Cell Res. 205:345–352 (1993).

Helfrich, Miep H. et al., "Rat Osteoclasts Adhere to a Wide Range of cf RGD (Arg–Gly–Asp) Peptide–Containing Proteins, Including the Bone Sialoproteins and Fibronectin, via a $\beta_3$ Integrin." J. Bone and Mineral Res. 7:335–343 (1992).

Miyauchi, Akimitsu et al., "Recognition of Osteopontin and Related Peptides by an $\alpha_v\beta_3$ Integrin Stimulates Immediate Cell Signals in Osteoclasts." J. Biol. Chem. 266:20369–20374 (1991).

Yamakawa, Kensuke et al., "An Arg–Gly–Asp Peptide Stimulates $Ca^{2+}$Efflux From Osteoclast Precursors Through a Novel Mechanism." American Physiological Society. 651–657 (1994).

Choi, Eric T. et al., "Inhibition of Neointimal Hyperplasia by Blocking $\alpha_v\beta_3$ Integrin with a Small Peptide Antagonist GpenGRGDSPCA." J. Vascular Surg. 19:125–134 (1994).

Flores, Myra E. et al., "RGD–Directed Attachment of Isolated Rat Osteoclasts to Osteopontin, Bone Sialoprotein, and Fibronectin." Experimental Cell Res. 201:526–530 (1992).

Mintz, Keith P. et al., "Purification and Fragmentation of Nondenatured Bone Sialoprotein: Evidence for a Cryptic, RGD–Resistant Cell Attachment Domain." J. Bone and Mineral Res. 8:985–995 (1993).

Horton, M.A. et al., "Arg–Gly–Asp (RGD) Peptides and the Anti–Vitronectin Receptor Antibody 23c6 Inhibit Dentine Resorption and Cell Spreading by Osteoclasts." Experimental Cell Res. 195:368–375 (1991).

Horton, Michael A. et al., "Modulation of Vitronectin Receptor–Mediated Osteoclast Adhesion by Arg–Gly–Asp Peptide Analogs: A Structure–Function Analysis." J. Bone and Mineral Res. 8:239–247 (1993).

Xie, Dong–lin and Homandberg, Gene A. "Fibronectin Fragments Bind to and Penetrate Cartilage Tissue Resulting in Proteinase Expression and Cartilage Damage." Biochimica et Biophysica Acta. 1182:189–196 (1993).

Fisher, John E. et al., "Inhibition of Osteoclastic Bone Resorption in Vivo by Echistatin, An Arginyl–glycyl–Aspartyl (RGD) –Containing Proteins." Endocrinology 132:1411–1413 (1993).

Sato, M. et al., "Echistatin is A Potent Inhibitor of Bone Resorption in Culture." J. Cell Biol. 111:1713–1723 (1990).

Macintyre, I. et al., "New Perspectives in Osteoporosis." 14:319–320 (1993).

Roudebush, Roger E. et al., "Effect of Weight Manipulation on Bone Loss Due to Ovariectomy and the Protective Effects of Estrogen in the Rat." CalcFied. Tissue Int. 53:61–64 (1993).

Williams, Janice A. et al., Dendrosapin: A Potent Integrin Receptor Inhibitor From the Venoms of Dendroapis viridis and D. jamesonii. Biochem. Soc. Transactions 21:73 (1992).

Gronowicz, Gloria A. and Derome, Mary E. "Synthetic Peptide Containing Arg–Gly–Asp Inhibits Bone Formation and Resorption in a Mineralizing Organ Culture System of Fetal Rat Parietal Bones." J. Bone and Mineral Res. 9:193–201 (1994).

Brooks, Peter C. et al., "Requirement of Vascular Integrin $\alpha_v\beta_3$ for Angiogenesis." Science 264:569–571 (1994).

Denis, Cecile et al., "Solid–Phase von Willebrand Factor Contains a Conformationally Active RGD Motif that Mediates Endothelial Cell Adhesion Through the $\alpha_v\beta_3$ Receptor." Blood 82:3622–3630 (1993).

Sato, Masahiko et al., "Structure–Activity Studies of the s–Echistatin Inhibition of Bone Resorption." J. Bone and Mineral Res. 9:1441–1449 (1994).

Young, Marian F. et al. "cDNA Cloning, mRNA Distribution and Heterogeneity, Chromosomal Location, and RFLP Analysis of Human Osteopontin (OPN)." Genomics 7:491–502 (1990).

Krchnak, Viktor et al. "[1–β–Mercaptopropionic Acid, 8–α, β–Diaminopropionic Acid] Vasopressin and [1–β–Mercaptopropionic Acid, 8–D–α,β–Diaminopropionic Acid] Vasopressin. Two Lysine–Vasopressin Analogs With Considerable Antidiuretic Effect." Collection Czechoslov. Chem. Commun. 44:2161–2164 (1979).

Bauer, Wilfried et al., "SMS201–995: A Very Potent and Selective Octapeptide Analogue of Somatostatin with Prolonged Action." Life Science 31:1133–1140 (1982).

Aumailley et al., "Arg–Gly–Asp Constrained within Cyclic Pentapeptides Strong and Selective Inhibitors of Cell Adhesion to Vitronectin and Laminin Fragment P1," FEBS Letters 291 (1) :50–54 (1991).

Fauchere et al., "Modulation of the Activity and Assessment of the Receptor Selectivity in a Series of New RGD–containing Peptides," Int'l J. Peptide & Protein Res. 42(5):440–444 (1993).

PCT Search Report (dated 9 Nov. 1995), International application No. PCT/US95/04741.

FIG. 1A
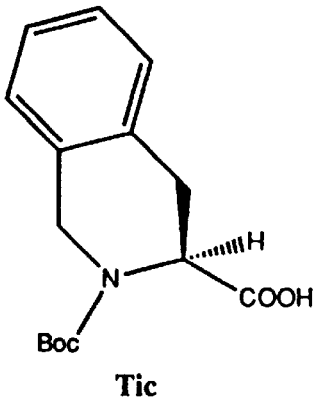
Tic
1,2,3,4-Tetrahydroisoquinoline-3-carboxylic acid
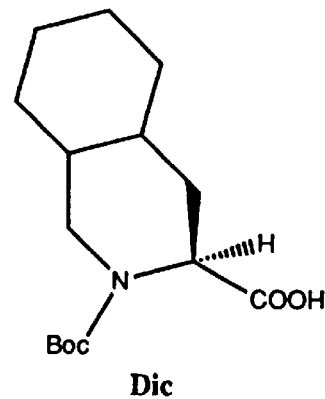
Dic
Decahydroisoquinoline-3-carboxylic acid
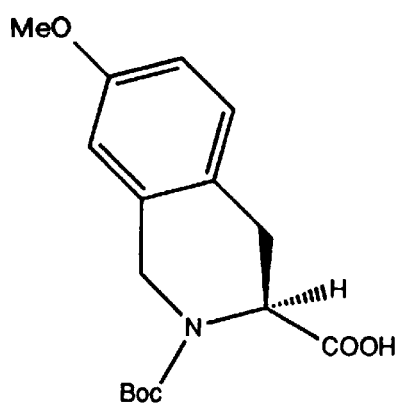
7-OMe-Tic
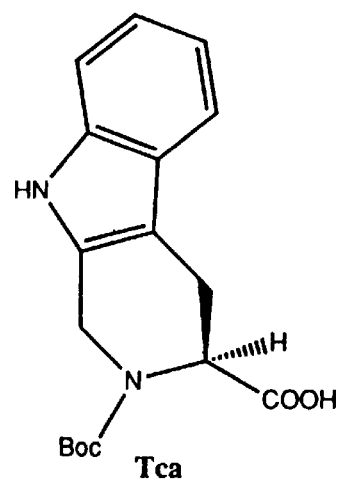
Tca
1,2,3,4,-Tetrahydro-β-carboline-3-carboxylic acid
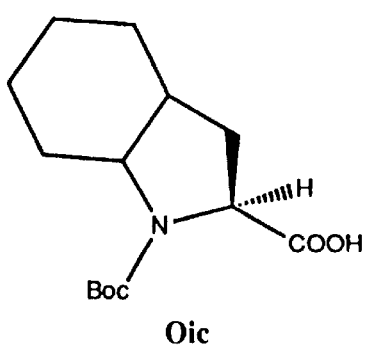
Oic
Octahydroindole-2-carboxylic acid
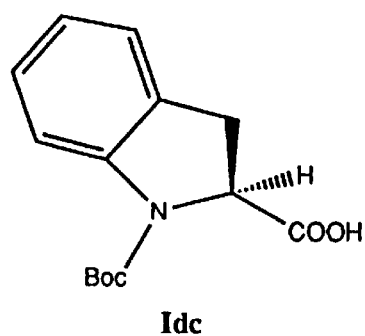
Idc
Indoline-2-carboxylic acid

FIG. 1B

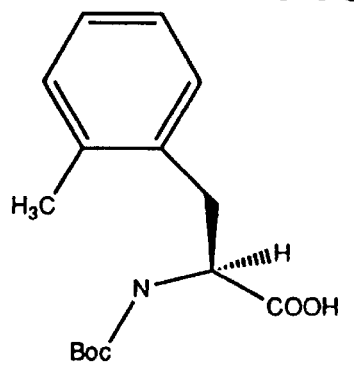

o-Methyl-phenylalanine

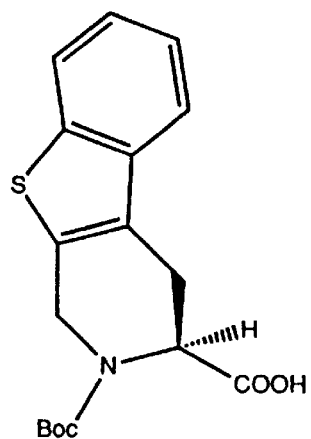

1,2,3,4-Tetrahydro[1]benzothieno[2,3-c]pyridine-3-carboxylic acid

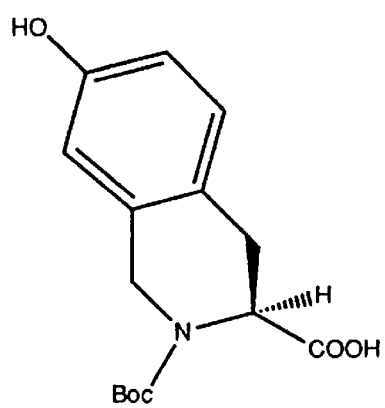

1,2,3,4-Tetrahydro-7-hydroxyisoquinoline-3-carboxylic acid

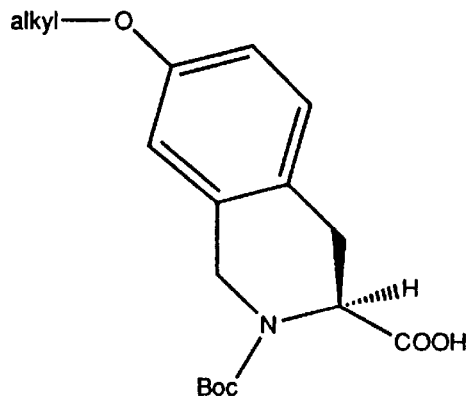

1,2,3,4-Tetrahydro-7-alkyloxy-isoquinoline-3-carboxylic acid

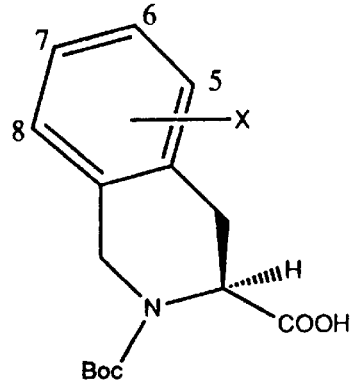

1,2,3,4-Tetrahydro-7-hydroxyisoquinoline-3-carboxylic acid derivatives wherein heteroatoms (X=F,Cl,Br,I) or alkyl (X=alkyl) groups are substituted at one of the following positions (5,6,7,8) or any combinations of positions.

Activity of Osteoporosis Peptides*

| Peptide | Sequence | chick OC detatch (FCS) | Chick nonOC (FCS) | Rat OC attach (FCS) | Rat Bone (Pits) | JY attach αvβ3/Vn | NRK attach (FCS) | Plate. Aggreg. (hep) | MG63 attach (FCS) | αvβ3 (Vn) | αvβ5 (Vn) | α5β1 (Fn) |
|---|---|---|---|---|---|---|---|---|---|---|---|---|
| Echi | | 0.008 | 0.06 | 0.0036 | 0.0004 | 0.0003 | | 0.046 | | 0.002 | 0.002 | 3E-04 |
| 287 | GPenGRGDSPCA (73) | 5.6 | | 24.2 | | 1.12 | | | 90 | | 0.34 | 0.06 |
| 198 | GRGDSPDG (9) * | 0.9 | | | 2.1 | 0.037 | | | | 0.004 | 0.053 | 0.05 |
| 247 | GPenGHRGDSPCA (74) | 6.3 | | | | 0.88 | | | | | 1.6 | 0.36 |
| 100 | GPenRARGDNPCA (75) | 3.1 | | 10.8 | 15 | 0.18 | | | | 0.078 | 0.088 | 0.003 |
| 976 | PmpRGDSPPenG (76) | 1.7 | | | | 0.29 | | | | | 0.21 | |
| 200 | AcCNPRGD(YOMe)RCNH2 (77) | 139 | >100 | 23.8 | 83 | 18.5 | >400 | 2.1 | >400 | 0.2 | 3.4 | 7.7 |
| 676 | GPmcRGDCA (57) | 1.8 | | | | 0.58 | | | | | 0.086 | 0.55 |
| 317 | KPenGFRGDEPCR (63) | 6.8 | | | 100 | 3.4 | | | | | 7 | 2 |
| 31 | KPenGFRGDDPCR (64) | 168 | | 500 | | 13.3 | >400 | 400 | | 1.5 | 9 | 12.2 |
| 310 | GPenAARGDNPCA (78) | 1.2 | | | | 0.17 | | | | | 0.11 | 0.003 |
| 529 | GPenI(dF)RGDTPCA | 85 | >100 | 53.3 | | 6.4 | | | | | 7 | 1.9 |
| 99 | GPenIFRGDTFCA (79) | 15 | | | | 0.72 | | | | | | |
| 65 | GPenAARGDSPCA (44) | 3.0 | >10 | 17.6 | 57 | 0.10 | | | | 0.05 | 0.019 | 0.68 |
| 931 | GRGDSPDF (10) | 1.6 | | | | 0.061 | | | | | 0.19 | 0.12 |
| 448 | GPenIARGDDLCA (34) | 5.2 | >10 | 2.2 | 4.1 | 0.25 | | | | 0.015 | 0.086 | 0.84 |
| 451 | GPenGERGDNYCA (59) | 6.1 | | | | 0.58 | | | | | 0.35 | 0.28 |
| 959 | FRGDSPEG (11) | 3.8 | | | | 0.97 | | | | | 0.4 | 2 |
| 6 | AcPenAARGDN(dhP)CNH2 (80) | 4.1 | | 2.5 | 26 | 0.49 | | | | 0.059 | 0.33 | 0.37 |
| 20 | AcCAARGDN(Tic)CNH2 (35) | 1.0 | 7.7 | 0.44 | 2 | 0.05 | 12.5 | 37.2 | 4.1 | 0.005 | 0.76 | 0.27 |
| 138 | GPenRARGDDVCA (81) | 1.4 | >10 | | 2 | 0.33 | | | | 0.026 | 0.018 | 0.02 |
| 144 | GRGDTFENH2 (12) | 1.2 | | 22 | | 0.13 | | | 21.2 | 0.06 | 0.35 | 0.019 |
| 214 | AcPenFARGDNPCNH2 (51) | 0.8 | | | 3.6 | 0.066 | | | | 0.009 | 0.002 | 0.35 |
| 220 | AcFCRGDTFCNH2 (22) | 1.1 | | | | 0.13 | | | | | 0.14 | 0.005 |
| 221 | GPenEARGDNPCA (82) | 1.2 | >10 | | | 0.203 | | | | 0.014 | 0.008 | 0.26 |
| 228 | AcCRGDNPPenNH2 (31) | 1.4 | | 5.5 | 10 | 0.031 | | | | 0.017 | 0.75 | 0.11 |
| 813 | AcPenAARGDNICNH2 (83) | 2.6 | | | | 0.06 | | | | | 0.3 | 0.09 |
| | | | | | | | | | | | 0.62 | 0.11 |

FIG. 2A

Activity of Osteoporosis Peptides*

| Peptide | Sequence | chick OC detach (FCS) | Chick nonOC (FCS) | Rat OC attach (FCS) | Rat Bone (Pits) | Cell-Based Assays JY attach αvβ3/Vn | NRK attach (FCS) | Plate. Aggreg. (hep) | MG63 attach (FCS) | Receptor Assays αvβ3 (Vn) | αvβ5 (Vn) | α5β1 (Fn) |
|---|---|---|---|---|---|---|---|---|---|---|---|---|
| 832 | AcPenAARGDN(Tic)CNH2 (47) | 0.6 | 1.6 | 0.96 | 6.1 | 0.019 | 7.9 | 48.3 | 3.7 | 0.003 | 0.003 | 0.010 |
| 812 | AcCRGDS(Tic)CNH2 (48) | 0.6 | 3.3 | 0.44 | 1.4 | 0.0054 | | | | 0.006 | 0.002 | 0.008 |
| 831 | AcPenTARGDNPCNH2 (84) | 1.8 | | | | 0.006 | | | | | 0.51 | |
| 814 | GPenAARGDDVCANH2 (30) | 1.8 | >10 | 19.9 | 41 | 0.58 | >400 | | | 0.042 | 2.14 | 0.25 |
| 825 | RGDSPENH2 (13) | 2.7 | | | | 0.25 | | | | | 0.75 | 0.035 |
| 390 | GRARGDNPENH2 (14) | 1.8 | | | | 0.098 | | | | | 0.96 | 0.02 |
| 385 | AcCAARGDY(Tic)CNH2 (85) | 4.8 | | 5.8 | | | | | | 0.01 | | 0.01 |
| 386 | RGDDVENH2 (3) | 1.2 | >10 | 1.9 | 0.9 | | >400 | 87.8 | >100 | 0.026 | 0.53 | 0.039 |
| 389 | GPenAARGDVPCANH2 (60) | 2.2 | | | | 0.08 | | | | | 0.57 | 0.037 |
| 368 | GRGDDVDNH2 (7) | 1.6 | >10 | | 3.8 | 0.053 | | | | 0.009 | 0.3 | 0.18 |
| 387 | AcPenFARGDSPCNH2 (86) | 1.5 | | | | 0.13 | | | | | | 0.02 |
| 365 | AcPen(YOMe)ARGDNPCNH2 (87) | 1.5 | | | | 0.033 | | | | | 0.61 | 0.01 |
| 375 | (p-C1-F)RGDTPDNH2 (88) | 2.7 | | | | 0.03 | | | | | | |
| 366 | RGDTPENH2 (15) | 3.2 | | | | 0.07 | | | | | 0.21 | 0.02 |
| 373 | AcPenFARGDN(Tic)CNH2 (45) | 0.6 | 2.5 | 0.15 | 1.0 | 0.0018 | 5.1 | 18.9 | 0.71 | 0.002 | 0.003 | 0.002 |
| 388 | AcCRGDSPCNH2 (27) | 1.6 | | | | 0.22 | | | | | 0.97 | |
| 383 | GPenAARGDEPCNH2 (89) | 3.2 | | | | 1.00 | | 178.5 | | | 1.9 | 0.13 |
| 186 | GPenAARGDDTCNH2 (32) | 4.7 | >10 | 13.5 | | 0.0037 | | | | 0.093 | 5.7 | 0.19 |
| 183 | AcPen(YOMe)ARGDN(Tic)CNH2 (46) | 0.4 | 2.2 | 0.13 (77) | 1.3 | 0.002 | 2.2 | 22 | 0.43 | 0.002 | 0.008 | 0.005 |
| 193 | G(Pen)ELRGDGWCNH2 (61) | | | | | | | | | | | 1.7 |
| 191 | MpaRGDDVCNH2 (28) | 1.1 | >10 | 1.9 | 3 | 0.009 | >400 | 76.7 | >100 | 0.036 | 4.83 | 0.36 |
| 202 | AcPenFARGDDN(Tic)CNH2 (36) | 0.12 | 1.2 | 0.82 | 2 | 0.018 | 12.1 | 6.1 | 1.9 | 0.005 | 0.006 | 0.006 |
| 196 | AcCAARGDS(Tic)CNH2 (29) | 0.4 | 1.7 | 2.4 | | 0.0037 | | | | 0.007 | 0.011 | 0.031 |
| 197 | βAlaAARGDN(Tic)DNH2 (90) | 0.7 | 6.6 | 0.28 | | 0.047 | 10 | | | 0.004 | 0.036 | 0.022 |
| 206 | AcCAARGDT(Tic)CNH2 (91) | 0.2 | 1.9 | 1.6 | | 0.0025 | 3.6 | | | 0.002 | 0.008 | 0.029 |
| 199 | GCEPRGDN(Tic)CANH2 (43) | 0.35 | 1.8 | 0.17 | | 0.017 | 17.2 | | | 0.006 | 0.036 | 0.071 |
| 192 | AcCRGDS(Tic)(Pen)NH2 (39) | | | 0.85 | | | 5 | 17.9 | | 0.01 | 0.014 | 0.04 |
| 442 | GRGDEPDG (16) | | | 3.2 | | | | | | | 0.014 | |
| 437 | AcCRGDT(Tic)CNH2 (37) | | | 0.94 | | | 4.9 | | | 0.003 | 0.006 | 0.008 |

FIG. 2B

Activity of Osteoporosis Peptides*

| Peptide | | Cell-Based Assays | | | | | | Receptor Assays | | |
|---|---|---|---|---|---|---|---|---|---|---|
| | Sequence | chick OC detach (FCS) | Chick nonOC (FCS) | Rat OC attach (FCS) | Rat Bone (Pits) | JY attach aVβ3/Vn | NRK attach (FCS) | Plate. Aggreg. (hep) | MG63 attach (FCS) | aVβ3 (Vn) | aVβ5 (Vn) | a5β1 (Fn) |
| 4.34 | AcPenAARGDN(1-Nal)CNH2 (92) | | | (38) | | | | | | | | |
| 422 | GPen(dE)ARGDSPCNH2 | | | (40) | | | | | | | | |
| 4.38 | AcCAARGDN(fp)CNH2 (93) | | | 20 | | | | | | 0.23 | | |
| 441 | AcCRGDN(Tic)(Pen)NH2 (49) | | | 0.56 | | | 33.2 | | 7 | 0.004 | 0.013 | 0.06 |
| 4.28 | GPenGFRGDEPCNH2 (62) | | | (100) | | | | | | | | |
| 424 | GPenGFRGDSPCNH2 (94) | | | (82) | | | | | | | | |
| 429 | AcCRGDS(Tic)CAKNH2 (50) | | | 2.0 | | | | | | 0.005 | 0.018 | 0.015 |
| 427 | AcPenFARGDDVCNH2 (95) | | | 2.8 | 5 | | >400 | 63.9 | | 0.026 | 2.89 | 0.53 |
| 418 | AcPen(2-Nal)ARGDNPCNH2 (96) | | | (24) | | | | | | | | |
| 425 | AcRGDDVGNH2 (2) | | | 10 | | | | | | 1.64 | | |
| 4.36 | AcCAARGDN(7-OMeTic)CNH2 (97) | | | | | | | | | 0.62 | | |
| 432 | ACRGDSP(Pen)NH2 (98) | | | | | | | | | | | |
| 4.31 | AcCAARGDN(Tic)CKNH2 (52) | | | 0.64 | | | 20 | | 8.7 | 0.004 | 0.027 | 0.017 |
| 4.35 | AcPenI(nMeF)RGDTFCNH2 (99) | | | (87) | | | | | | | 0.028 | |
| 673 | TAPGKHPNRCAARGDN(Tic)CNH2 (100) | | | 1.32 | | | | | | | | |
| 84 | AcPenFARGDD(PgL)CNH2 (101) | | | (41) | | | | | | 0.021 | 5.49 | 0.26 |
| 90 | AcCFARGDT(Tic)CNH2 (102) | | | 2.0 | | | | | | 0.005 | | |
| 86 | AcCRGDDVCNH2 (17) | | | 12.5 | | | | | | 0.065 | 0.86 | |
| 159 | (MPa)RGDD(t-BuG)CNH2 (53) | | | 0.46 | 1.1 | | >400 | 25.8 | >400 | 0.006 | 1.07 | 0.32 |
| 92 | (Mpa)RGDD(cha)CNH2 (103) | | | 12.9 | | | | | | 0.15 | 0.84 | |
| 94 | AcCIARGDDVCNH2 (18) | | | 9.3 | | | | | | 0.05 | 1.08 | |
| 93 | RGDN(Tic)ENH2 (104) | | | 1.3 | | | 31.2 | | >400 | 0.005 | 0.092 | 0.009 |
| 713 | AcCAARGDN(Tic)CAKNH2 (105) | | | 3.3 | | | | | | 0.023 | 0.14 | |
| 172 | AcCRGDT(Tca)CNH2 (106) | | | 1.2 | | | | | | 0.004 | 0.041 | 0.03 |
| 88 | AcCEPRGDDVCNH2 (19) | | | 9.2 | | | >400 | | | 0.077 | 1.22 | |
| 125 | AcCRGDT(Oic)CNH2 (107) | | | 133 | | | | | | 0.11 | 0.28 | |
| 122 | AcCEARGDDVCNH2 (20) | | | 19.05 | | | | | | 0.042 | 5.17 | |
| 109 | Ac(Pen)EARGDDVCNH2 (108) | | | 2.6 | | | | | | 0.04 | 1.5 | 0.96 |
| 110 | GAARGDS(Tic)ENH2 (54) | | | 0.5 | | | | | 3.2 | 0.009 | 0.033 | 0.025 |

FIG. 2C

Activity of Osteoporosis Peptides*

| Peptide | | Cell-Based Assays | | | | | | Receptor Assays | | |
|---|---|---|---|---|---|---|---|---|---|---|
| | Sequence | chick OC detatch (FCS) | Chick nonOC attach (FCS) | Rat OC attach (FCS) | Rat Bone (Pits) | JY attach αVβ3/Vn | NRK attach (FCS) | Plate. Aggreg (hep) | MG63 attach (FCS) | αVβ3 (Vn) | αVβ5 (Vn) | α5β1 (Fn) |
| 126 | Ac(Pen)AARGDN(homP)CNH2 (109) | | | 13.9 | | | | | | | | |
| 129 | RGDS(Adp)NH2 (110) | | | 2.5 | | | | | | | 0.84 | |
| 108 | AcCEPRGDN(Tic)CNH2 (55) | | | 0.32 | 2 | | 3.2 | 111.7 | >400 | 0.016 | 0.03 | |
| 109 | Ac(Pen)EARGDDVCNH2 (108) | | | 3.98 | | | | | | 0.005 | 0.029 | 0.12 |
| 110 | GAARGDS(Tic)ENH2 (54) | | | ~2.5 | | | | | | | | |
| 105 | (Pmp)AARGDN(Tic)CNH2 (111) | | | 1.0 | | | | | | | | |
| 124 | AARGDDV(Adp)NH2 (112) | | | 5.2 | | | | | | | | |
| 118 | Ac(Pen)EPRGDDVCNH2 (113) | | | 2.2 | | | | | | | | |

*— numbers in parentheses are SEQ ID NOS:

CYCLIC RGD PEPTIDES

5  G-Pen-R-A-R-G-D-D-L-C-A (SEQ ID NO: 67)
G-Pen-R-A-R-G-D-D-nL-C-A (SEQ ID NO: 68)
G-Pen-A-A-R-G-D-D-I-C-A (SEQ ID NO: 69)
G-dPen-G-R-G-D-V-C-NH$_2$
βAla-R-A-R-G-D-N-P-D-NH$_2$ (SEQ ID NO: 70)

10  Ac-Pen-A-A-R-G-D-Orn-P-C-NH$_2$ (SEQ ID NO: 65)
Ac-Pen-F-A-R-G-D-N-Pgl-C-NH$_2$ (SEQ ID NO: 71)
Ac-C-A-A-R-G-D-T-P-C-NH$_2$ (SEQ ID NO: 21)
Ac-F-C-R-G-D-T-F-C-NH$_2$ (SEQ ID NO: 22)
Ac-C-I-F-R-G-D-T-F-C-NH$_2$ (SEQ ID NO: 23)
Ac-Pen-I-(p-Cl-F)-R-G-D-T-F-C-NH$_2$ (SEQ ID NO: 72)

15  F-R-G-D-T-F-E-NH$_2$ (SEQ ID NO: 24)
R-G-D-S-Tic-E-NH$_2$ (SEQ ID NO: 41)

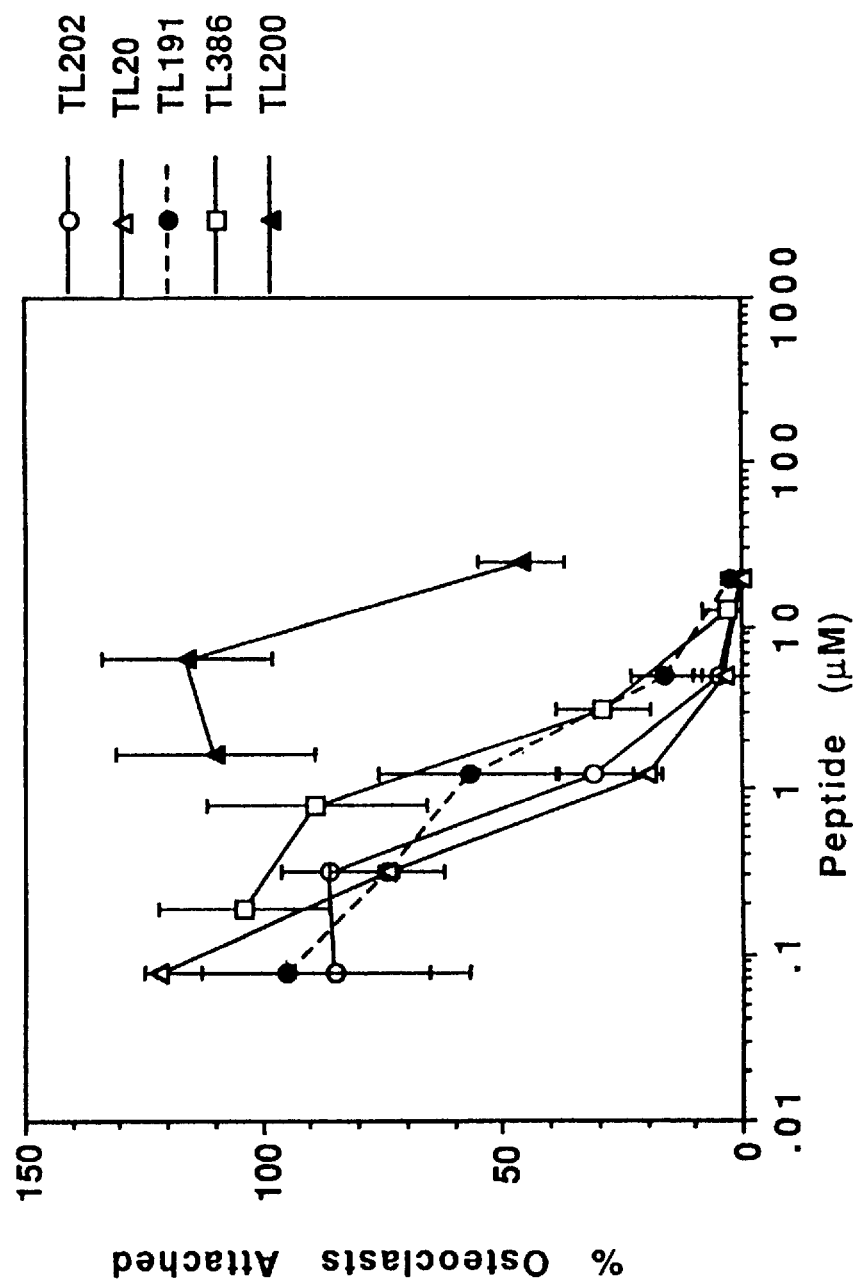

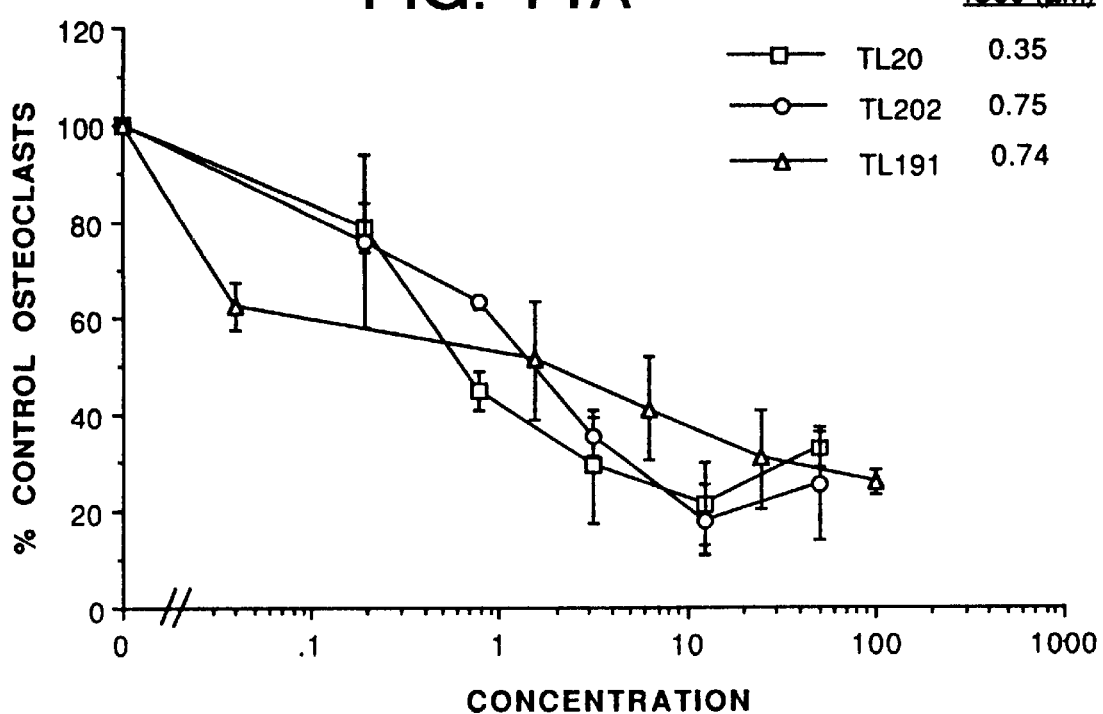
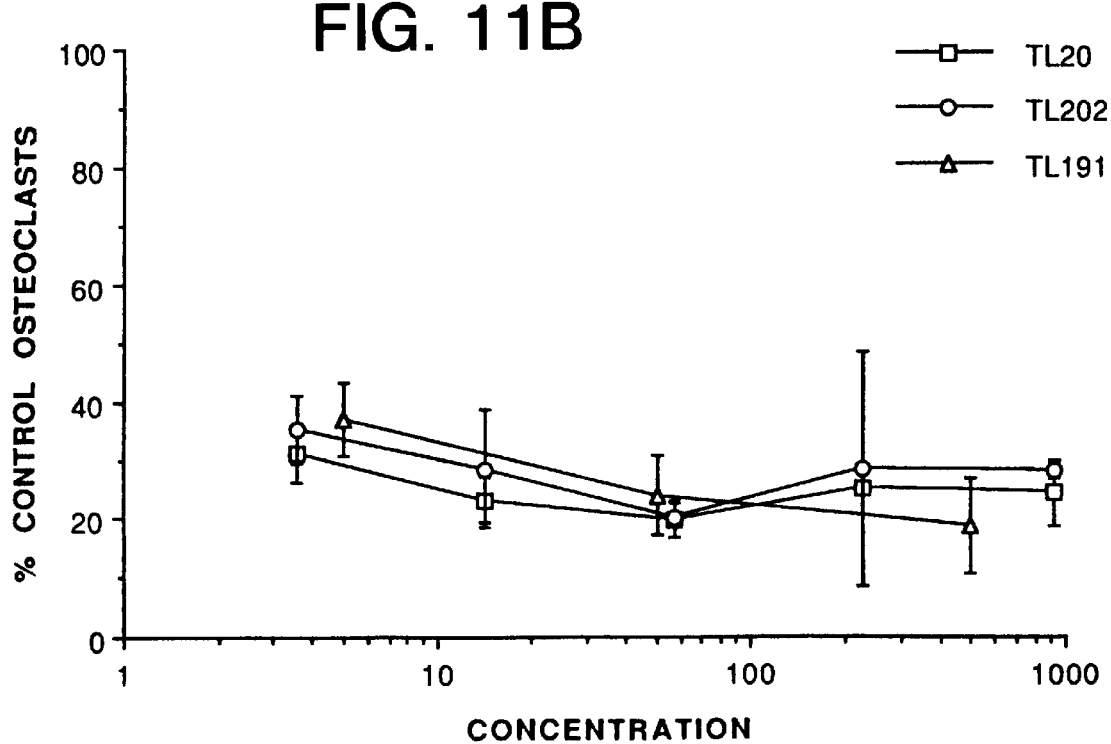

5,770,565

1

PEPTIDES FOR REDUCING OR INHIBITING BONE RESORPTION

This application is a continuation-in-part of U.S. Ser. No. 08/227,316, which was filed Apr. 13, 1994, and subsequently abandoned.

BACKGROUND OF THE INVENTION

1. Field of the Invention

This invention relates generally to the field of bone metabolism and more specifically to peptides that can reduce or inhibit bone resorption.

2. Background Information

Bone is a dynamic tissue that is continually remodeled throughout life depending on factors such as nutrition and the load the bone must carry. Normal bone formation depends on the delicate balance between new bone addition and old bone resorption. Bone resorption is initiated when an osteoclast attaches to the surface of mineralized bone, forms a tight sealing zone and secretes enzymes that begin the resorption process. After a period of several hours to days, the osteoclast detaches from the bone, leaving a pit on the bone surface. Under normal conditions, the pit is a target for osteoblasts, which deposit a material that ultimately becomes new bone.

Bone loss can result when the bone resorptive process is dominant over the bone formative process. Such a condition can occur, for example, when a previously active person becomes sedentary or incapacitated due to an injury or illness, when a person fails to ingest an adequate amount of vitamins and minerals or in various pathological conditions. A condition of excessive bone loss, which is called osteoporosis, is common in elderly persons.

When osteoporosis is caused by a mineral or vitamin deficiency, the condition often can be treated by supplementing the person's diet with the appropriate nutrient. However, diet supplementation is not always effective and, in most cases, osteoporosis cannot be treated. In severe cases, osteoporosis can result in the formation of fragile bones that readily fracture when placed under a minimal load or stress. Thus, a need exists for agents that can reduce or inhibit bone resorption in a subject. The present invention satisfies this need and provides related advantages as well.

BRIEF DESCRIPTION OF THE FIGURES

FIG. 1 shows the names and structures of Tic and representative Tic analogs.

FIG. 2 lists and demonstrates the activity of various RGD peptides of the invention. All of the peptides are cyclic except 425, which is linear. Values indicated are mean $IC_{50}$ values ($\mu$M), except that numbers in parentheses, which represent the percent of osteoclasts remaining adherent, were obtained for a single experiment using 5 $\mu$M peptide. OC, osteoclast; FCS, fetal calf serum; Echi, echistatin; JY, human B lymphocyte-derived JY cell line; Vn, vitronectin; Hep, heparin. Regarding the peptide sequences, "NH2" indicates the presence of an amide group at the C-terminus; dE indicates the D-amino acid form of glutamic acid; dF indicates the D-amino acid form of phenylalanine. Other abbreviations are listed in Table 1 (see, also, FIG. 1, for Tic and Tic analogs). SEQ ID NO. is listed for peptides containing only L-amino acids.

FIG. 3 lists additional RGD peptides of the invention. Underlining indicates the amino acids in the cyclic region of the peptide. SEQ ID NO. is listed for peptides containing only L-amino acids. dPen indicates the D-amino acid form of penicillamine. Other abbreviations are listed in Table 1 (see, also, FIG. 1, for Tic and Tic analogs).

FIG. 7 demonstrates the effectiveness of various peptides in the rat osteoclast attachment assay using fetal calf serum as substrate.

FIG. 11 demonstrates the effectiveness of various RGD peptides of the invention in the rat osteoclast attachment assay using collagen as substrate.

DETAILED DESCRIPTION OF THE INVENTION

Figure 4:
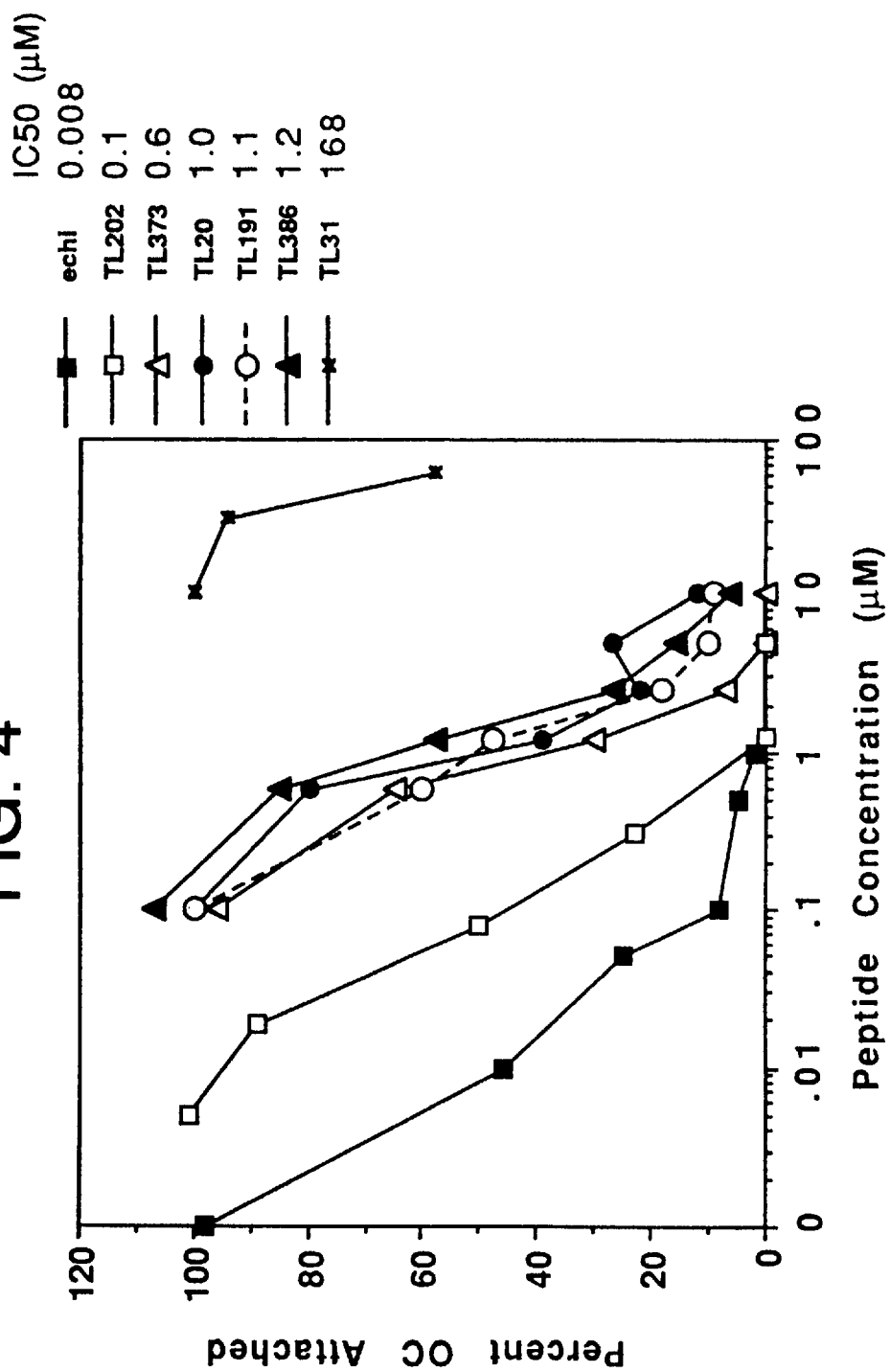
FIG. 4 demonstrates the dose response of various RGD peptides in the chick osteoclast cell detachment assay. The IC50 was calculated by determining the dose of a peptide that results in the detachment of 50% of the osteoclasts and is shown for each peptide. Echi indicates echistatin. Peptide TL31 is a negative control.

The present invention provides non-naturally occurring Arg-Gly-Asp (RGD) peptides that can inhibit bone resorption and can inhibit the binding of an osteoclast to a matrix such as bone. RGD peptides of the invention also can bind the $\alpha_V\beta_3$ integrin and, therefore, can inhibit or promote $\alpha_V\beta_3$-mediated cell attachment. As used herein, the term "Arg-Gly-Asp peptide" or "RGD peptide" means a peptide having at least one Arg-Gly-Asp-containing sequence, as defined below, which can function as a binding site for an integrin type receptor (see Table 1 for amino acid codes). Integrin receptors can bind a variety of RGD-containing peptides (see, for example, Ruoslahti et al., In *Morphoregulatory Molecules* (G. M. Edelman et al., eds. 1990); Ruoslahti, *J. Clin. Invest.* 87:1–5 (1991)).

It is intended that the term "RGD peptide" in its broadest sense includes a peptide comprising Arg-Gly-Asp or a functional equivalent of Arg-Gly-Asp. For example, an amino acid such as lysine, homoarginine (homoArg) or a mimic of these amino acids is a functional equivalent of arginine. Similarly, mimics of Gly and Asp are functional equivalents of glycine and aspartic acid, respectively. Therefore, a peptide comprising, for example, Lys-Gly-Asp is considered an RGD peptide within the meaning of the present invention. As used herein, the term "mimic" means an amino acid or an amino acid analog that has the same or a similar functional characteristic of an amino acid. Thus, for example, an arginine analog can be a mimic of

| Single letter code | Three letter code | Amino acid*+ |
|---|---|---|
| | Adp | α-aminoadipic acid |
| A | Ala | Alanine |
| | βAla | β-alanine |
| | α-ABA | α-Amino isobutyric acid |
| R | Arg | Arginine |
| N | Asn | Asparagine |
| D | Asp | Aspartic acid |
| | Cha | Cyclohexyl-alanine |
| | Chg | cyclohexyl-glycine |
| | Cit | Citrulline |
| C | Cys | Cysteine |
| Q | Gln | Glutamine |
| E | Glu | Glutamic acid |
| G | Gly | Glycine |
| | t-BuG | tert-butyl Glycine |
| H | His | Histidine |
| | Hpa | Homophenylalanine |
| I | Ile | Isoleucine |
| L | Leu | Leucine |
| | nL | norleucine |
| K | Lys | Lysine |
| | Maa | β-[(methylsulfonyl)aminoalanine |
| M | Met | Methionine |
| | Mpr | β-Mercaptopropionic acid |
| | N-Me-R | N-methyl-arginine |
| | Npg | neopentyl-glycine |
| | OMeTic | O-methyl-Tic+ |
| | Orn | Ornithine |
| | p-amino-Phe | para-amino-phenylalanine |
| | Pen | Penicillamine |
| | PgL | phenyl-glycine |
| F | Phe | Phenylalanine |
| | p-Cl-F | para-chloro-phenylalanine |
| | p-iodo-Phe | para-iodo-phenylalanine |
| | Pmc | β,β-pentamethylene cysteine |
| | Pmp | β,β-pentamethylene-β-mercaptopropionic acid |
| P | Pro | Proline |
| | homP | homoproline |
| | dhp | dehydroproline |
| | fp | 3-phenylproline |
| S | Ser | Serine |
| | Tca | 1,2,3,4-tetrahydro-β-carboline-3-carboxylic acid |
| | tetrazol | β-(1(2)H-tetrazol-5-yl)-alanine |
| T | Thr | Threonine |
| W | Trp | Tryptophan |
| Y | Tyr | Tyrosine |
| | YOMe | O-methyl-tyrosine |
| V | Val | Valine |
| | 2-Nal | β-(2-naphthyl) Ala-OH |
| | 1-Nal | β-(1-naphthyl) Ala-OH |

*includes amino acids and analogs thereof.
+for Tic and Tic analogs, see Figure 1.

arginine if the analog contains a side chain having a positive charge at physiologic pH, as is characteristic of the guanidinium side chain reactive group of arginine. A peptide mimetic or peptidomimetic is an organic molecule that retains similar peptide chain pharmacophore groups as are present in the corresponding peptide. Peptide mimetics also can be functional equivalents of Arg-Gly-Asp.

In one aspect, the RGD peptides of the invention are grouped based on the pharmacophore. As used herein, the term "pharmacophore" is defined as a particular three-dimensional arrangement of functional groups that is required for a compound to produce a particular response or have a desired activity. The invention provides, for example, a pharmacophore, abbreviated "RGDNTic," (SEQ ID NO: 56) which is contained within a non-naturally occurring peptide comprising the sequence:

$X_1\ X_2\ X_3\ X_4$ GD $X_5\ X_6\ X_7\ X_8$ (SEQ ID NO: 25)

wherein $X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus; $X_2$ is 0 or 1 amino acid, which, when $X_2$ is one amino acid, can form a bridge with $X_7$; $X_3$ is 0, 1 or 2 amino acids, which when $X_3$ is two amino acids, the amino acids can be a pair consisting of Phe-Ala, Ala-Ala, Glu-Ala, Tyr-Ala, Arg-Ala, Ile-Ala, Glu-Pro, Ile-Phe, (2-Nal)-Ala or analogs or mimics thereof; $X_4$ is a positively charged amino acid such as Arg, Lys, homoArg or analogs or mimics thereof; $X_5$ is an amino acid such as Asn, Ser, Thr or mimics or analogs thereof, which can provide a hydrogen bond interaction with an integrin receptor; $X_6$ is an amino acid such as Tic, Pro, Phe, Ile or analogs or mimics thereof, which have the characteristics of hydrophobicity and/or conformational constraint; $X_7$ is a residue capable of forming a bond with an amino acid of $X_2$, or with $X_3$ when $X_2$ is 0, or with $X_4$ when $X_2$ and $X_3$ are 0, to conformationally restrain the peptide; and $X_8$ is $-NR_3R_4$ (wherein $R_3$ is an H or alkyl group and $R_4$ is an H or alkyl group) or $-COOR_5$ (wherein $R_5$ is an H or alkyl group) or 1 to 10 amino acids, which can be protected as an amide at the C-terminus, and wherein when $X_5$ is serine and $X_6$ is proline, $X_3$ is 0 or 2 amino acids. The abbreviation "RGDNTic" (SEQ ID NO: 56) includes all peptides encompassed by this formula.

The invention also provides, for example, a pharmacophore, abbreviated "RGDDV," (SEQ ID NO: 1) which is contained within a non-naturally occurring peptide comprising the sequence:

$X_1\ X_2\ X_3\ X_4$ GD $X_5\ X_6\ X_7\ X_8$ (SEQ ID NO: 26)

wherein $X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus; $X_2$ is 0 or 1 amino acid, which, when $X_2$ is one amino acid, can form a bridge with $X_7$; $X_3$ is 0, 1 or 2 amino acids, which when $X_3$ is two amino acids, the amino acids can be a pair consisting of Glu-Ala, Tyr-Ala, Arg-Ala, Ile-Gly, Glu-Pro, or a hydrophobic amino acid followed by a second amino acid such as Ile-Ala, Ile-Phe, (2-Nal)-Ala, Phe-Ala or Ala-Ala, or analogs or mimics thereof; $X_4$ is a positively charged amino acid such as Arg, Lys, homoArg or analogs or mimics thereof; $X_5$ is an amino acid such as Asp, Glu, β-(1(2)H-tetrazol-5-yl)-alanine or analogs or mimics thereof such as the sulfonamide derivative, Maa (see Example I.D.), which can form an ionic or similar interaction with an integrin receptor; $X_6$ is an amino acid such as Leu, Ile, Val, Thr, Nle or analogs or mimics thereof, which has an aliphatic side chain, or is an aliphatic non-natural amino acid that is hydrophobic such as t-BuG, Cha, Chg, Npg or phenylglycine; $X_7$ is a residue capable of forming a bond with a bridging amino acid of $X_2$, or with $X_3$ when $X_2$ is 0, or with $X_4$ when $X_2$ and $X_3$ are 0, to conformationally restrain the peptide; and $X_8$ is $-NR_3R_4$ (wherein $R_3$ is an H or alkyl group and $R_4$ is an H or alkyl group) or $-COOR_5$ (wherein $R_5$ is an H or alkyl group) or 1 to 10 amino acids, which can be protected as an amide at the C-terminus. The abbreviation "RGDDV" (SEQ ID NO: 1) includes all peptides encompassed by this formula.

In another aspect, the present invention provides RGD-containing cyclic peptides having the following sequences: G-R-G-D-E-P-D-G (SEQ ID NO: 16); R-G-D-N-I-E-NH$_2$ (SEQ ID NO: 24); G-Pmc-R-G-D-C-A (SEQ ID NO: 57); G-Pen-G-R-G-D-N-Y-C-A (SEQ ID NO: 58); G-Pen-G-E-R-G-D-N-Y-C-A (SEQ ID NO: 59); G-Pen-A-A-R-G-D-V-P-C-A-NH$_2$ (SEQ ID NO: 60); G-Pen-E-L-R-G-D-G-W-C-NH$_2$ (SEQ ID NO: 61); G-Pen-G-F-R-G-D-E-P-C-NH$_2$ (SEQ ID NO: 62); G-Pen-G-E-R-G-D-N-Y-C-A (SEQ ID NO: 63); K-Pen-G-F-R-G-D-E-P-C-R (SEQ ID NO: 64); K-Pen-G-F-R-G-D-D-P-C-R (SEQ ID NO: 65) and Ac-Pen-A-A-R-G-D-Orn-P-C-NH$_2$ (SEQ ID NO: 66) (underlined amino acid residues indicate the cyclic region of a peptide). In an additional aspect, the invention provides a linear peptide having the sequence: Ac-R-G-D-D-V-G-NH$_2$ (SEQ ID NO: 2). These and other peptides are useful for practicing the invention.

As used herein, the term "amino acid" is meant in its broadest sense to include naturally occurring proteogenic amino acids and imino acids as well as non-naturally occurring amino acids and imino acids and analogs and mimics thereof. As used herein, the term "proteogenic" indicates that the amino acid can be incorporated into a protein in a cell through well known metabolic pathways. In view of this broad definition of an amino acid, one skilled in the art would know that reference herein to an amino acid, unless specifically indicated otherwise, includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. For example, Tic is a conformationally constrained analog of Phe and a benzofused analog of Pro. Tic analogs include, for example, Idc, Dic, Oic, Tca, and 7-OMe-Tic (see FIG. 1 for structure and full names of Tic and Tic analogs). Other conformationally constrained amino acids are known in the art and include, for example, proline derivatives (Chung et al., *J. Org. Chem.* 55:270–275 (1990), which is incorporated herein by reference).

The choice of including an (L)- or a (D)-amino acid in an RGD peptide of the present invention depends, in part, on the desired characteristics of the peptide. For example, the incorporation of one or more (D)-amino acids can confer increased stability on the peptide in vitro or in vivo, above that provided by conformational constraint, and can allow the peptide to remain active in the body for an extended period of time. The incorporation of one or more (D)-amino acids also can increase or decrease the pharmacological activity of the peptide as determined, for example, using the assays described in Examples II and III, below, or other in vitro or in vivo assays for determining, for example, osteoclast binding to a matrix or osteoclast activity. The skilled artisan can determine the desirable characteristics required of an RGD peptide of the invention by taking into consideration, for example, the age and general health of a subject.

Increased stability of a disulfide bonded peptide of the invention also can be conferred by incorporating a hydrophobic amino acid residue such as phenylalanine at position $X_1$ or $X_8$ or both $X_1$ and $X_8$ in an RGDNTic (SEQ ID NO: 56) or RGDDV (SEQ ID NO: 1) pharmacophore as disclosed herein. The presence of such a residue can stabilize the disulfide bond against enzymatic degradation (see Bauer et al., *Life Sciences* 31:1133–1140 (1982)). For example, peptide 220 (see FIG. 2), which is within the RGDNTic (SEQ ID NO: 56) class of peptides, contains a phenylalanine residue at position $X_1$ and exhibits a relatively long half-life in serum. Methods for determining pharmacokinetic properties of a peptide of the invention such as half-life of a peptide in serum are routine in the art (see, for example, *Experimental and Surgical Technique in the Rat,* 2d ed., chapters 1, 2 and 3 (H. B. Waynforth and P. A. Flecknell; Academic Press Ltd., London 1992); *Applied Biopharmaceutics and Pharmacokinetics,* 3d ed., chapters 3–5 and 9 (L. Shargel and A. B. C. Yu; Appelton and Lange, USA 1993), each of which is incorporated herein by reference). In addition, the half-life of a peptide in a subject can be determined, for example, by high performance liquid chromatography (HPLC) of serum samples collected from the subject at various times following administration of the peptide. One skilled in the art would know how to select appropriate elution buffers for HPLC based on the physicochemical properties of a particular peptide.

The RGD peptides of the invention can be chemically synthesized using, for example, an automated synthesizer (see Example I). Selective modification of a reactive group such as an amino acid side chain or an N- or C-terminal group in a peptide can impart desirable characteristics to an RGD peptide of the invention. A peptide can be manipulated while still attached to the resin following chemical synthesis or after cleavage from the resin to obtain, for example, an N-terminal modified peptide such as the acetylated peptides disclosed herein (see Example I and FIGS. 2 and 3). Peptides also can be synthesized containing the C-terminal carboxy group or a C-terminal amide as described in Example I. A newly synthesized peptide can be purified using a method such as reverse phase HPLC (RP-HPLC), as described in Example I, or other methods of separation based on the size or charge of the peptide. Similarly, well known methods such as amino acid sequence analysis or mass spectrometry, as described in Example I, are available for characterizing the structure of the RGD peptide.

An RGD peptide of the invention can be constrained by various methods, including, for example, formation of a disulfide bond or a lactam bond between $X_7$ and one of either $X_2$, $X_3$ or $X_4$. Residues capable of forming a disulfide bond include Cys, Pen, Pmp, Pmc and Mpr (see Table 1). Residues capable of forming a lactam bridge include Asp, Glu, Lys, Orn and $\alpha,\beta$-diaminopropionic acid and $\alpha$-aminoadipic acid. The RGD peptides disclosed herein can cyclize, for example, via a lactam bond, which can utilize a side chain group of $X_7$ to form a covalent attachment to the N-terminal amine of $X_2$ or $X_3$ (when $X_2$ is 0) or $X_4$ (when $X_2$ and $X_3$ are 0). In particular, $X_7$ in a lactam-bonded peptide can be an Asp or a Glu residue. Conformational constraint also can be effected by the choice of a residue such as proline that is incorporated into a peptide or by synthesis of a peptidomimetic having a particular conformation.

RGD peptides of the invention comprising an RGDNTic (SEQ ID NO: 56) pharmacophore or an RGDDV (SEQ ID NO: 1) pharmacophore are exemplified by peptides shown in FIGS. 2 and 3. The minimal elements of the cyclic RGD peptides of the invention include 1) a five amino acid pharmacophore such as the pharmacophores abbreviated RGDNTic (SEQ ID NO: 56) or RGDDV (SEQ ID NO: 1) and 2) a means of conformational restraint. Peptide 812 (Ac-CRGDS(Tic)Cs-NH$_2$) (SEQ ID NO: 48) from the RGDNTic (SEQ ID NO : 56) pharmacophore group and peptide 386 (RGDDVE-NH$_2$; SEQ ID NO: 3) from the RGDDV (SEQ ID NO: 1) pharmacophore group exemplify RGD peptides that have these minimally essential elements and demonstrate activity (see FIG. 2). Peptides are referred to herein by a number, which can be shown either alone or preceded by the letters, TL.

Peptides of the RGDNTic (SEQ ID NO: 56) pharmacophore group are characterized, in general, as having increased potency, whereas the peptides of the pharmacophore RGDDV (SEQ ID NO: 1) group generally have higher receptor selectivity. However, RGD peptides having both characteristics also were identified (see, for example, peptides 191 and 159; FIG. 2). As used herein, the term "potency" or "potent" means that a peptide of the invention is active at a relatively low concentration in the assays described in Examples II and III. A potent peptide of the invention can be identified, for example, using the assays described in Examples II and III.

As used herein, the term "selective" means that a peptide of the invention preferentially inhibits the binding of cells such as osteoclasts, which are involved in bone resorption, as compared to other cell types to a matrix such as bone. Selectivity can be due, for example, to the ability of a peptide of the invention to bind to $\alpha_V\beta_3$ with greater affinity than it binds to other integrins. Thus, in addition to having selectivity, for example, for osteoclast binding to a matrix, a peptide of the invention also can display receptor selectivity and, therefore, more specifically alter receptor-mediated binding to a matrix. As used herein, the term "receptor selectivity" means that a peptide of the invention can bind to one receptor with greater affinity than it can bind to another receptor. For example, peptides such peptides 368, 814, 191, 84 and 159 have a low $IC_{50}$ value for $\alpha_V\beta_3$ binding as compared to $\alpha_V\beta_5$ binding or $\alpha_5\beta_1$ binding (see FIG. 2) and, therefore, are receptor selective for $\alpha_V\beta_3$. Methods for identifying a selective peptide are described in Example II.

As used herein, the terms "matrix" and "ligand" are used in the broadest sense to mean a material to which a cell such as an osteoclast can bind. Cells can bind to extracellular matrix components such as fibronectin, vitronectin, laminin and collagen. In addition, it is well known that osteoclasts can bind, for example, to bone and to bone matrix proteins such as osteopontin and bone sialoprotein. As disclosed herein, osteoclasts also can bind, for example, to a matrix such as a serum-coated microtiter plate or to a plate having attached thereto an RGD peptide of the invention. In addition, an osteoclast can express specific integrin receptors on its cell surface and, therefore, can bind to a matrix component recognized by the receptor. For example, JY cells express $\alpha_V\beta_3$ integrin receptors and, accordingly, can bind a matrix such as vitronectin (see Example II). Vitronectin is a ligand of the $\alpha_V\beta_3$ receptor.

Osteoclasts attach to bone matrix via integrin-type receptors present on the osteoclast cellular membrane. Integrins are heterodimeric molecules comprised of an $\alpha$ and a $\beta$ subunit. The $\alpha\beta$ integrin receptor binds to molecules in the extracellular matrix, commonly via the Arg-Gly-Asp sequence present in such molecules. Numerous $\alpha$ and $\beta$ subtypes have been identified and the combination of a particular $\alpha$ subtype with a particular $\beta$ subtype contributes to the ligand specificity of the integrin. Some integrins can adopt subtle conformational changes specific to a particular cell type, thus providing an additional level of cell type integrin specificity (Chuntharapai et al., *Exp. Cell Res.* 205:345–352 (1993)).

Osteoclasts can express an $\alpha_V\beta_1$ integrin receptor, as well as $\alpha_V\beta_1$ and $\alpha_2\beta_1$ integrin receptors (Nesbitt et al., *J. Biol. Chem.* 268:16737–16745 (1993)). $\alpha_V\beta_1$ is a fibronectin receptor. As discussed above, the $\alpha_V\beta_3$ integrin is a vitronectin receptor, which can be involved in bone resorption. For example, a monoclonal antibody against $\alpha_V\beta_3$ blocked bone resorption in vitro (Horton et al., *Exp. Cell Res.* 195:368–375 (1991)). The vitronectin receptor present on rat osteoclasts can bind a wide variety of RGD-containing extracellular matrix and bone proteins in vitro, including osteopontin and bone sialoprotein (Helfrich et al., *J. Bone Miner. Res.* 7:335–343 (1992); Reinholt et al., *Proc. Natl. Acad. Sci. USA* 87:4473–4475 (1990); Miyauchi, et al., *J. Biol. Chem.* 266:20369–20374 (1991)). The $\alpha_2\beta_1$ integrin interacts with collagen and laminin and may be involved in the sealing event necessary for resorption to occur (Horton et al., supra, 1991). An agent such as the RGD peptides of the invention, which can inhibit ligand binding to these and other integrins present on osteoclasts, is useful for disrupting the binding of osteoclasts to bone and, therefore, reducing or inhibiting the process of bone resorption.

The invention provides a method of reducing or inhibiting bone resorption in a subject, comprising administering an RGD peptide as disclosed herein. As used herein, the terms "reducing" and "inhibiting" have their common meanings. The terms are used together, here, to avoid any ambiguity as to the extent to which an RGD peptide of the invention acts. It is recognized, for example, that an RGD peptide can decrease the level of bone resorption below a level that is detectable using a particular assay. In this situation, one would be unable to determine whether the rate of bone resorption was reduced to a lower level or inhibited such that no resorption was occurring. The use of these terms together precludes the need to distinguish these events.

The peptides of the invention also can alter $\alpha_V\beta_3$ integrin receptor binding. As used herein, the term "alter" is used in its broadest sense to indicate an increase or decrease in binding. For example, when present in solution, the peptides of the invention can decrease $\alpha_V\beta_3$ binding to a ligand by competing with the ligand for the integrin receptor. A peptide of the invention also can be attached to a solid substrate, which can then increase binding of the $\alpha_V\beta_3$ receptor to the substrate.

Integrin-ligand binding can be inhibited and binding can be disrupted by synthetic peptides comprising the RGD sequence (see, for example, U.S. Pat. No. 4,614,517 issued Sep. 30, 1986; U.S. Pat. No. 4,792,525 issued Dec. 20, 1988; U.S. Pat. No. 4,988,621 issued Jan. 29, 1991, each of which is incorporated herein by reference). RGD-containing peptides have been shown to block osteoclast adhesion in vitro (Horton et al., *J. Bone Miner. Res.* 8:239–247 (1993)). Echistatin is a natural RGD-containing protein that is isolated from snake venom. Echistatin binds to osteoclasts in a nonselective manner and inhibits bone resorption in vitro (Sato et al., *J. Cell Biol.* 111:1713–1723 (1990); EP 437,367) and in vivo (Fisher et al., *Endocrinology* 132:1411–1413 (1993).

The potency and selectivity of an RGD peptide toward an integrin receptor can be improved by restricting the number of conformations the peptide can adopt (Pierschbacher and Ruoslahti, *J. Biol. Chem.* 262:17294–17298 (1987); WO 89/05150). Conformational restraint of a peptide can be induced by various means including, for example, cyclization. The concept of using cyclic RGD peptides, modeled after echistatin, to inhibit osteoclast attachment to bone has been broadly described (EP 437,367), and osteoclast attachment inhibiting activities of several cyclic RGD peptides have been reported (Bertolini et al., In *13th Ann. Mtg. Am. Soc. Bone Miner. Res.*, abstract 252 (1991); Horton et al., supra, 1993).

In one aspect, an RGD peptide useful as a therapeutic for unwanted bone resorption is receptor selective in targeting only the one or few integrins involved in bone resorption and not others. As a result, an RGD peptide of the invention can preferentially inhibit, for example, the binding of osteoclasts, as compared to other cell types, to bone. In another aspect, a therapeutically useful RGD peptide is potent and, therefore, effective at a relatively low dose. A peptide having both potency and selectivity is particularly useful. The present invention provides RGD peptides having one or more of these characteristics and provides methods for evaluating RGD peptides to identify selective and potent peptides and methods of using the RGD peptides of the invention to inhibit bone resorption.

The present invention also provides a series of in vitro and in vivo assays useful for screening a panel of peptides in order to identify peptides that can reduce or inhibit bone resorption or that can affect integrin binding such as $\alpha_V\beta_3$ integrin binding. Such peptides can include, for example, peptides within the pharmacophore groups exemplified herein or peptides within other pharmacophore groups. The series of assays disclosed herein is particularly useful for determining the selectivity and potency of a peptide for reducing or inhibiting bone resorption. The selectivity of a peptide for an integrin receptor involved in osteoclast binding to bone can be determined, for example, using the integrin receptor assays and cell attachment and detachment assays described herein. Use of cell-based assays in conjunction with receptor-based assays is informative because the receptor ELISAs provide useful information regarding the binding characteristics of a particular peptide toward a particular integrin and because the cell-based assays confirm that those characteristics are relevant to the $\alpha_V\beta_3$ receptor or to bone resorption.

A peptide that selectively binds an integrin receptor involved in osteoclast binding to bone and that causes detachment of osteoclasts, but not other cell types, can be identified as a selective peptide and can be further examined for its potency by comparing the IC50 value of the peptide with other peptides. Thus, the disclosed series of assays provides a means for identifying a potent and/or selective peptide, which can reduce or inhibit bone resorption or alter $\alpha_V\beta_3$ binding.

A potent or selective RGD peptide can be administered to a subject such as a human in order to reduce or inhibit bone resorption in the subject. Generally, the subject has a pathology that is characterized by an undesirable balance of bone resorption as compared to bone formation, resulting in excessive bone resorption. An elderly person suffering from osteoporosis is an example of a subject having such a pathology. Other relevant pathologies include, for example, Paget's disease, osteoclastoma and the pathological loss of bone that occurs in an astronaut during a space mission or in a person exposed to a minimal gravity environment. Furthermore, bone loss can occur in a bone that is immobilized in a cast, in a subject restricted to a prolonged period of bed rest and in a subject undergoing kidney dialysis. Administration of an RGD peptide of the invention can reduce or inhibit the rate of bone resorption in each of these subjects. Thus, the peptides of the invention are particularly useful as medicaments, wherein administration of such a peptide to a subject can decrease the amount of bone loss in the subject.

An $\alpha_V\beta_3$ selective peptide of the invention also can be useful in a pathology such as cancer, provided the cancer cell, for example, expresses the $\alpha_V\beta_3$ integrin. Administration of a peptide of the invention to a subject having such a pathology can inhibit attachment of the $\alpha_V\beta_3$ integrin-containing cell to extracellular matrix proteins or other relevant ligands involved in tumor cell metastasis (Nip et al., J. Clin. Invest. 90:1406–1413 (1992); Gladson and Cheresh, J. Clin. Invest. 88:1924–1932 (1991), each of which is incorporated herein by reference). Peptides of the invention that can inhibit $\alpha_V\beta_3$ integrin binding to a ligand and, thus, can be effective in treating a pathology such as cancer are evaluated using methods known in the art and described, for example, by Hardan et al., Intl. J. Canc. 55:1023–1028 (1993); Murthy et al., Clin. Expt. Metast. 10:39–47 (1992); and Komazawa et al., Clin. Expt. Metast. 11:482–491 (1993), each of which is incorporated herein by reference.

The $\alpha_V\beta_3$ integrin also is involved in binding von Willebrand factor (VWF) to endothelial cells. This binding is necessary for maintaining the integrity of the blood vessel wall and permitting new blood vessel formation and blood vessel wall repair (Denis et al., Blood 82:3622–3630 (1993)). $\alpha_V\beta_3$ receptor selective peptides can be used to strengthen attachment of endothelial cells to vessel walls or to inhibit the interaction of an endothelial cell and VWF. Similarly, angiogenesis depends on interactions between endothelial cells and $\alpha_V\beta_3$ integrins (Brooks et al. Science 264:569–571 (1994)). Pathologies such as diabetic retinopathy, rheumatoid arthritis and cancer can result due to pathologies affecting these interactions. Thus, peptides that are selective for binding to the $\alpha_V\beta_3$ integrin can bind $\alpha_V\beta_3$ and block its binding to a ligand. Such selective binding by a peptide of the invention can provide a means of treating an $\alpha_V\beta_3$-related pathology.

Peptides selective for binding to $\alpha_V\beta_3$ also can affect binding to the $\alpha_{IIb}\beta_3$ integrin, which is involved in platelet aggregation. For example, the peptide RGD(YOMe)RE-NH$_2$ (SEQ ID NO: 67) has an IC$_{50}$ value of 0.0035 $\mu$M in an $\alpha_V\beta_3$ ELISA and is highly potent at inhibiting platelet aggregation (IC$_{50}$=0.08 $\mu$M). Thus, an $\alpha_V\beta_3$ selective peptide also can be useful, for example, for treating or diagnosing a pathology involving the $\alpha_{IIb}\beta_3$ receptor. Similarly, peptide ligands for the $\alpha_{IIb}\beta_3$ receptor can be useful for inhibiting bone resorption. Assays useful for evaluating the reactivity of a peptide with $\alpha_{IIb}\beta_3$, including whether the peptide can inhibit platelet aggregation, are known in the art and described, for example, in WO91/15515, which is incorporated herein by reference.

The in vitro assays disclosed in Example II also can used to identify receptor selective peptides of the invention that have various specific in vitro and in vivo utilities. For example, a receptor selective peptide of the invention can be attached to a supporting matrix such as a natural or synthetic surface. Such a peptide coated surface can be useful for separating in vitro a population of cells that express a specific receptor from cells that do not express the receptor. For example, a peptide that selectively binds $\alpha_V\beta_5$, but not $\alpha_5\beta_1$ or $\alpha_V\beta_3$, can be used to isolate a population of normal articular chondrocytes, which primarily express $\alpha_V\beta_5$ integrin receptors, from cells that express $\alpha_V\beta_3$ and/or $\alpha_5\beta_1$ integrins.

Various receptor selective peptides are disclosed herein or can be identified using the methods in Example II. For example, peptide 214 has higher affinity for $\alpha_V\beta_3$ and $\alpha_5\beta_1$ than for $\alpha_V\beta_5$. Thus, peptide 214 can bind with greater affinity a cell such as an osteoclast, which expresses $\alpha_V\beta_3$, as compared to a cell that expresses $\alpha_V\beta_5$ receptors. Similarly, peptides 825, 390 and 310 are more selective toward $\alpha_5\beta_1$ than toward $\alpha_V\beta_5$ and can be useful to isolate a population of cells expressing an $\alpha_5\beta_1$ receptor.

The receptor selectivity of a peptide of the invention also can be used advantageously in vivo. For example, a peptide coated matrix as described above can be implanted into a subject in order to facilitate localization of cells expressing a specific integrin receptor at the implant site. For example, peptide 214 as described above can be useful for inducing the localization of osteoclasts at a site of bone hypertrophy as occurs in a pathology such as senile ankylosing hyperostosis of the spine. In addition, peptides 825, 390 and 310, as described above, can be useful for inducing $\alpha_5\beta_1$-mediated fibronectin matrix assembly, for example, in a wound. In addition, the peptides of the invention can be administered to a subject in soluble form and, therefore, can be useful for preventing, if desired, $\alpha_5\beta_1$-mediated fibronectin matrix assembly in a wound in order to prevent, for example, excessive scarring. Thus, the receptor selectivity of the disclosed peptides as shown, for example, in FIG. 2 defines various utilities for the specific peptides.

The invention provides pharmaceutical compositions comprising an RGD peptide of the invention, which can reduce or inhibit bone resorption or alter $\alpha_v\beta_3$ binding, and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters. A peptide of the invention also can be encapsulated within a biodegradable or non-biodegradable polymer.

A pharmaceutically acceptable carrier can contain physiologically acceptable compounds that act, for example, to stabilize an RGD peptide of the invention or to increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the RGD peptide and on the particular physicochemical characteristics of the specific peptide.

One skilled in the art would know that a pharmaceutical composition comprising an RGD peptide of the invention can be administered to a subject having pathologically elevated bone resorption as compared to bone formation by various routes including, for example, orally or parenterally, such as intravenously, intramuscularly, subcutaneously or intraperitoneally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or solution, or active, for example, using a nasal spray or inhalant. A pharmaceutical composition comprising an RGD peptide of the invention also can be administered as a topical spray, in which case one component of the composition can be an appropriate propellant. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to reduce or inhibit bone resorption in a subject or to alter $\alpha_v\beta_3$ or other integrin binding, an RGD peptide of the invention must be administered in an effective dose, which is about 0.01 to 100 mg/kg body weight. As used herein, the term "effective dose" means a dose that can reduce or inhibit bone resorption in a subject. An effective dose can be determined using methods known to those in the art, including the methods described in Examples II and III, below. The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an RGD peptide of the invention required to obtain an effective dose in a subject depends on many factors including the age and general health of the subject as well as the route of administration and the number of treatments to be administered. In view of these factors, the skilled artisan would adjust the particular dose so as to obtain an effective dose for reducing or inhibiting bone resorption.

An RGD peptide of the invention is useful for reducing or inhibiting osteoclast binding to a matrix in vitro. As generally described in U.S. Pat. Nos. 4,614,517, 4,792,525 and 4,988,621, supra, RGD-containing peptides in solution bind to integrins that are expressed on the surface of a cell and either prevent the cell from attaching to a matrix or effect detachment of the cell from a matrix. In addition, when RGD-containing peptides are coated onto a surface, a cell that expresses an integrin reactive with the peptide can bind to the surface. Thus, the peptides of the invention can be used to alter the ability of a cell expressing an integrin to attach to a solid matrix such as a tissue culture plate, a prosthetic device or an artificial extracellular matrix (see, for example, WO 90/06767, which is incorporated herein by reference). Since peptides of the invention also can demonstrate receptor selectivity, they are particularly useful for inhibiting the binding of a cell expressing the integrin to such a matrix.

The following examples are intended to illustrate but not limit the present invention.

EXAMPLE I

Synthesis of RGD Peptides

This example provides methods for chemically synthesizing the RGD peptides of the invention.

A. Synthesis of cyclic peptides having disulfide bonds

Peptides were synthesized by the solid-phase method utilizing an automated synthesizer (Applied Biosystems, Inc. Model 431A) (see Steward and Young, In *Solid Phases Peptide Synthesis*, 2nd ed. (Pierce Chemical Co., Rockford, Ill., 1984), which is incorporated herein by reference). Peptides having a C-terminal amide were synthesized using p-methylbenzhydrylamine (pMBHA) resin. Peptides having a C-terminal acid were synthesized using chloromethylated resin. Peptides having an N-terminal acetyl group were acetylated using a mixture of acetic anhydride (20 eq) and diisopropylethylamine (20 eq) in N-methylpyrrolidone.

N-terminal tertbutyloxycarbonyl (Boc) protection was employed for all amino acids. Boc-Arg(Tos)-OH, Boc-Asp(OcHx)-OH, Boc-Cys(4-MeBzl)-OH, Boc-Gly-OH, Boc-Hpa-OH, Boc-Lys(CZ)-OH, Boc-Pen(4-MeBzl)-OH, Boc-(D)Pen(4-MeBzl)-OH, Boc-Pro-OH, Boc-Tic-OH, Boc-7-OMe-Tic and Boc-Tyr(Me)-OH were purchased from Bachem Inc. (Torrance, Calif.). The following compounds were synthesized using the methods described in the indicated references: Boc-Idc-OH (Sancy, In *Organic Syntheses* 63:160–170 (1984)); Boc-Dic-OH (Martin et al., EP 432, 695); Boc-OiC-OH (Vincent et al., *Tetrahed. Lett.* 23:1677–1680 (1982)); and Boc-Tca-OH (Yabe et al., *Chem.*

*Pharm. Bull.* 26:993–997 (1978), each of which is incorporated herein by reference). Dicyclohexylcarbodiimide and hydroxybenzyltriazole were used in the coupling reactions. The extent of the reactions was monitored using the standard ninhydrin test.

Following synthesis, the peptides were removed from the resin and deprotected by adding anhydrous hydrogen fluoride (HF; 10 ml/g of resin-bound peptide) containing anisole (1 ml/g) at 0° C. for 60 min. The HF was removed by evaporation and the residue was washed with anhydrous ether. The crude peptides were extracted with water or 15% aqueous acetic acid and the aqueous fractions were combined and lyophilized. Peptides were purified and characterized as described below.

The crude acyclic peptide was dissolved in 0.1M ammonium bicarbonate (0.5 mg/ml) and stirred uncovered. The course of the reaction was monitored by HPLC. After cyclization was complete (several hours to several days), the solution was filtered and the peptides were purified and characterized as described below.

B. Synthesis of cyclic peptides having lactam bridges

Cyclic peptides having a lactam bridge were synthesized as outlined herein. The protected peptide resin was synthesized using the pMBHA resin. The lactam bridge was formed while the peptide was on the resin using the method described by Felix et al., *Int. J. Pept. Prot. Res.* 31:231 (1988) and by Felix et al., *Int. J. Pept. Prot. Res.* 32:441 (1988), each of which is incorporated herein by reference.

Essentially, the method of Felix et al. uses $N^\alpha$-Boc-amino acids together with 9-fluorenylmethyl ester (OFm) side-chain protection. Asp and Glu were introduced using Boc-Asp(OFm)-OH and Boc-Glu(OFm)-OH. After coupling the final amino acid, OFm protecting groups were selectively removed by treating the peptide resin with 50% piperidine in dimethylformamide for 1 hr. The peptide resin was washed with 3×40 ml dichloromethane and mixed with a 6-fold excess of BOP reagent (benzotriazol-1-yl-oxy-tris-(dimethylamino)phosphonium hexafluorophosphate) in the presence of an 8-fold excess of diisopropylamine for 5 hr. Coupling reactions were repeated until the resin gave the negative ninhydrin test.

After the cyclization reaction was complete, peptides were removed from the resin and deprotected using anhydrous HF (10 ml/g of resin-bound peptide) containing anisole (1 ml/g) at 0° C. for 60 min. The HF was removed by evaporation and the residue was washed with anhydrous ether. The crude peptides were extracted with water or 15% aqueous acetic acid and the aqueous fractions were combined and lyophilized and purified and characterized as described below.

C. Purification and Characterization of the Peptides

The crude peptides were purified via preparative RP-HPLC on a $C_{18}$ silica gel column (Waters "DELTA-PAK," column 15 μm, 300A, 47×300 mm) eluting with a linear acetonitrile gradient (0–30%) with a constant concentration of trifluoroacetic acid (TFA; 0.1%, v/v) over 30 min at a flow rate of 40 ml/min. The purified peptides were analyzed by analytical RP-HPLC using a C-18 column (Vydac, 5 μm, 300A, 4.5×250 mm). The purified peptides were recovered by lyophilization of the HPLC fractions and were at least 95% pure. For analytical HPLC, a binary solvent system, water containing 0.1% TFA and acetonitrile containing 0.1% TFA as the organic modifier, was used. The solvent programs involved linear gradients as follows: (1) 10–45% acetonitrile over 35 min with a flow rate of 1.5 ml/min and (2) 0–70% acetonitrile over 30 min with flow rate of 1.5 ml/min.

In some cases, the peptide was adjusted to a neutral pH and potassium ferricyanide was added to the TFA peptide to minimize polymerization that might result due to the presence of the reducing agent. The potassium ferricyanide was removed by ion exchange chromatography and the peptides were lyophilized. The presence of thiol reducing agents, which indicates the need to add potassium ferricyanide, can be detected using Ellman's test (*Arch. Biochem. Biophys.* 82:70 (1959), which is incorporated herein by reference).

To confirm the correct amino acid sequences as shown in FIGS. 2 and 3 were synthesized, the peptides were characterized by fast atom bombardment mass spectroscopy and by amino acid analysis. Amino acid analysis was performed on a Pickering Labs-Trione amino acid analyzer that was equipped with spectra-physics UV detector. Hydrolysis of peptide samples for amino acid analysis was performed on 1 mg samples with 1 ml constant boiling 6N HCl. Samples were degassed, sealed under vacuum and heated for 24 hr at 110° C.

D. Synthesis of β-[(methylsulfonyl)amino]alanine

β-[(methylsulfonyl)amino]alanine (Maa) was synthesized using the general procedure of Krchnak et al., *Collection Czechoslov. Chem. Commun.* 44:2161–2164 (1979), which is incorporated herein by reference). To a stirred solution of $N^\alpha$-tertbutyloxycarbonyl-α,β-diaminopropionic acid (700 mg, 3.43 mmol) in 1N NaOH (34 ml) was added a solution of methanesulfonylchloride (530 μl, 6.86 mmol) in acetone (30 ml). After 1 hr, the reaction was extracted 2× with ether and acidified to pH 2 using 1N HCl. The aqueous phase was extracted 3× with ethyl acetate and the combined organic phases were dried ($MgSO_4$) and concentrated to produce an oil.

β-[(methylsulfonyl)amino]alanine was purified by silica gel chromatography using ethyl acetate/ethanol/acetic acid (95.8:4:0.2) as eluant. 300 mg β-[(methylsulfonyl)amino]alanine was obtained and was used in the standard solid phase peptide synthesis protocol. $^1$H-NMR analysis: (MeOH, $D_4$; 300 MHz) 4.2 ppm; (m, 1H). 3.3–3.6 ppm; (m, 2H). 2.95 ppm; (s, 3H). 1.4 ppm (s, 9H).

EXAMPLE II

RGD Peptide Activity In Vitro

This example describes a series of assay useful for determining the activity of an RGD peptide for inhibiting bone resorption, including inhibiting the binding of an osteoclast to a matrix in vitro.

A. Preparation of Assay Reagents

1. Isolation of human vitronectin

Human plasma was clotted by adjusting the sample to 20 mM $CaCl_2$, then stirring for 1 hr at room temperature (RT), followed by 2 hr at 4° C. The plasma was fractionated by centrifugation at 3000 rpm for 15 min ("SORVALL" centrifuge with GS3 rotor) and the supernatant was retained.

The supernatant was adjusted to 1 mM phenylmethylsulfonyl fluoride (PMSF)/5 mM EDTA. A column containing 75 ml "SEPHAROSE CL-4B" Cross-Linked beaded agarose (Pharmacia; Piscataway N.J.) was equilibrated using five column volumes (5 vol) phosphate buffered saline (PBS), the supernatant was added and the flow-through fraction was collected. The flow-through fraction was applied to a column containing 50 ml heparin-Sepharose, which was made by swelling heparin-"SEPHAROSE CL-6B" Cross-Linked beaded agarose (Pharmacia) with PBS for 5 min in a sintered glass funnel, then washing with PBS for 15 min. The heparin-"SEPHAROSE" beaded agarose was poured into a column, washed with 3 vol Buffer B (5 mM EDTA, 2M NaCl, 10 mM sodium phosphate, pH 7.7) and equilibrated with 5 vol PBS. The dye-colored flow-through fraction was collected, solid urea was added to a final concentration of 8M and the sample was incubated with stirring for 2 hr at RT.

The heparin-"SEPHAROSE" beaded agarose column was washed with at least 3 vol Buffer C (5 mM EDTA, 8M urea, 10 mM sodium phosphate, pH 7.7, 10 mM 2-mercaptoethanol, 2M NaCl) and equilibrated with 5 vol Buffer A (5 mM EDTA, 8M urea, 10 mM sodium phosphate, pH 7.7). The flow-through fraction from above was loaded onto the column. The column was washed with 3 vol Buffer A, followed by 3 vol Buffer A containing 140 mM NaCl and by 1 vol Buffer A containing 140 mM NaCl/10 mM 2-mercaptoethanol. After 2 hr, the column was washed with 3 vol of the same final buffer.

Vitronectin (Vn) was eluted using Buffer D (Buffer A containing 0.5M NaCl). The fractions were evaluated by 8% sodium dodecyl sulfate polyacrylamide gel electrophoresis (SDS-PAGE) under non-reducing conditions. The presence of Vn was confirmed by identifying the characteristic 65 kilodalton (kDa) and 75 kDa bands. In some instances, Vn was confirmed by western blot analysis using a specific anti-Vn antibody (8Eb; Hayman et al., *Proc. Natl. Acad. Sci., USA* 80:4003–4007 (1983), which is incorporated herein by reference). Western blot analysis was performed using a standard method as described, for example, by Sambrook et al., *Molecular Cloning: A laboratory manual* (Cold Spring Harbor Laboratory Press 1989), which is incorporated herein by reference.

2. Isolation of human fibronectin

Frozen human plasma was thawed at RT, then adjusted to 100 μM PMSF. The plasma was fractionated by centrifugation at 3000 rpm for 15 min in a "SORVALL" centrifuge (GS3 rotor) and the supernatant was collected.

A column containing 300–500 ml "SEPHAROSE 4B" beaded agarose was equilibrated with 1 l Buffer E (8 g KCl, 8 g $KH_2PO_4$, 320 g NaCl, 86.8 g $NaH_2PO_4$ per liter). The plasma supernatant was added to the column and the flow-through was collected from the time the yellow-colored plasma enters the "SEPHAROSE" Cross-Linked beaded agarose until the time the eluate became clear. Two vol Buffer E were added to the column as a wash buffer to "push" the plasma through the column.

A column containing 50 ml gelatin Sepharose 4B was prepared in a Kontes column and equilibrated with 500 ml Buffer E. The flow-through from the Sepharose 4B column was loaded at a rate of 2 ml/min or slower. The column was washed with 500–1000 ml Buffer E or until $OD_{280}$ was below 0.10.

Three to five vol Buffer F (0.05M Tris, 4.5M urea, pH 7.0) were used to elute plasma fibronectin (Fn). One-quarter column vol fractions were collected and evaluated by 8% SDS-PAGE under reducing conditions. The presence of Fn was confirmed by identifying the characteristic band migrating at approximately 210–250 kDa. In some cases, the presence of Fn was confirmed by western blot analysis using a specific anti-Fn antibody (3E1; Pierschbacher et al., *Cell* 26:259–267 (1981), which is incorporated herein by reference).

Peak fractions containing Fn were pooled and the optical density was measured. If necessary, the pooled fraction was diluted until an $OD_{280}$ reading corresponding to 1 mg/ml Fn was obtained. The sample then was dialyzed against PBS and stored at −20° C. in PBS in a non-frost free freezer.

3. Preparation of 110 kDa fibronectin fragment

Fibronectin was purified as described above and dialyzed against 3 changes of 100 vol Buffer G (0.05M Tris, 0.3M NaCl, pH 8.3–8.5). The urea concentration decreased to below 0.1M.

Chymotrypsin was added at a concentration of 0.001 mg chymotrypsin/mg Fn. The digestion mixture was incubated overnight at 4° C. with gentle rocking. The presence of complete digestion was confirmed by SDS-PAGE analysis of pre- and post-digestion samples. The digested Fn sample was dialyzed against 2 changes of 100 vol Buffer H (0.1M $NaHCO_3$, 0.5M NaCl, pH 8.0). The pH of the dialyzed digest was between pH 8–9.

4. Purification of human $\alpha_V\beta_5$ vitronectin receptor (VnR)

Human placenta was homogenized and washed on ice in 225 ml of Tris-buffered saline (TBS; pH 7.4–7.5; 4° C.), then fractionated by centrifugation at 3000 rpm for 15 min at 4° C. The supernatant was discarded and the pellet was extracted with 225 ml TBS containing 100 mM octylglucopyranoside (OG). Extraction was performed at 4° C., on ice, for 30 min, with stirring every 10 min. The extract was fractionated by centrifugation at 3000 rpm for 20 min and the supernatant was collected. The supernatant, which contained the $\alpha_V\beta_5$ Vn receptor (VnR), was adjusted to 3 mM $CaCl_2$.

Two tandem Kontes (Fisher Scientific) columns were prepared using equal volumes of Sepharose 4B or 6B. Both columns were equilibrated with 10 vol cold (4° C.) Buffer I (1×TBS, pH 7.4, 50 mM OG, 3 mM $CaCl_2$, 20 μg/ml PMSF). One column contained Vn (Vn column) and was prepared as follows. Vn was dialyzed against 2 to 3 changes of coupling buffer (0.1M $NaHCO_3$, 0.5M NaCl, pH 8.3). CNBr-"SEPHAROSE" Cyanogen bromide-activated beaded agarose was swelled in 1 mM HCl, washed with coupling buffer, then combined with Vn. Coupling proceeded for 2 hr at RT or overnight at 4° C., followed by blocking with 1M ethanolamine or 0.2M glycine (pH 8.0) for 2 hr at RT.

The filtered, calcium supplemented placental extract was loaded onto the "SEPHAROSE" cross-linked beaded agarose column, then run through the Vn column at 4° C. The flow-through was collected in a polypropylene container for disposal. The Vn column was washed with 5 vol cold (4° C.) Buffer I, allowed to equilibrate to RT, then washed with another 5 vol Buffer I at RT. The column was slowly eluted with 3 vol Buffer J (1×TBS, pH 7.4, 50 mM OG, 100 μg/ml GRGDSP (SEQ ID NO: 4) peptide, 20 μg/ml PMSF). Fractions were collected and evaluated by 8% SDS-PAGE under non-reducing conditions. Fractions showing bands migrating at the characteristic 150, 145 and 90 kDa molecular mass of the VnR were pooled, dialyzed against TBS (pH 7.5) containing 50 mM OG/3 mM $CaCl_2$ and concentrated using an "AMICON" YM 30 filter.

5. Purification of human $\alpha_5\beta_1$ fibronectin receptor (FnR)

Fibronectin receptor (FnR) was purified from 100 mM octyl-glucopyranoside-extracted human placenta. The procedure for purifying the FnR was the same as described for purifying the VnR through the initial Sepharose chromatography step. Then, for purifying the FnR, the "SEPHAROSE 4B" beaded agarose column flow-through was adjusted to 3 mM $Mn^{2+}$ and the resulting solution was fractionated using affinity chromatography on columns containing a GRGDSPK (SEQ ID NO: 5) peptide and the 110 kDa fibronectin fragment. Column washes and elutions were the same as described for purifying VnR, except that $MnCl_2$ rather than $CaCl_2$ was included in the wash buffer.

Briefly, an unmodified "SEPHAROSE 4B" beaded agarose column was equilibrated with 5 vol cold (4° C.) Buffer K (TBS, pH 7.5, 50 mM octylglucoside, 3 mM $CaCl_2$). The flow through was collected and adjusted to a final concentration of 3 mM $CaCl_2$. A GRGDSPK-"SEPHAROSE" cross-linked beaded agarose (SEQ ID NO: 5) affinity column (20–40 ml) was prepared using the method for preparing the Vn column, above, except that lyophilized GRGDSPK (SEQ ID NO: 5) was suspended in the coupling buffer and the sample was not dialyzed. The column was equilibrated with 200–400 ml Buffer K and placental extract was applied. The flow-through fraction was collected and adjusted to 6 mM $MnCl_2$.

The 110 kDa Fn fragment-"SEPHAROSE" beaded agarose column was prepared as described for the Vn column. The column was preequilibrated with 5 vol cold Buffer L (TBS, pH 7.5, 50 mM octylglucoside, 3 mM $MnCl_2$), the extract was applied and the flow-through fraction was collected. The column was washed with 5 vol cold Buffer L, allowed to come to RT (about 30 min), then another 5 vol Buffer L at RT was added. When the $OD_{280}$ of the flow through was below 0.02, FnR was eluted using 3 vol Buffer M (TBS, pH 7.5, 50 mM octylglucoside, 10 mM EDTA) at RT and one-quarter column volume fractions were collected. The fractions were evaluated by 8% SDS-PAGE under non-reducing conditions and fractions exhibiting bands migrating at the characteristic 155 kDa and 110 kDa molecular masses of FnR (Hemler, *Ann. Rev. Immunol.* 8:365–400 (1990), which is incorporated herein by reference) were pooled, dialyzed into TBS (pH 7.5) containing 50 mM octylglucoside/3 mM $MnCl_2$ and concentrated using an Amicon YM 30 filter.

6. Purification of human $\alpha_V\beta_3$ vitronectin receptor

The $\alpha_V\beta_3$ receptor was purified from octylglucopyranoside-extracted human placenta prepared as described in Example II.4., above. Two tandem Kontes (Fischer Scientific) columns were prepared using equal volumes of "SEPHAROSE 4B" beaded agarose or "SEPHAROSE 6B" beaded agarose. The peptide VTRGDVFTK (SEQ ID NO: 6) was coupled to one column using the method described in Example II.5., above (peptide column). The other column was not modified (plain column). Both columns were equilibrated with 5 vol cold (4° C.) Buffer N (1×TBS, 50 mM octylglucoside, 3 mM $MnCl_2$).

The placental extract was applied to the plain column and the flow through was applied to the peptide column. Following application of the flow through, the peptide column was washed with 10–15 vol Buffer N; half the washes were conducted at 4° C. and half were at RT. Elution was with 4 vol Buffer O (1×TBS, 50 mM octylglucoside, 10 mM EDTA) and ¼ vol fractions were collected. The fractions were evaluated on 8% SDS-PAGE under non-reducing conditions. Fractions containing bands migrating at the characteristic apparent 150 kDa and 90 kDa molecular masses of the $\alpha_V\beta_3$ receptor were pooled and dialyzed overnight against 20 mM Tris (pH 8.0), 34.5 mM octylglucoside, 2 mM $CaCl_2$, and 2 mM $MgCl_2$.

The dialyzed receptor was loaded onto a "MONO-Q" quaternary amine column (HR 5/51; Pharmacia). The pumps were washed with a gradient of Buffer A, and B, before sample loading. Buffer $A_1$ is 20 mM Tris, pH 8.0, 34.5 mM octylglucoside, 2 mM $CaCl_2$, 2 MM $MgCl_2$; Buffer $B_1$ is Buffer $A_1$ containing 1M NaCl. Both buffers were filtered and degassed prior to adding octylglucoside.

The sample was loaded onto the sample loop (valve 1.1, 1 ml/min, 0% B) and injected onto the column (valve 1.2). One ml fractions were collected at 0.05 or 0.1 absorbance units. The appropriate fractions were run on SDS-PAGE and fractions containing $\alpha_V\beta_3$ integrin were pooled and dialyzed against TBS and 50 mM octylglucoside. The integrin was concentrated using an "AMICON" YM 30 filter.

7. Preparation of recombinant human osteopontin

Human osteopontin was produced in CHO cells using standard recombinant DNA methods (see, for example, Sambrook et al., supra, 1989). Plasmid pBS/OP (Young et al., *Genomics* 7:491–502 (1990), which is incorporated herein by reference), which contains the cDNA sequence encoding human osteopontin, was digested with XhoI, then treated with DNA polymerase (Klenow) and dinucleotide triphosphates to generate blunt ends. The plasmid was digested with XbaI and the approximately 1493 bp fragment containing the osteopontin cDNA insert was purified by electrophoresis on a 0.8% agarose gel.

Plasmid PRC/CMV (Invitrogen; San Diego Calif.) was digested with BstXI and treated with DNA polymerase (Klenow) and dinucleotide triphosphates to generate blunt ends. The plasmid was digested with XbaI and the linearized vector was purified on a 0.8% agarose gel. The 1493 bp osteopontin cDNA was ligated with the linearized vector to produce the human osteopontin expression vector, hOP/PRC/CMV, which exhibited a 1900 bp band following digestion with BamHI and electrophoresis in a 0.9% agarose gel.

Approximately 10 μg purified hOP/PRC/CMV DNA was cotransfected with 1 μg pSV2-dhfr into 80% confluent CHO cells (ATCC CRL 9096) (Subramani et al., *Mol. Cell. Biol.* 1:854–864 (1981), which is incorporated herein by reference). Positive transfectants were grown in the presence of methotrexate and selected on the basis of dhfr expression. Recombinant human osteopontin was purified from the CHO cell medium by immunoaffinity using rabbit anti-human osteopontin antibody (Telios; San Diego, Calif.) coupled to CNBr-"SEPHAROSE 4B" cyanogen bromide-activated beaded agarose (Pharmacia). Purified osteopontin was analyzed by SDS-PAGE and migrated with an apparent molecular mass of about 72–76 kDa under non-reducing conditions.

B. In Vitro Assays for Determining RGD Peptide Activity

1. Chick cell detachment assay

Peptides were evaluated for their ability to detach osteoclasts from a matrix consisting of serum-coated microtiter plates. In prescreening assays, 5 μM of the various RGD peptides was used to identify RGD peptides that released at least 60% of the osteoclasts from the matrix. For RGD peptides that were in the active range as determined by the prescreen, the concentration of active RGD peptide that resulted in the release of 50% of the osteoclasts (IC50) was determined (see FIG. 4). In general, RGD peptides having an IC50 of 3.0 μM or less were selected for further examination using the assays described below. However, some peptides having IC50 values greater than 3.0 μM also were analyzed.

Osteoclasts were isolated from embryonic chicks using a modification of the methods of Boyde et al., *Br. Dent. J.* 156:216 (1984) and Chambers et al., *Endocrinology* 116:234 (1985), each of which is incorporated herein by reference. Briefly, chick long bones (femur and tibia) were dissected free of soft tissue and minced in prewarmed minimum essential medium (MEM, pH 7.2; Irvine Scientific; Irvine, Calif.) with Earl's salts, supplemented with 10% heat-inactivated fetal calf serum (FCS) and 200 mM glutamine and containing 100 μg/ml streptomycin and 100 IU/ml penicillin. Cells were removed from bone fragments by vigorous shaking in a capped centrifuge tube. Large particulate material was allowed to settle prior to removal of the cell suspension. After repeated agitation of the cells with a large transfer pipette, 100 μl aliquots of cells were added in triplicate to Corning 96 well microtiter plates that had been preincubated for 1 hr with 100 μl of MEM/FCS media.

The cells were incubated for 90 min at 37° C. in an atmosphere containing 10% $CO_2$. Following incubation, the cell layers were carefully washed 2× with 200 μl sterile PBS, then 100 μl of fresh MEM/FCS was added. Peptides were diluted in the same medium and added to each well. The cells were incubated overnight as described above. After 20 to 24 hr, media were aspirated and the cells were fixed in 10% formalin and washed 2× with distilled water to remove nonadherent cells and debris. Cell layers were stained for 5 min using 0.1% crystal violet and multinucleated osteoclasts were counted by light microscopy.

FIG. 2 shows the IC50 values obtained for various RGD peptides and for the naturally occurring protein, echistatin (ECHI), using the chick osteoclast attachment assay (column designated "chick OC detach (FCS)"). FIG. 4 shows the dose response curves for selected RGD peptides.

The chick cell detachment assay also was used to characterize the selectivity of an RGD peptide. The chick cell preparation contains a heterogeneous population of cells, including osteoclasts, osteoblasts, fibroblasts, monocytes and other cell types. A nonselective peptide can inhibit the attachment of these various cell types to the matrix in this assay, whereas a selective peptide according to this invention primarily will inhibit osteoclasts binding.

RGD peptides that are selective for releasing osteoclasts, but not the other cell types, from the matrix were identified by extracting the crystal violet stain from fixed cells and comparing the amount of staining in a control well (no peptide) with the amount of staining following incubation of the cells with an RGD peptide. Crystal violet was extracted using 20% acetic acid and the optical density of the resulting solution was measured in 96 well microtiter plates by spectrophotometry at 562 nm.

Figure 5:
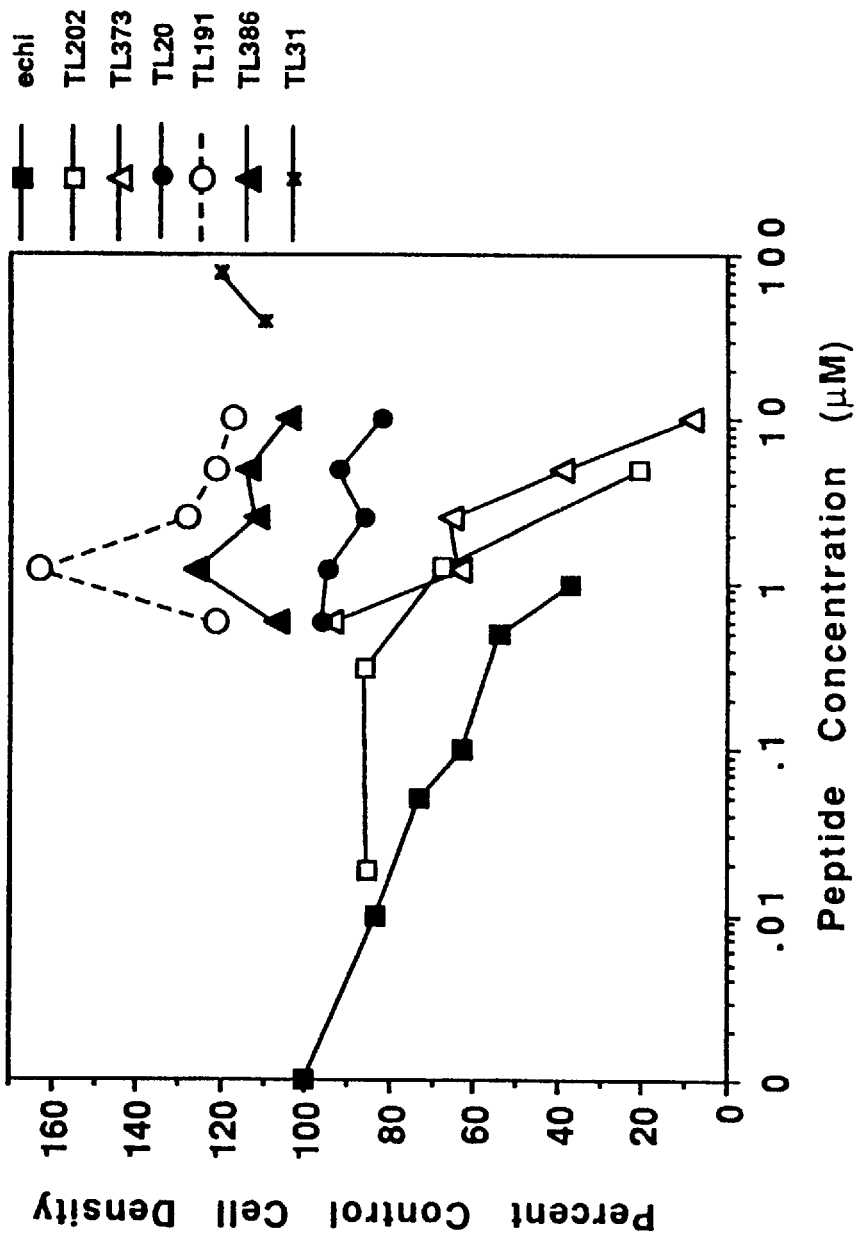
FIG. 5 demonstrates the selectivity of various peptides in the chick total cell detachment assay. A selective peptide produces a curve that is shifted to the right and has a horizontal shape.
Figure 6A:
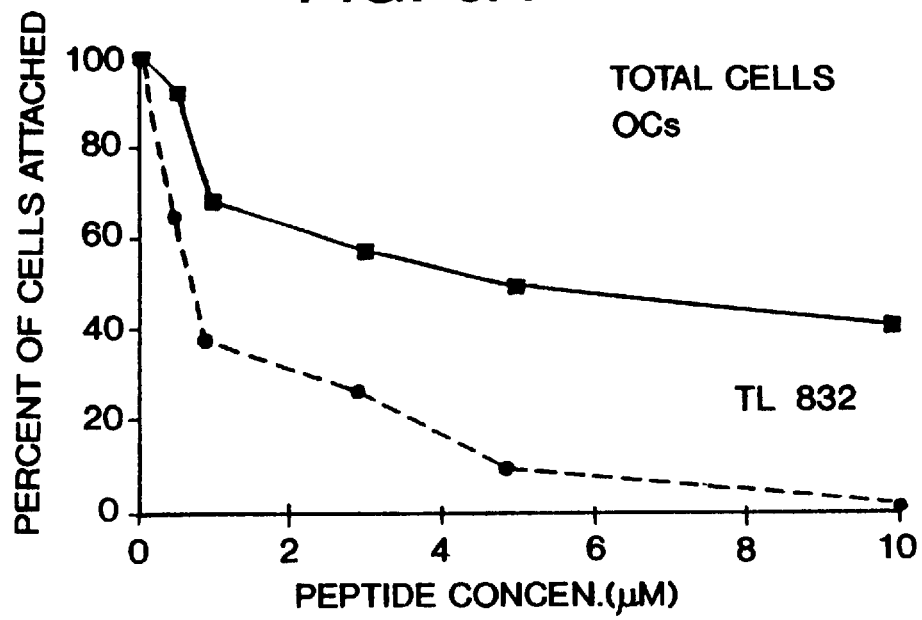
FIG. 6 compares various peptides in both the chick osteoclast detachment assay (OCs) and chick total cell detachment assay (Total Cells). Peptides showing a greater difference in the ability to detach osteoclasts as compared to total cells are considered more selective.
Figure 6B:
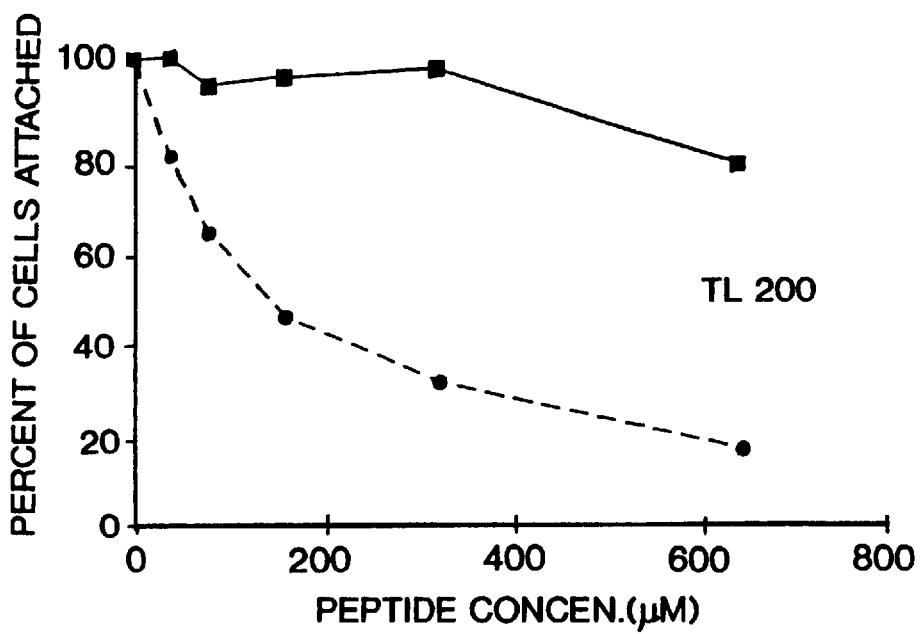
Figure 6C:
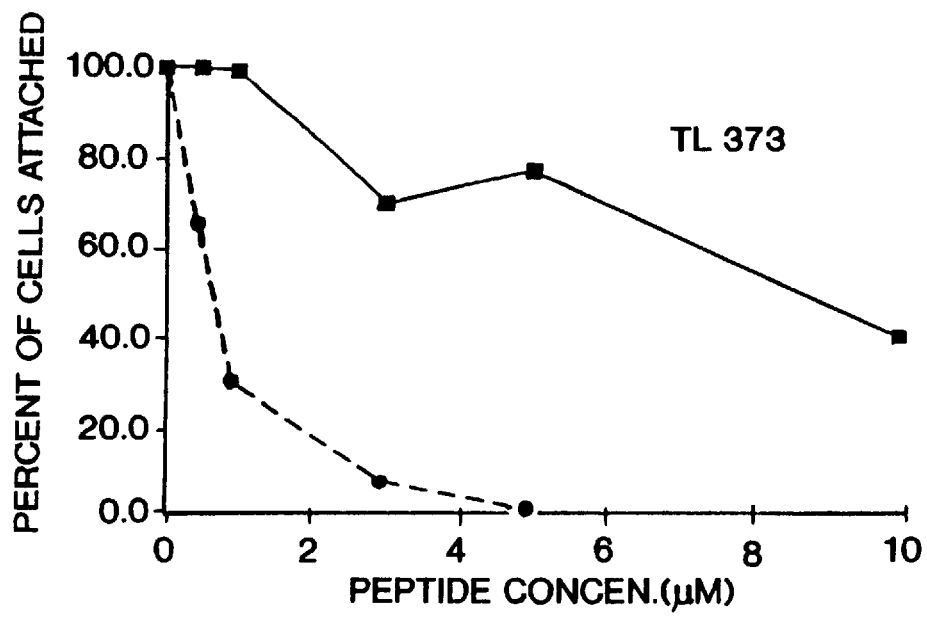
Figure 6D:
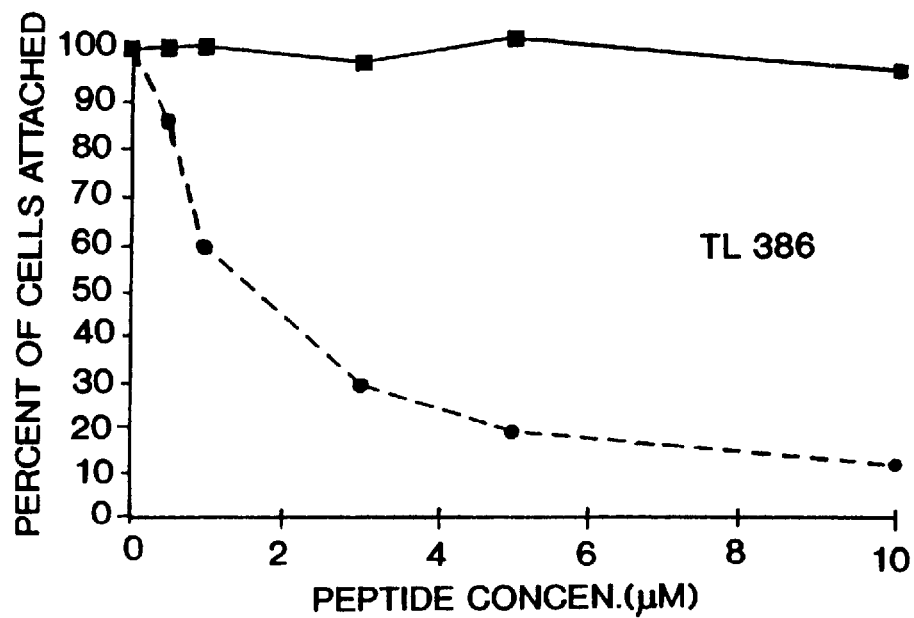

Selectivity of a peptide can be characterized as shown in FIG. 5. A peptide that was relatively nonselective indiscriminately detached an increasing number of cells with increasing dose, yielding a declining percent attachment dose-response curve. In contrast, more highly selective peptides detached primarily osteoclasts and had no additional effect once osteoclasts were detached from the matrix until high concentrations of the peptides were attained. Such a selective peptide yielded a curve that was shifted to the right relative to the nonselective peptides; i.e., much higher concentrations of selective peptides were needed to detach cells other than osteoclasts. As shown in FIG. 5, peptides 386 and 20, for example, yielded a curve that is shifted to the right, which indicates that peptides 386 and 20 caused selective detachment of osteoclasts as compared to other cell types. FIG. 6 provides a different visualization of the cell type selectivity data and shows that increasing concentrations of a peptide can selectively detach osteoclasts, as evidenced by the sharp decline in the percent of attached cells, as compared to other cell types, which are not readily detached.

2. Rat osteoclast bone resorption assay

RGD peptides that were active in the osteoclast detachment assay were evaluated for their ability to inhibit bone resorption. The bone resorption assay further characterizes the potency of an RGD peptide.

Bovine bone femurs were obtained from Pel-Freeze (Rogers, Ariz.). One inch transverse slices were cut using a hand saw and bone plugs were cut on a drill press equipped with a ¼ inch plug cutter. 600 μm thick bone slices were made using a Buehler "ISOMET 2000" diamond saw (Irvine, Calif.). Slices were stored in a 48 well plate containing 10% ethanol.

To remove debris, each slice was sonicated (Fisher 50 "SONIC DISMEMBRATOR") in 10% ethanol and transferred to a sterile 96 well plate. Alternatively, the bovine bone slices were stored and sonicated in PBS, then placed in individual wells of a chamber slide (Lab-Tek; Nunc; Naperville Ill.). 100 μl of a medium containing 10% FCS and 2% streptomycin/penicillin/ glutamine was added to the wells and the plates were incubated at 37° C. for 4 hr.

In addition, tibias, femurs and humeruses were removed from ten or twelve two-day old rat pups (Harlan Sprague, Indianapolis, Ind.) and soft tissue and periosteum was removed. The bones were placed in a petri dish on ice and 3 ml (10 rat pups) or 4 ml (12 rat pups) of medium as above was added. The bones were minced, transferred to a 15 ml conical tube and vigorously shaken for 2 min. The suspension was poured through a 100 μm nylon mesh, which then was washed with 2–5 ml of medium.

In some cases, after transfer to the 15 ml conical tube, the suspension was triturated vigorously for 2 min instead of shaken. The suspension was poured through the 100 μm nylon mesh and 2–5 ml medium was added to the bone fragments remaining in the tube. After 2 min trituration, the suspension was filtered as before.

The cell suspension was agitated using a sterile transfer pipette, medium was removed from the wells containing bovine bone slices and 100 μl of the cell suspension (about $4 \times 10^4$ cells) was added to each well containing a bone slice. Peptides were diluted in PBS, 5 μl of the peptide solution was added to each well and the plates were incubated for 18 to 22 hr at 37 ° C. in an atmosphere containing 10% $CO_2$.

When chamber slides were used, the cell suspensions were added and the samples were incubated for 30 min at 37° C., 12.5% $CO_2$. The cells then were gently removed from the slide chamber, leaving the bone slices in their gasket on the slide. Tweezers were used to remove the bone slices, which were washed in warm medium for 8 sec. The slices were placed into the wells of a 12 well tissue culture plate (Corning; Corning N.Y.) containing various peptide dilutions and incubated for 18–22 hr at 37° C., 12.5% $CO_2$.

Following incubation, the supernatant was aspirated and 0.5% trypsin (1×trypsin-EDTA solution; Irvine Scientific; Santa Ana, Calif.) was added to each well containing a bovine bone slice. After 5 or 10 min, the wells were aspirated and 1% "TRITON X-100" polyoxyethylene ether (Sigma; St. Louis, Mo.) was added to dissolve the cells. The plate was shaken for 1 hr, then each slice was placed in deionized water, sonicated, dehydrated in 70% ethanol for 5 min and air dried. The bone slices were stained with "MILLIPORE"-filtered 1% toluidine blue in 1% sodium borate for 30 sec, then washed 3× with deionized water. "WHATMAN" No. 1 filter paper was used to blot the sample, then the slices were air dried. The number of pits per slice was determined by light microscopy ("LABPHOT-2" microscope, Nikon; Melville, N.Y.). The IC50 value was obtained by comparing the number of pits on a bone slice that was treated with a peptide as compared to an untreated slice. The control is set at 100%, which was at least 15 pits/slice. Active peptides reduce the number of pits/slice.

The results of the bone resorption assay are shown in FIG. 2 (column designated "Rat Bone (Pits)"). A low IC50 value in this assay indicated that a relatively low concentration of the RGD peptide inhibited at least one essential step in bone resorption. RGD peptides that were active in this assay were considered particularly promising candidates for use as a pharmacological agent, since this assay utilizes a mammalian system and measures the ability of a peptide to effect the desired end point of inhibiting bone resorption.

3. Rat osteoclast attachment assay

To determine the effect of a peptide on the attachment of rat osteoclasts in vitro, 100 μl aliquots of the rat pup bone cell suspension described in Example II.B.2., above, were added in triplicate to 96 well "MAXISORP" plates coated with specific substrates or with FCS. Substrate coated plates were used to determine the ability of peptides to inhibit attachment or induce detachment of an osteoclast from a ligand such as vitronectin, fibronectin, osteopontin or collagen I (Collaborative Research), which are ligands present in bone. Substrates were added to 96 well plates (50 $\mu$l of a 5–10 $\mu$g/ml solution in sodium carbonate, pH 9.5) and incubated for 2 hr at 37° C. For FCS control wells, 100 $\mu$l 10% FCS was added. Wells were aspirated, then washed 2×with PBS and blocked with 1% bovine serum albumin in PBS for 2 hr at 37° C. Wells were aspirated and washed again 2× with PBS. Cells were seeded in duplicate at $4\times10^4$ cells/well.

Immediately following addition of the cells, peptides were added to each well and the plates were incubated for 1 hr at 37° C., 10% $CO_2$. Alternatively, peptide was added before cell addition. PBS was aspirated from the precoated wells and 10 $\mu$l of each peptide dilution was added, then 100 $\mu$l of cell suspension (about $4\times10^4$ cells/well) was added. The plate incubated for 1 hr at 37° C., 10% $CO_2$.

Figure 10A:
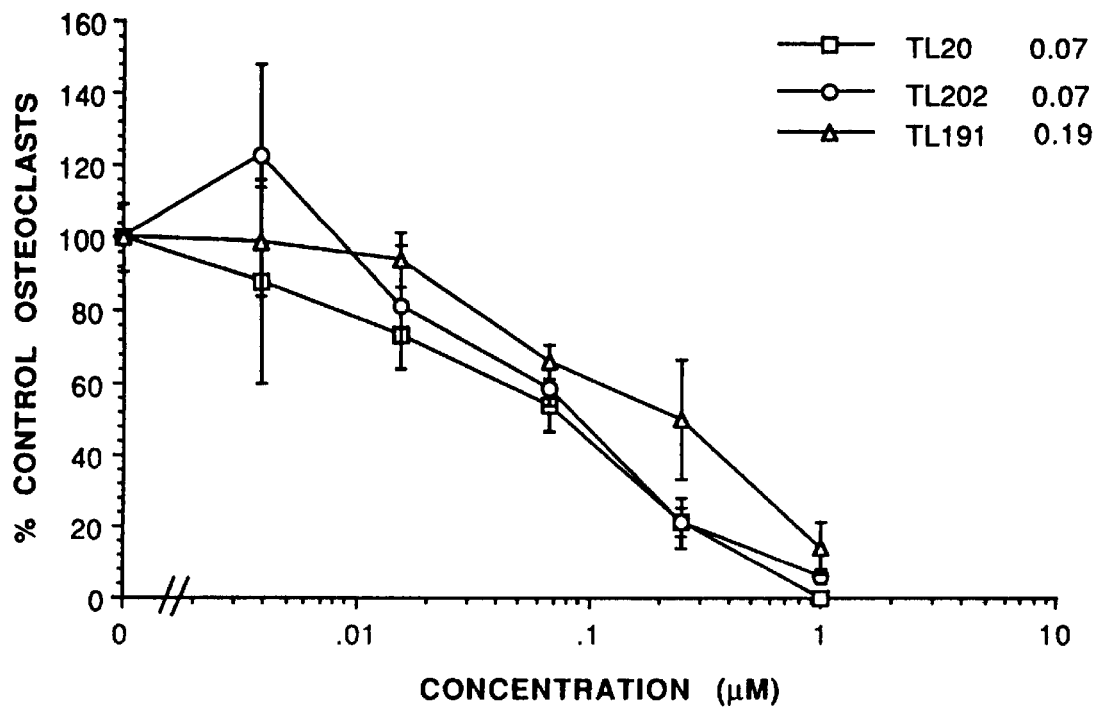
FIG. 10 demonstrates the effectiveness of various RGD peptides of the invention in the rat osteoclast attachment assay using osteopontin or vitronectin as substrate.
Figure 10B:
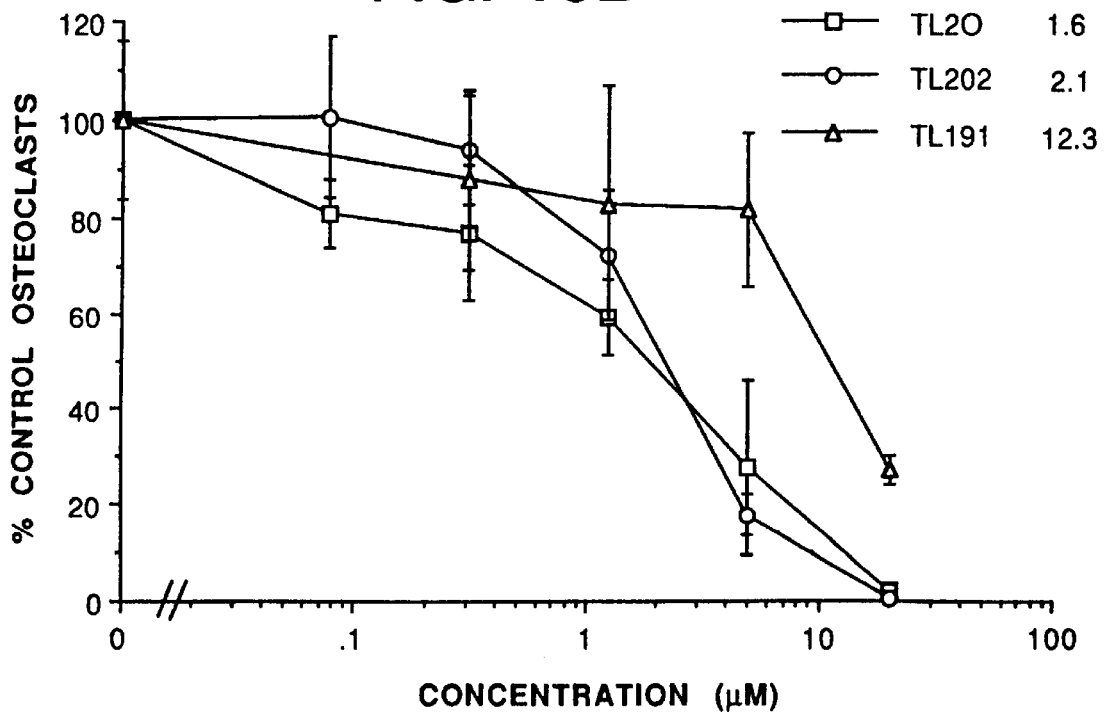
Figure 12:
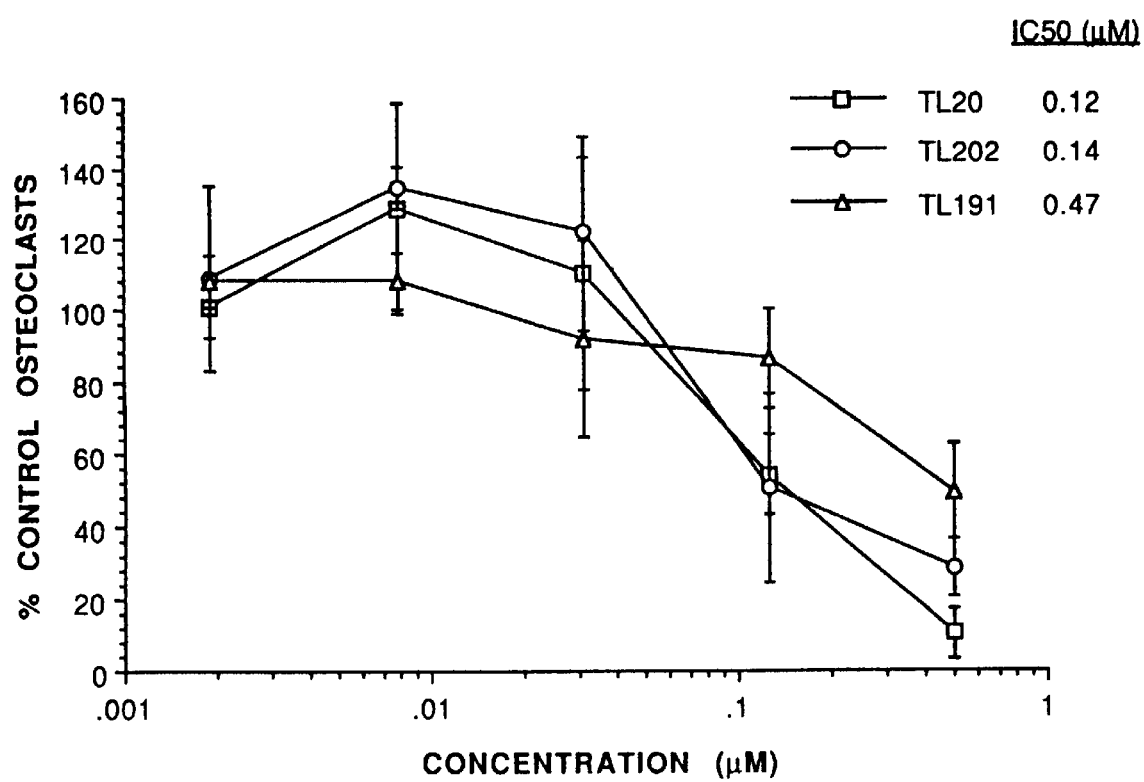
FIG. 12 demonstrates the effectiveness of various RGD peptides of the invention in the rat osteoclast attachment assay using fibronectin as substrate.

Following incubation, the medium and nonadherent cells were removed by aspiration from each well. Cells were fixed in acetone/citrate, washed 2× with distilled water, then stained with 0.1% crystal violet for 5 min. Adherent osteoclasts were counted by light microscopy. The results of these experiments are shown in FIG. 7 (FCS), FIG. 10 (osteopontin and vitronectin), FIG. 11 (collagen) and FIG. 12 (fibronectin).

Adherent osteoclasts also were counted using immunocytochemistry. Following the 1 hr incubation of the cells with the peptides, 200 $\mu$l blocking solution was added to each well and incubated for 1 hr at RT (blocking solution is 10% normal goat serum in 1×TBSC (10×TBSC is 10×TBS, 3 g casein)). Immediately after aspiration, 50 $\mu$l of 0.1 $\mu$g/ml primary antibody was added to the appropriate wells and incubated 1 hr at RT on a shaker. The primary antibody was F-11 (Pharmingen; San Diego Calif.) diluted to 0.1 mg/ml with TBSC adjusted to 1:66 of normal goat serum. The cells then were rinsed in TBST (10×TBST is 200 $\mu$l "TRITON X-100" polyoxyethylene ether and 100 ml of 10×TBS) and the wells were filled with TBST. The wells were allowed to stand for 20 min on the shaker.

Immediately after aspiration of TBST, 50 $\mu$l 1:300 biotinylated goat anti-mouse Ab (Vector; Temecula Calif.) was added to each well. Antibody dilution was in TBSC as above. Incubation and rinsing were as described above for the F-11 antibody, except that the incubation time was 30 min and the shaking rinse time was to 15 min.

After aspiration of the second rinse, an inhibiting solution (10 ml 50% methanol, 400 $\mu$l hydrogen peroxide, 200 $\mu$l sodium azide) was added to each well and allowed to stand for 15 min at RT. The wells were rinsed with water, then filled with water and allowed to stand for 5 min. After aspiration, this rinsing procedure was repeated with 1×TBSABC (90 ml 10×TBS, 20.22 g NaCl, volume adjusted to 1 liter); the second rinse was allowed to stand for 10 min before aspiration.

ABC solution (1:50 avidin solution and 1:50 biotin solution (Vector) in 1×TBSABC; freshly made) was added to each well and incubated for 30 min at RT. The wells were washed with TBSABC and shaken at low speed for 20 min on the shaker. After aspiration, bound antibody was detected using VIP Substrate (Vector) according to the manufacturer's recommendations. After aspiration and air-drying, adherent osteoclasts were counted by light microscopy.

Mammalian osteoclasts primarily express $\alpha_V\beta_3$, $\alpha_2\beta_1$ and $\alpha_V\beta_1$ integrins. Human MG63 osteosarcoma cells and normal rat kidney (NRK) cells contain $\alpha_V\beta_5$, $\alpha_2\beta_1$ and $\alpha_5\beta_1$ surface receptors. For comparison to osteoclasts, these cells are considered normal with respect to the expression of multiple integrins capable of attachment to more than one ligand. Because MG63 and NRK cells lack high expression of $\alpha_V\beta_3$, the activity of peptides on these cells reflects selectivity.

MG63 and NRK cell lines were purchased from ATTC (Rockville Md.). Cultures were maintained in DMEM containing 10% FCS. For attachment assays, cells were trypsinized, resuspended in serum-free DMEM and seeded in duplicate at $4\times10^4$ cells/well in 96 well microtiter plates that had been precoated with 10% FCS. Peptides were added and the cells were incubated for 1 hr at 37° C., 5% $CO_2$. Following incubation, cell layers were washed gently with warm DMEM, fixed in 10% formalin for 25 min, then stained with 0.1% crystal violet for 5 min. Following staining, the stain was extracted with 20% acetic acid and the $OD_{562}$ of the extracted stain was determined. The OD values obtained for wells containing peptide were compared to control wells, which represent maximum binding. The results of these experiments on NRK cells are shown in FIG. 8 and in FIG. 2 for both cell types.

Figure 8:
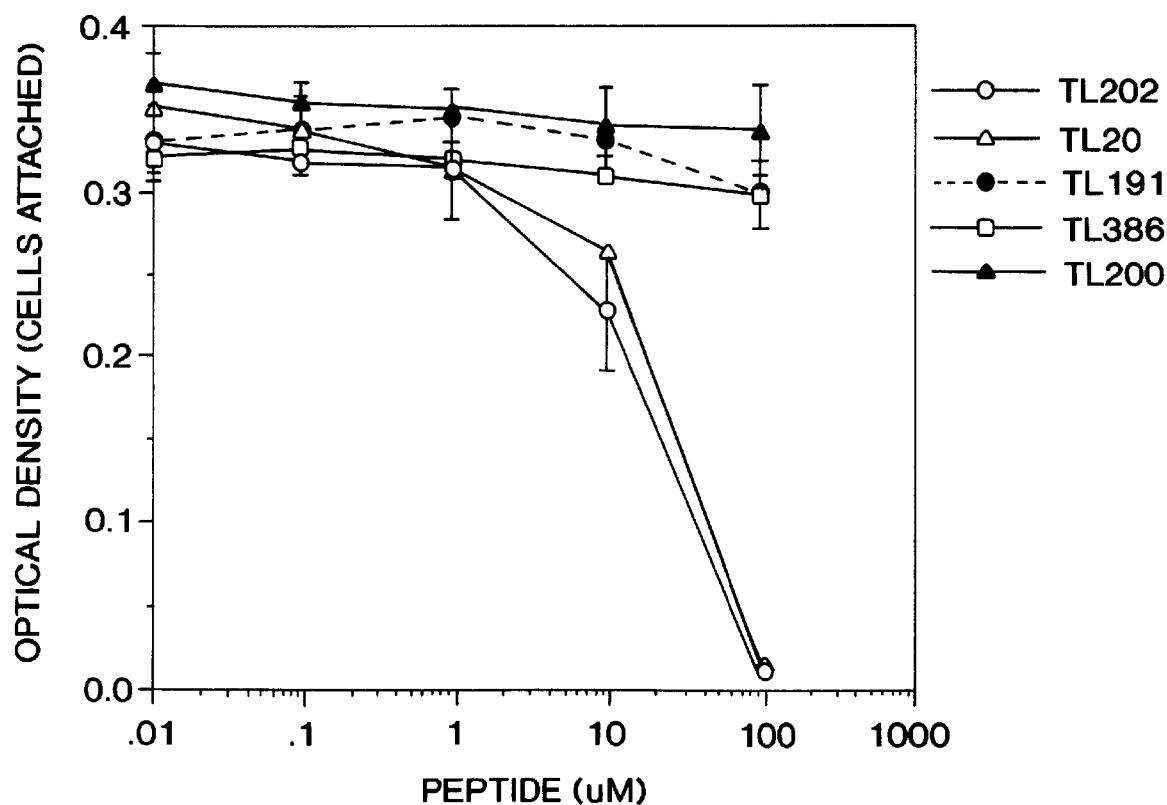
FIG. 8 demonstrates the selectivity of various peptides in the rat kidney cell attachment assay. Peptides that are selective for binding $\alpha_V\beta_3$ integrin, which is not present on normal rat kidney cells, do not affect attachment of the cells, whereas peptides that are nonselective for this integrin show a dose response for cell attachment.

Selectivity of a peptide can be determined by comparing the results of FIGS. 7 and 8 (see, also FIG. 2). Peptides that were highly active (low IC50) both on osteoclast attachment and on MG63 or NRK attachment are considered relatively nonselective. In contrast, peptides that were highly active on osteoclast attachment but were less active on MG63 or NRK attachment are considered selective (TL191, TL386 and TL159).

4. JY cell attachment assay

JY cells are human-derived B lymphocyte cells that express the $\alpha_V\beta_3$ VnR, which is the receptor that most likely is involved in osteoclast binding to bone (Stupack et al.,*Exp. Cell Res.* 203:443–448 (1992), which is incorporated herein by reference). JY cells do not express the $\alpha_V\beta_5$ VnR. RGD peptides were analyzed for their ability to inhibit the attachment of JY cells to vitronectin-coated plates.

Binding in the JY attachment assay is particularly relevant as a measure of the potency of a peptide, since JY cells are human cells and the $\alpha_V\beta_3$ VnR present on JY cells likely is the primary receptor involved in osteoclast attachment to bone. In chick osteoclasts, both $\alpha_V\beta_{3 and} \alpha_V\beta_5$ are expressed and likely involved in attachment. In addition, the JY attachment assay, when compared with the receptor-specific enzyme-linked immunosorbent assays (ELISAs) described below, demonstrates the selectivity of RGD peptides for inhibiting binding due to the $\alpha_V\beta_3$ VnR.

JY cells were grown in suspension in RPMI media (Irvine Scientific; Irvine, Calif.) supplemented with 10% heat inactivated fetal bovine serum (FBS) and 200 mM glutamine and containing 100 IU/ml penicillin and 100 $\mu$g/ml streptomycin. A 96 well ELISA plate (Linbro, Titertek) was coated with 100 $\mu$l/well of 5 $\mu$g/ml human Vn in sodium carbonate (pH 9.5) and incubated overnight at 4° C. The plate was rinsed 3× with PBS and blocked by adding 100 $\mu$l/well of 2 mg/ml BSA in PBS and incubating for 1 hr. Following blocking, the wells were washed 2× with PBS.

While the wells were being blocked, the JY cells were rinsed 2× with PBS, then resuspended to $10\times10^5$ cells/ml in serum-free RPMI containing 2 mg/ml BSA, 200 mM glutamine, 100 IU/ml penicillin, 100 $\mu$g/ml streptomycin and 0.5 mM $MnCl_2$. At this time, 50 ng/ml phorbol myristate acetate (PMA; Sigma) was added to the cell suspension. PMA stimulates the cells and allows them to bind Vn.

RGD peptides were diluted in the serum-free RPMI and 50 $\mu$l of each dilution was added to duplicate wells. 50 $\mu$l of the JY cell suspension was added to each well and the plate was incubated at 37° C. for 45 min, 7% $CO_2$. Nonadherent cells were gently aspirated from the wells and the wells were rinsed 1× with PBS. Cells were fixed in 10% formalin in PBS for 10 min, then stained with 0.1% toluidine blue for 1 hr. The plate was rinsed with distilled water and the cells were solubilized using 1% SDS. The amount of staining was determined by spectrophotometry at 595 nm and the IC50 was calculated as the concentration of an RGD peptide that inhibited JY cell binding to Vn by 50% (see FIG. 2, column designated "JY attach ($\alpha_V\beta_3$/Vn)").

5. Effect of RGD peptides on binding to $\alpha_V\beta_5$, $\alpha_5\beta_1$ and $\alpha_V\beta_3$ integrin receptors—ELISA Peptide binding to purified human $\alpha_V\beta_5$ and $\alpha_V\beta_3$, which are VnR's, and to $\alpha_5\beta_1$, which is a FnR, was determined using competitive ELISA assays as described below.

a. $\alpha_V\beta_5$ ELISA

For the $\alpha_V\beta_5$ assays, Vn was immobilized and the binding of solubilized $\alpha_V\beta_5$ in the presence of various concentrations of a peptide analogue was detected using a mouse monoclonal antibody to human $\alpha_V$ (clone VNR 147; Gibco; Gaithersburg, Md.). Binding of the antibody was visualized using a second antibody conjugated to horseradish peroxidase (BioRad; Richmond, Calif.).

Microtiter plates were coated at RT by adding 100 μl of 10 μg/ml human Vn in 0.05M sodium carbonate buffer (pH 9.6). The plates were incubated overnight at 4° C., then washed 3× with TBS containing 0.05% "TWEEN 20" polyoxyethylenesorbitan monolaurate (TBS/"TWEEN-20"). RGD peptides were diluted in TBS containing 20 mM OG, 2 mM $CaCl_2$ and 2 mM $MgCl_2$ and 50 μl was added to each well at 10-fold serial dilutions. Human $\alpha_V\beta_5$ was diluted in the same buffer and 50 μl was added to each well. Similar results were observed when the receptor was added prior to addition of the peptide.

The plates were incubated for 3 hr at RT, then washed with 300 μl TBS/"TWEEN-20" buffer. Bound receptor was incubated with 100 μl of the monoclonal anti-$\alpha_V$ antibody (diluted in TBS/"TWEEN-20") for 2 hr, then the wells were washed three times with TBS/"TWEEN-20". 100 μl of a 1:3000 dilution of affinity purified goat anti-mouse IgG conjugated to horseradish peroxidase was added to each well and the plates were incubated overnight at 4° C. Following incubation, the plates were washed 3× with TBS/TWEEN-20" and 100 μl of the substrate mixture (10 mg O-phenylenediamine in 25 ml 0.1M citrate phosphate buffer, pH 5.0, 6 μl 30% $H_2O_2$) was added to the wells. The reaction was allowed to develop for 10–15 min in the dark, then the development reaction was stopped by adding 50 μl of 4N $H_2SO_4$ to each well.

The amount of reaction product was quantitated by spectrophotometry at 490 nm. The IC50 was determined by computer using a Molecular Devices microplate reading spectrophotometer and "SOFTMAX 2.2" software using 4-parameter analysis. Nonspecific binding of antibody was measured in wells that did not contain receptor and this value was subtracted from total binding measured in wells containing receptor to yield the specific binding.

b. $\alpha_5\beta_1$ ELISA

Peptide binding to purified human $\alpha_5\beta_1$ (FnR) also was determined using a competitive ELISA. In these assays, Fn was immobilized to the wells and the binding of solubilized FnR in the presence of various concentrations of a peptide analogue was determined using a mouse monoclonal antibody to human $\beta_1$ (clone P4C10; Gibco) and specific binding was visualized using a second antibody.

Microtiter wells were coated at RT by adding 100 μl of 2 μg/ml human Fn in TBS and incubating the plates overnight at 4° C. Following incubation, the plates were washed 3× with TBS/"TWEEN-20". RGD peptides were diluted in TBS containing 20 mM OG and 2 mM $MnCl_2$ and 50 μl was added to wells at 10-fold serial dilutions. FnR was diluted in the same buffer and 50 μl was added to each well.

The plates were incubated for 3 hr at RT and washed with 300 μl TBS/"TWEEN-20". Bound receptor was incubated with 100 μl of the monoclonal anti-$\beta_1$ antibody for 2 hr, then washed 3× with TBS/"TWEEN-20". 100 μl of a 1:3000 fold dilution of affinity purified goat anti-mouse IgG conjugated to horseradish peroxidase was added to each well and incubated overnight at 4° C. The amount of bound second antibody was determined as described above.

c. $\alpha_V\beta_3$ ELISA

Peptide binding to purified $\alpha_V\beta_3$ receptor was determined by using a competitive ELISA, in which $\alpha_V\beta_3$ receptor was immobilized and the binding of solubilized VN, in the presence of various concentrations of peptide analogue, was detected using a monoclonal mouse IgG anti-VN antibody and a labelled anti-mouse IgG conjugate. A monoclonal anti-VN antibody can be obtained using routine methods (see, for example, Harlow and Lane, *Antibodies: A laboratory manual* (Cold Spring Harbor Laboratory Press 1988), which is incorporated herein by reference).

96 well microtiter plates were coated overnight at RT with 100 μl/well of $\alpha_V\beta_3$ receptor (0.5 μg/ml in 1×TBS, 4 mM octylglucoside, 1 mM $CaCl_2$). The wells were blocked with 200 μl/well of 1% BSA in 1×TBS, 1 mM $CaCl_2$ for at least 30 min. The plates were washed 2× with 1×TBS, 1 mM $CaCl_2$. 50 μl peptide in 1×TBS, 1 mM $CaCl_2$, 0.05% "TWEEN 20" polyoxyethylenesorbitan monolaurate was added in 10-fold serial dilutions. 50 μl of Vn in the same buffer then was added to each well.

The plates were incubated for 3 hr at RT, then washed 3× with 1×TBS, 0.05% "TWEEN 20" polyoxyethylenesorbitan monolaurate. 100 μof 8E6 (Telios) diluted to 1:6000 in 1×TBS, 0.05% "TWEEN 20" polyoxyethylenesorbitan monolaurate was added to the wells and the plates were incubated for 1 hr at RT. Plates were washed 3× with 1×TBS, 0.05% "TWEEN 20" polyoxyethylenesorbitan monolaurate. Affinity purified goat anti-mouse IgG conjugated to horseradish peroxidase (100μl/well; BioRad; Hercules Calif.) was added to each well and incubated for 1 hr at RT. Plates were washed 3× with 1×TBS, 0.05% "TWEEN 20" polyoxyethylenesorbitan monolaurate. 100 μl/well of substrate mixture (10 mg O-phenylenediamine in 25 ml 0.1M citrate-phosphate buffer, pH 5.0, 6 μl 30% $H_2O_2$) was added to the plates and allowed to develop. The development process was stopped by adding 50 μl to 4N $H_2SO_4$ to each well. The plates were read at 490 nm and the data analyzed by four parameter fit.

d. Analysis of ELISA results

The IC50 values for various RGD peptides were calculated by determining the concentration of a peptide that inhibited binding of Vn to $\alpha_V\beta_5$ or $\alpha_V\beta_3$ or of Fn to $\alpha_5\beta_1$ by 50%. The results of these assays are shown in FIG. 2 (columns designated "Receptor Assays").

Comparison of the IC50 values generated using the JY cell assay and the $\alpha_V\beta_3$ ELISA, which measure binding of the $\alpha_V\beta_3$ receptor involved in osteoclast binding to bone, with the $\alpha_V\beta_5$ and $\alpha_5\beta_1$ receptor-specific ELISAs, which represent receptors that likely are not involved in osteoclast attachment, provides insight into the receptor selectivity of the peptides. For example, a peptide such as peptide 368, which has an IC50 value for the $\alpha_V\beta_3$ ELISA or the $\alpha_V\beta_3$ VnR present on JY cells that is significantly lower than its IC50 value for the $\alpha_V\beta_5$ and $\alpha_5\beta_1$ receptors indicates that peptide 368 is a selective peptide.

In summary, the above series of assays are useful for determining the potency and selectivity of a peptide. Examples of particularly receptor selective peptides include 386, 814, 191, 228, 186, 368, 138, 448 and 159. Examples of particularly potent peptides include 373, 202, 196, 206, 197, 199, 183, 832, 812, 20, 437, 441, 429, 110, 214, 108 and 431. Examples of peptides that are both potent and selective include 386, 191, 814, 138, 368, 159 and 108.

EXAMPLE III

RGD Peptide Activity In Vivo

This example demonstrates that the RGD peptides of the invention can inhibit parathyroid hormone-induced hypercalcemia, which is a measure of osteoclast activation in a subject.

Parathyroid hormone (PTH) activates osteoclasts, which are involved in bone resorption. Associated with the increased osteoclast activity is an increase in serum calcium. The PTH-induced hypercalcemia assay measures the level of serum calcium, which is an indication of bone resorption in a subject (Fischer et al., *Endocrinology* 132:1411–1413 (1993), which is incorporated herein by reference).

Swiss-Webster mice, which had been parathyroidectomized two weeks prior to beginning the assay, were obtained from Taconic Lab Animals and Services (Germantown N.Y.). Femoral vein catheters (PE-50 fused with PE10 polyethylene tubing; Becton Dickinson; Parsippany, N.J.) were installed in the mice, flushed and locked with heparinized saline (1:10), sutured to adjacent muscle and internalized within the inguinal space of the incision before closing the incision with wound clips. Baseline serum ionized calcium levels were less than 1.29 mmol/l for mice selected for this study. Serum calcium measurements were performed by atomic absorption spectrophotometry using a Perkin-Elmer model 2380 AA spectrophotometer (Perkin-Elmer; Norwalk Conn.).

The experiment was initiated by feeding the mice a calcium-deficient diet overnight, then injecting the mice the following morning with a bolus of 0.2 mg PTH/kg (hPTH 1–34; Bachem; Torrance Calif.), intravenously. An ionized serum calcium level was obtained 30 min prior to PTH infusion. Various doses of a peptide or vehicle were infused into an animal for 4 hr, then ionized serum calcium again was measured. Lyophilized peptide was redissolved in PBS or in water, depending on the solubility at a particular concentration. Serum calcium measurements were expressed as the difference between the value 30 min before the PTH pulse and 4 hr after peptide infusion was started.

Figure 9:
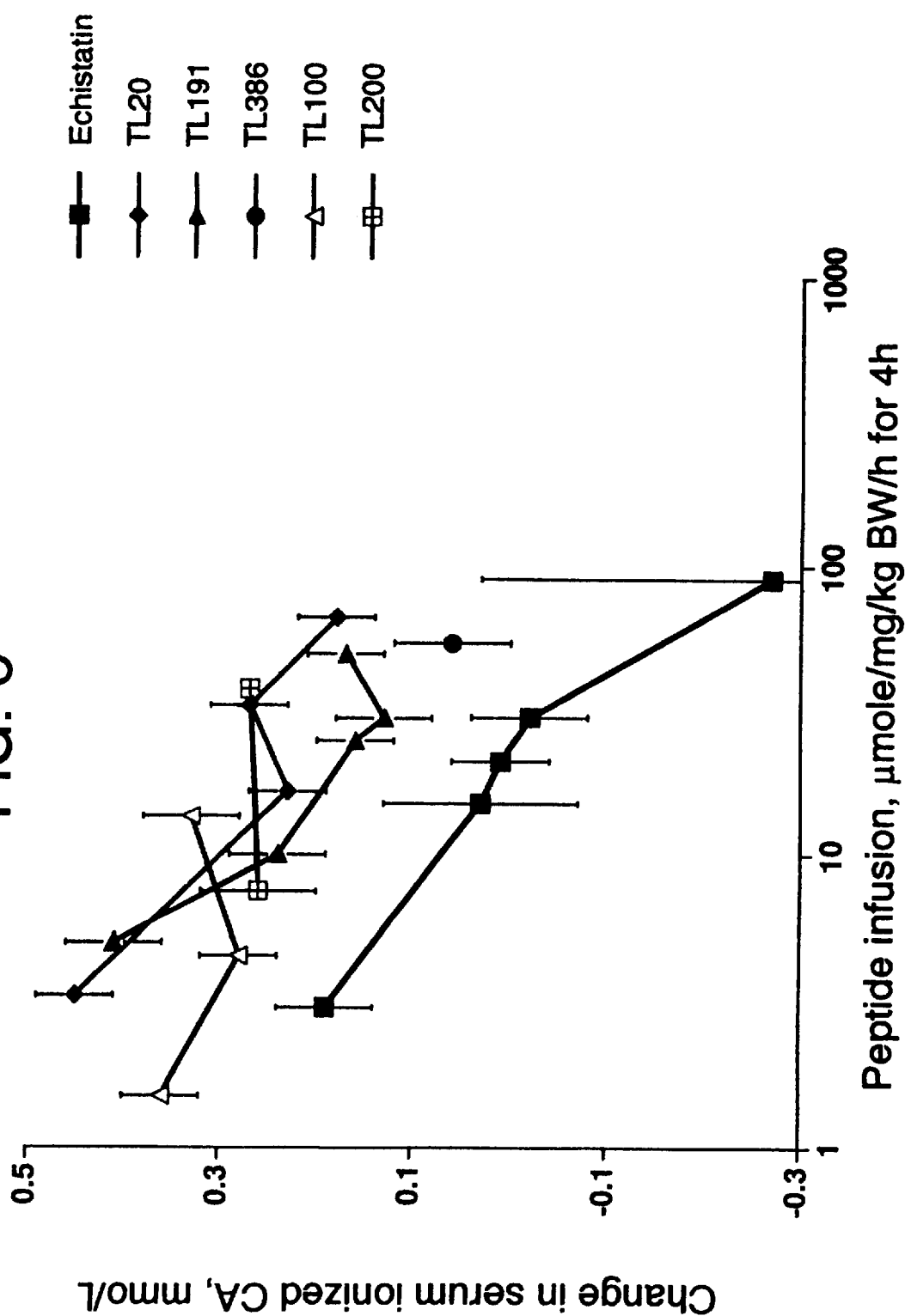
FIG. 9 shows the change in serum ionized calcium resulting from infusion of various peptides at the indicated concentrations.

One control peptide used for this experiment was echistatin (Bachem; Torrance Calif.), which was administered at doses ranging from 0–30 mg/kg/hr. Another control peptide as TL200, an RGD-containing peptide that is selective for the GPIIbIIIa integrin receptor present on platelets. The data presented in FIG. 9 demonstrate a dose responsive effect of the peptides. Peptides TL20 and TL191 decreased the PTH-induced rise in serum ionized calcium in a dose responsive manner. Peptide TL386 was analyzed at a single dose, which resulted in a relatively low level of serum calcium measured in animals within this group. The control peptide, TL200, did not show a dose responsive effect, confirming the selective nature of the TL20, TL191 and TL 386 peptides.

The ability of the peptides of the invention to reduce or inhibit bone resorption also is evaluated by determining the inhibition of bone loss in an ovariectomized rat, which is a model for estrogen deficiency-induced bone loss as occurs in post-menopausal women. The assay is performed as described by Kalu, *Bone Miner.* 15:175–192 (1991), which is incorporated herein by reference. In addition, useful animal model systems for evaluating the effectiveness of a peptide to reduce or inhibit bone resorption are described by Rogers et al., *Bone* 14:369–377 (1993), which is incorporated herein by reference.

In experiments using these model systems, a peptide is administered to an ovariectomized animal and bone loss is measured over a period of time such as over a five week period. A composition comprising the peptide can be administered in any of various ways such as intravenous, intraperitoneal, intramuscular or subcutaneous injection. In particular, a composition can be administered subcutaneously in the form of peptide-containing microcapsules.

The skilled artisan will understand that an effective peptide can be identified by administering various amounts of a peptide to groups of animals in order to obtain statistically significant results. For example, a range of peptide doses of about 1, 10 or 100 mg/kg/day can provide an indication of an effective amount of a peptide, which can reduce or inhibit bone resorption. One or more groups of animals can serve as appropriate controls.

Although the invention has been described with reference to the examples provided above, it should be understood that various modifications can be made without departing from the spirit of the invention. Accordingly, the invention is limited only by the claims.

We claim:

1. A method of reducing or inhibiting osteoclast binding to a matrix, comprising contacting the osteoclast in a subject needing reduction of bone resorption with an effective amount of a non-naturally occurring peptide having the structure:

$X_1$ $X_2$ $X_3$ $X_4$ GD $X_5$ $X_6$ $X_7$ $X_8$ (SEQ ID NO:25)

wherein:

$X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus;

$X_2$ is 0 or 1 amino acid;

$X_3$ is 0, 1 or 2 amino acids;

$X_4$ is a positively charged amino acid;

$X_5$ is an amino acid which can provide a hydrogen bond interaction with an integrin receptor;

$X_6$ is an amino acid that has the characteristics of hydrophobicity or conformational constraint;

$X_7$ is a residue forming a bond with a bridging amino acid of $X_2$, or with $X_3$ when $X_2$ is 0, or with $X_4$ when $X_2$ and $X_3$ are 0, to conformationally restrain the peptide; and $X_8$ is —$NR_3R_4$ (wherein $R_3$ is an H or alkyl group and $R_4$ is an H or alkyl group) or —$OR_5$ (wherein $R_5$ is an H or alkyl group) or 1 to 10 amino acids, which can be protected as an amide at the C-terminus, and wherein when $X_5$ is serine and $X_6$ is proline, $X_3$ is 0 or 2 amino acids.

2. The method of claim 1, wherein $X_2$ in said peptide is one amino acid.

3. The method of claim 1, wherein $X_3$ in said peptide consists of Phe-Ala, Ala-Ala, Glu-Ala, Tyr-Ala, Arg-Ala, Ile-Ala, Glu-Pro, Ile-Phe or (2-Nal)-Ala.

4. The method of claim 1, wherein $X_4$ in said peptide is Arg, Lys or homoArg.

5. The method of claim 1, wherein $X_5$ in said peptide is Asn, Ser or Thr.

6. The method of claim 5, wherein $X_4$ in said peptide is Arg and $X_6$ in said peptide is Tic.

7. The method of claim 1, wherein $X_6$ in said peptide is Tic, Pro, Phe or Ile.

8. The method of claim 1, wherein $X_4$ in said peptide is Arg and $X_6$ in said peptide is Tic.

9. A method for reducing or inhibiting osteoclast binding to a matrix, comprising contacting the osteoclast in a subject needing reduction of bone resorption with an effective amount of a non-naturally occurring peptide having the structure:

$X_1\ X_2\ X_3\ X_4\ GD\ X_5\ X_6\ X_7\ X_8$ (SEQ ID NO:26)

wherein:
- $X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus;
- $X_2$ is 0 or 1 amino acid;
- X3 is 0, 1 or 2 amino acids;
- X4 is a positively charged amino acid;
- $X_5$ is an amino acid that provides an ionic interaction with an integrin receptor;
- $X_6$ is Thr or is a hydrophobic amino acid;
- $X_7$ is a residue forming a bond with a bridging amino acid of $X_2$, or with $X_3$ when $X_2$ is 0, or with $X_4$ when $X_2$ and $X_3$ are 0, to conformationally restrain the peptide; and
- $X_8$ is —$NR_3R_4$ (wherein $R_3$ is an H or alkyl group and $R_4$ is an H or alkyl group) or —$OR_5$ (wherein $R_5$ is an H or alkyl group) or 1 to 10 amino acids, which can be protected as an amide at the C-terminus.

10. The method of claim 9, wherein $X_2$ in said peptide is one amino acid.

11. The method of claim 9, wherein $X_3$ in said peptide consists of Phe-Ala, Ala-Ala, Glu-Ala, Tyr-Ala, Arg-Ala, Ile-Ala, Glu-Pro, Ile-Phe or (2-Nal)-Ala.

12. The method of claim 9, wherein $X_4$ in said peptide is Arg, Lys or homoArg.

13. The method of claim 9, wherein $X_5$ in said peptide is Asp, Glu or β-[1(2)H-tetrazol-5-yl]-alanine.

14. The method of claim 9, wherein $X_6$ in said peptide is Leu, Ile, Val, Thr, nL, t-BuG, Cha or phenylglycine.

15. The method of claim 9, wherein $X_4$ in said peptide is Arg, $X_5$ is Asp and $X_6$ is Val.

16. A method of reducing or inhibiting bone resorption, comprising administering to a subject needing reduction of bone resorption a therapeutically effective amount of a non-naturally occurring peptide having the structure:

$X_1\ X_2\ X_3\ X_4\ GD\ X_5\ X_6\ X_7\ X_8$ (SEQ ID NO:25)

wherein
- $X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus;
- $X_2$ is 0 or 1 amino acid;
- $X_3$ is 0, 1 or 2 amino acids;
- $X_4$ is a positively charged amino acid;
- $X_5$ is an amino acid which can provide a hydrogen bond interaction with an integrin receptor;
- $X_6$ is an amino acid that has the characteristics of hydrophobicity or conformational constraint;
- $X_7$ is a residue forming a bond with a bridging amino acid of $X_2$, or with $X_3$ when $X_2$ is 0, or with $X_4$ when $X_2$ and $X_3$ are 0, to conformationally restrain the peptide; and
- $X_8$ is —$NR_3R_4$ (wherein $R_3$ is an H or alkyl group and $R_4$ is an H or alkyl group) or —$OR_5$ (wherein $R_5$ is an H or alkyl group) or 1 to 10 amino acids, which can be protected as an amide at the C-terminus, and wherein when $X_5$ is serine and $X_6$ is proline, $X_3$ is 0 or 2 amino acids.

17. The method of claim 16, wherein $X_2$ in said peptide is one amino acid.

18. The method of claim 16, wherein $X_3$ in said peptide consists of Phe-Ala, Ala-Ala, Glu-Ala, Tyr-Ala, Arg-Ala, Ile-Ala, Glu-Pro, Ile-Phe or (2-Nal)-Ala.

19. The method of claim 16, wherein $X_4$ in said peptide is Arg, Lys or homoArg.

20. The method of claim 16, wherein $X_5$ in said peptide is Asn, Ser or Thr.

21. The method of claim 20, wherein $X_4$ in said peptide is Arg and $X_6$ in said peptide is Tic.

22. The method of claim 16, wherein $X_6$ in said peptide is Tic, Pro, Phe or Ile.

23. The method of claim 16, wherein $X_4$ in said peptide is Arg and $X_6$ in said peptide is Tic.

24. A method for reducing or inhibiting bone resorption, comprising administering to a subject needing reduction of bone resorption a therapeutically effective amount of a non-naturally occurring peptide having the structure:

$X_1\ X_2\ X_3\ X_4\ GD\ X_5\ X_6\ X_7\ X_8$ (SEQ ID NO:26)

wherein:
- $X_1$ is $R_1R_2$ (wherein $R_1$ is an H or alkyl group and $R_2$ is an H, alkyl, $CH_3CO$, alkyl-CO or phenyl-CO group) or 1 to 10 amino acids, which can be protected by acetylation at the N-terminus;
- $X_2$ is 0 or 1 amino acid;
- $X_3$ is 0, 1 or 2 amino acids;
- $X_4$ is a positively charged amino acid;
- $X_5$ is an amino acid that provides an ionic interaction with an integrin receptor;
- $X_6$ is Thr or is a hydrophobic amino acid;
- $X_7$ is a residue forming a bond with a bridging amino acid of $X_2$, or with $X_3$ when $X_2$ is 0, or with $X_4$ when $X_2$ and $X_3$ are 0, to conformationally restrain the peptide; and
- $X_8$ is —$NR_3R_4$ (wherein $R_3$ is an H or alkyl group and $R_4$ is an H or alkyl group) or —$OR_5$ (wherein $R_5$ is an H or alkyl group) or 1 to 10 amino acids, which can be protected as an amide at the C-terminus.

25. The method of claim 24, wherein $X_2$ in said peptide is one amino acid.

26. The method of claim 24, wherein $X_3$ in said peptide consists of Phe-Ala, Ala-Ala, Glu-Ala, Tyr-Ala, Arg-Ala, Ile-Ala, Glu-Pro, Ile-Phe or (2-Nal)-Ala.

27. The method of claim 24, wherein $X_4$ in said peptide is Arg, Lys or homoArg.

28. The method of claim 24, wherein $X_5$ in said peptide is Asp, Glu or β-[1(2)H-tetrazol-5-yl]-alanine.

29. The method of claim 24, wherein $X_6$ in said peptide is Leu, Ile, Val, Thr, nL, t-BuG, Cha or phenylglycine.

30. The method of claim 24, wherein $X_4$ in said peptide is Arg, $X_5$ is Asp and $X_6$ is Val.

31. A peptide that can alter $\alpha_v\beta_3$ binding to a matrix, said peptide having the amino acid sequence:
Mpa-R-G-D-D-V-C-$NH_2$ (SEQ ID NO: 28);
G-R-G-D-D-V-D-$NH_2$ (SEQ ID NO: 7);

Ac-C-A-A-R-G-D-S-Tic-C-NH$_2$ (SEQ ID NO: 29);
R-G-D-D-V-E-NH$_2$ (SEQ ID NO: 3);
G-Pen-A-A-R-G-D-D-V-C-A-NH$_2$ (SEQ ID NO: 30):
Ac-C-R-G-D-N-P-Pen-NH$_2$ (SEQ ID NO: 31);
G-Pen-A-A-R-G-D-D-T-C-NH$_2$ (SEQ ID NO: 32);
G-Pen-R-A-R-G-D-D-V-C-A (SEQ ID NO: 33); or
G-Pen-I-A-R-G-D-D-L-C-A (SEQ ID NO: 34).

32. A peptide that can reduce or inhibit bone resorption in a subject, said peptide having the amino acid sequence:
Ac-C-A-A-R-G-D-N-Tic-C-NH$_2$ (SEQ ID NO: 35);
Ac-Pen-F-A-R-G-D-S-Tic-C-NH$_2$ (SEQ ID NO: 36);
Ac-C-R-G-D-T-Tic-C-NH$_2$ (SEQ ID NO: 37);
Ac-C-A-A-R-G-D-T-Tic-C-NH$_2$ (SEQ ID NO: 38);
Mpa-R-G-D-D-V-C-NH$_2$ (SEQ ID NO: 28);
R-G-D-D-V-E-NH$_2$ (SEQ ID NO: 3);
Ac-C-R-G-D-S-Tic-Pen-NH$_2$ (SEQ ID NO: 39);
Ac-Pen-F-A-R-G-D-D-PgL-C-NH$_2$ (SEQ ID NO: 40);
R-G-D-S-Tic-E-NH$_2$ (SEQ ID NO: 41);
Ac-C-A-A-R-G-D-S-Tic-C-NH$_2$ (SEQ ID NO: 29);
βAla-A-A-R-G-D-N-Tic-C-NH$_2$ (SEQ ID NO: 42);
G-C-E-P-R-G-D-N-Tic-C-A-NH$_2$ (SEQ ID NO: 43);
G-Pen-A-A-R-G-D-D-V-C-A-NH$_2$ (SEQ ID NO: 30);
G-Pen-R-A-R-G-D-D-V-C-A (SEQ ID NO: 33);
G-Pen-A-A-R-G-D-S-P-C-A (SEQ ID NO: 44);
Ac-Pen-F-A-R-G-D-N-Tic-C-NH$_2$ (SEQ ID NO: 45);
Ac-Pen-(YOMe)-A-R-G-D-N-Tic-C-NH$_2$ (SEQ ID NO: 46);
Ac-Pen-A-A-R-G-D-N-Tic-C-NH$_2$ (SEQ ID NO: 47);
Ac-C-R-G-D-S-Tic-C-NH$_2$ (SEQ ID NO: 48);
Ac-C-R-G-D-N-Tic-Pen-NH$_2$ (SEQ ID NO: 49);
Ac-C-R-G-D-S-Tic-C-A-K-NH$_2$ (SEQ ID NO: 50);
Ac-Pen-F-A-R-G-D-N-P-C-NH$_2$ (SEQ ID NO: 51); or
Ac-C-A-A-R-G-D-N-Tic-C-K-NH$_2$ (SEQ ID NO: 52).

33. A peptide that can reduce or inhibit osteoclast binding to a matrix, said peptide having the amino acid sequence:
Ac-C-A-A-R-G-D-N-Tic-C-NH$_2$ (SEQ ID NO: 35);
Ac-Pen-F-A-R-G-D-S-Tic-C-NH$_2$ (SEQ ID NO: 36);
Ac-C-R-G-D-T-Tic-C-NH$_2$ (SEQ ID NO: 37);
Ac-C-A-A-R-G-D-T-Tic-C-NH$_2$ (SEQ ID NO: 38);
Mpa-R-G-D-D-V-C-NH$_2$ (SEQ ID NO: 28);
R-G-D-D-V-E-NH$_2$ (SEQ ID NO: 3);
Ac-C-R-G-D-S-Tic-Pen-NH$_2$ (SEQ ID NO: 39);
Ac-Pen-F-A-R-G-D-D-PgL-C-NH$_2$ (SEQ ID NO: 40);
R-G-D-S-Tic-E-NH$_2$ (SEQ ID NO: 41);
Ac-C-A-A-R-G-D-S-Tic-C-NH$_2$ (SEQ ID NO: 29);
βAla-A-A-R-G-D-N-Tic-C-NH$_2$ (SEQ ID NO: 42);
G-C-E-P-R-G-D-N-Tic-C-A-NH$_2$ (SEQ ID NO: 43);
G-Pen-A-A-R-G-D-D-V-C-A-NH$_2$ (SEQ ID NO: 30);
G-Pen-R-A-R-G-D-D-V-C-A (SEQ ID NO: 33);
G-Pen-A-A-R-G-D-S-P-C-A (SEQ ID NO: 44);
Ac-Pen-F-A-R-G-D-N-Tic-C-NH$_2$ (SEQ ID NO: 45);
Ac-Pen-(YOMe)-A-R-G-D-N-Tic-C-NH$_2$ (SEQ ID NO: 46);
Ac-Pen-A-A-R-G-D-N-Tic-C-NH$_2$ (SEQ ID NO: 47);
Ac-C-R-G-D-S-Tic-C-NH$_2$ (SEQ ID NO: 48);
Ac-C-R-G-D-N-Tic-Pen-NH$_2$ (SEQ ID NO: 49);
Ac-C-R-G-D-S-Tic-C-A-K-NH$_2$ (SEQ ID NO: 50);
Ac-Pen-F-A-R-G-D-N-P-C-NH$_2$ (SEQ ID NO: 51); or
Ac-C-A-A-R-G-D-N-Tic-C-K-NH$_2$ (SEQ ID NO: 52).

34. A peptide having the amino acid sequence:
Mpa-R-G-D-D-V-C-NH$_2$ (SEQ ID NO: 28); or
Ac-Pen-(YOMe)-A-R-G-D-N-Tic-C-NH$_2$ (SEQ ID NO: 46).

35. A peptide that can alter $\alpha_v\beta_3$ binding to a matrix, said peptide having the amino acid sequence:

Mpa-R-G-D-D-(t-BuG)—C—NH$_2$ (SEQ ID NO: 53).

36. A peptide that can reduce or inhibit bone resorption in a subject, said peptide having the amino acid sequence:
G-A-A-R-G-D-S-Tic-E-NH$_2$ (SEQ ID NO: 54) or
Ac-C-E-P-R-G-D-N-Tic-C-NH$_2$ (SEQ ID NO: 55).

37. A peptide that can reduce or inhibit osteoclast binding to a matrix, said peptide having the amino acid sequence:
G-A-A-R-G-D-S-Tic-E-NH$_2$ (SEQ ID NO: 54) or
Ac-C-E-P-R-C-D-N-Tic-C-NH$_2$ (SEQ ID NO: 55).

38. A peptide having the amino acid sequence:
Mpa-R-G-D-D-(t-BuG)-C-NH$_2$ (SEQ ID NO: 53) or
Ac-C-E-P-R-G-D-N-Tic-C-NH$_2$ (SEQ ID NO: 55).

* * * * *

UNITED STATES PATENT AND TRADEMARK OFFICE
CERTIFICATE OF CORRECTION

PATENT NO. : 5,770,565
DATED : June 23, 1998
INVENTOR(S) : Cheng et al.

It is certified that error appears in the above-identified patent and that said Letters Patent is hereby corrected as shown below:

Column 6,
Line 63, please delete "CRGDS(Tic)Cs-" and replace with -- CRGDS(Tic)C- --.

Column 7,
Line 64, please delete "$\alpha_v\beta_1$" and replace with -- $\alpha_v\beta_3$ --.

Column 17,
Line 53, please delete "A, and B," and replace with -- $A_1$ and $B_1$ --.
Line 55, please delete "2 MM" and replace with -- 2 mM --.

Column 22,
Line 43, please delete "$\alpha_v\beta_3$ and $\alpha_v\beta_5$" and replace with -- $\alpha_v\beta_3$ and $\alpha_v\beta_5$ --.

Column 24,
Line 35, please delete "100 µof" and replace with -- 100 µl of --.

Column 101, claim 9,
Line 23, please delete "X3" and replace with -- $X_3$ --.
Line 24, please delete "X4" and replace with -- $X_4$ --.

Column 101, claim 14,
Line 46, please delete "phenyglycine." and replace with -- phenylglycine. --.

Column 102, claim 16,
Lines 5-6, please delete "$R_{5\ is\ an\ H\ or\ alkyl\ group)\ or}$" and replace with -- $R_5$ is an H or alkyl group) or --.

UNITED STATES PATENT AND TRADEMARK OFFICE
CERTIFICATE OF CORRECTION

PATENT NO. : 5,770,565
DATED : June 23, 1998
INVENTOR(S) : Cheng et al.

It is certified that error appears in the above-identified patent and that said Letters Patent is hereby corrected as shown below:

Column 104, claim 37,
Line 35, please delete "Ac-C-E-P-R-C-D-N-Tic –C-$NH_2$" and replace with
-- Ac-C-E-P-R-G-D-N-Tic-C-$NH_2$ --.

Signed and Sealed this

Nineteenth Day of February, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:1:

Arg  Gly  Asp  Asp  Val
    1                       5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:2:

Arg Gly Asp Asp Val Gly
    1                 5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:3:

Arg Gly Asp Asp Val Glu
    1                 5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO:4:

Gly Arg Gly Asp Ser Pro
    1                 5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:5:

Gly Arg Gly Asp Ser Pro Lys
    1                 5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:6:

Val Thr Arg Gly Asp Val Phe Thr Lys
1               5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Amino acid is amidated at the C- terminal."

(xi) SEQUENCE DESCRIPTION: SEQ ID NO:7:

Gly Arg Gly Asp Asp Val Asp
1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 7
        (D) OTHER INFORMATION: /note= "Amino acid is amidated at the C- terminal."

(xi) SEQUENCE DESCRIPTION: SEQ ID NO:8:

Phe Arg Gly Asp Thr Phe Glu
1               5

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:9:

Gly Arg Gly Asp Ser Pro Asp Gly
1               5

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:10:

Gly Arg Gly Asp Ser Pro Asp Phe
1               5

(2) INFORMATION FOR SEQ ID NO:11:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:11:

Phe Arg Gly Asp Ser Pro Glu Gly
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( D ) TOPOLOGY: circular ( i x ) FEATURE:
        ( A ) NAME/KEY: Peptide
        ( B ) LOCATION: 7
        ( D ) OTHER INFORMATION: /note= "Amino acid is amidated at the C- terminal."

( x i ) SEQUENCE DESCRIPTION: SEQ ID NO:12:

Gly Arg Gly Asp Thr Phe Glu
1                   5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:13:

Arg Gly Asp Ser Pro Glu
1              5

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 9
        ( D ) OTHER INFORMATION: /note= "Amino acid is amidated at the C- terminal."

( x i ) SEQUENCE DESCRIPTION: SEQ ID NO:14:

Gly Arg Ala Arg Gly Asp Asn Pro Glu
1                   5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:15:

Arg Gly Asp Thr Pro Glu
1              5

( 2 ) INFORMATION FOR SEQ ID NO:16:

(i) SEQUENCE CHARACTERISTICS:
    (A) LENGTH: 8 amino acids
    (B) TYPE: amino acid
    (D) TOPOLOGY: circular (xi) SEQUENCE DESCRIPTION: SEQ ID NO:16:

Gly Arg Gly Asp Glu Pro Asp Gly
1                   5

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
            the N- terminal."

(ix) FEATURE:
        (A) NAME/KEY: Peptide
        (B) LOCATION: 7
        (D) OTHER INFORMATION: /note= "Amino acid is amidated at
            the C- terminal."

(xi) SEQUENCE DESCRIPTION: SEQ ID NO:17:

Cys Arg Gly Asp Asp Val Cys
1                 5

(2) INFORMATION FOR SEQ ID NO:18:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
            the N- terminal."

(ix) FEATURE:
        (A) NAME/KEY: Peptide
        (B) LOCATION: 9
        (D) OTHER INFORMATION: /note= "Amino acid is amidated at
            the C- terminal."

(xi) SEQUENCE DESCRIPTION: SEQ ID NO:18:

Cys Ile Ala Arg Gly Asp Asp Val Cys
1                 5

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
            the N- terminal."

(ix) FEATURE:
        (A) NAME/KEY: Peptide
        (B) LOCATION: 9
        (D) OTHER INFORMATION: /note= "Amino acid is amidated at
            the C- terminal."

( x i ) SEQUENCE DESCRIPTION: SEQ ID NO:19:

Cys Glu Pro Arg Gly Asp Asp Val Cys
1               5

( 2 ) INFORMATION FOR SEQ ID NO:20:

( i ) SEQUENCE CHARACTERISTICS:
( A ) LENGTH: 9 amino acids
( B ) TYPE: amino acid
( D ) TOPOLOGY: circular ( i x ) FEATURE:
( A ) NAME/KEY: Peptide
( B ) LOCATION: 1
( D ) OTHER INFORMATION: /note= "Amino acid is acetylated at
the N- terminal."

( i x ) FEATURE:
( A ) NAME/KEY: Peptide
( B ) LOCATION: 9
( D ) OTHER INFORMATION: /note= "Amino acid is amidated at
the C- terminal."

( x i ) SEQUENCE DESCRIPTION: SEQ ID NO:20:

Cys Glu Ala Arg Gly Asp Asp Val Cys
1               5

( 2 ) INFORMATION FOR SEQ ID NO:21:

( i ) SEQUENCE CHARACTERISTICS:
( A ) LENGTH: 9 amino acids
( B ) TYPE: amino acid
( D ) TOPOLOGY: circular ( i x ) FEATURE:
( A ) NAME/KEY: Peptide
( B ) LOCATION: 1
( D ) OTHER INFORMATION: /note= "Amino acid is acetylated at
the N- terminal."

( i x ) FEATURE:
( A ) NAME/KEY: Peptide
( B ) LOCATION: 9
( D ) OTHER INFORMATION: /note= "Amino acid is amidated at
the C- terminal."

( x i ) SEQUENCE DESCRIPTION: SEQ ID NO:21:

Cys Ala Ala Arg Gly Asp Thr Pro Cys
1               5

( 2 ) INFORMATION FOR SEQ ID NO:22:

( i ) SEQUENCE CHARACTERISTICS:
( A ) LENGTH: 8 amino acids
( B ) TYPE: amino acid
( D ) TOPOLOGY: circular ( i x ) FEATURE:
( A ) NAME/KEY: Peptide
( B ) LOCATION: 1
( D ) OTHER INFORMATION: /note= "Amino acid is acetylated at
the N- terminal."

( i x ) FEATURE:
( A ) NAME/KEY: Peptide
( B ) LOCATION: 8
( D ) OTHER INFORMATION: /note= "Amino acid is amidated at
the C- terminal."

( x i ) SEQUENCE DESCRIPTION: SEQ ID NO:22:

Phe Cys Arg Gly Asp Thr Phe Cys
1               5

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:23:

Cys Ile Phe Arg Gly Asp Thr Phe Cys
1                       5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:24:

Arg Gly Asp Asn Ile Glu
1               5

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Xaa = R1R2N, (wherein R1 is
            an H or alkyl group and R2 is an H, alkyl, CH3CO,
            alkyl-CO or phenyl-CO group) or 1 to 10 amino acids,
            which can be protected by acetylation at the N-terminus."

( i x ) FEATURE:
        ( A ) NAME/KEY: Peptide
        ( B ) LOCATION: 2
        ( D ) OTHER INFORMATION: /note= "Xaa = 0 or 1 amino acid"

( i x ) FEATURE:
        ( A ) NAME/KEY: Peptide
        ( B ) LOCATION: 3
        ( D ) OTHER INFORMATION: /note= "Xaa = 0, 1 or 2 amino
            acids"

( i x ) FEATURE:
        ( A ) NAME/KEY: Peptide
        ( B ) LOCATION: 4
        ( D ) OTHER INFORMATION: /note= "Xaa = a positively charged
            amino acid"

( i x ) FEATURE:
        ( A ) NAME/KEY: Peptide
        ( B ) LOCATION: 7

(D) OTHER INFORMATION: /note= "Xaa = an amino acid which
can provide a hydrogen bond interaction with an
integrin receptor"

(ix) FEATURE:
(A) NAME/KEY: Peptide
(B) LOCATION: 8
(D) OTHER INFORMATION: /note= "Xaa = an amino acid that
has the characteristics of hydrophobicity or
conformational constraint"

(ix) FEATURE:
(A) NAME/KEY: Peptide
(B) LOCATION: 9
(D) OTHER INFORMATION: /note= "Xaa = a residue capable of
forming a bond with a bridging amino acid of Xaa at
position 2, or with Xaa at position 3 when Xaa at
position 2 is 0, or with Xaa at position 4 when Xaa
at position 2 and Xaa at position 3 are 0, to
conformationally restrain the peptide."

(ix) FEATURE:
(A) NAME/KEY: Peptide
(B) LOCATION: 10
(D) OTHER INFORMATION: /note= "Xaa = -CONR3R4, (wherein R3
is an H or alkyl group and R4 is an H or alkyl
group) or - COOR5 (wherein R5 is an H or alkyl group)
or 1 to 10 amino acids, which can be protected as an
amide at the C-terminus, and wherein when Xaa at
position 7 is serine and Xaa at position 8 is proline,
Xaa at position 3 is 0 or 2 amino acids."

(xi) SEQUENCE DESCRIPTION: SEQ ID NO:25:

Xaa Xaa Xaa Xaa Gly Asp Xaa Xaa Xaa Xaa
1               5                   10

(2) INFORMATION FOR SEQ ID NO:26:

(i) SEQUENCE CHARACTERISTICS:
(A) LENGTH: 10 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Xaa = R1R2N, (wherein R1 is
an H or alkyl group and R2 is an H, alkyl, CH3CO,
alkyl-CO or phenyl-CO group) or 1 to 10 amino acids,
which can be protected by acetylation at the N-terminus."

(ix) FEATURE:
(A) NAME/KEY: Peptide
(B) LOCATION: 2
(D) OTHER INFORMATION: /note= "Xaa = 0 or 1 amino acid"

(ix) FEATURE:
(A) NAME/KEY: Peptide
(B) LOCATION: 3
(D) OTHER INFORMATION: /note= "Xaa = 0, 1 or 2 amino
acids"

(ix) FEATURE:
(A) NAME/KEY: Peptide
(B) LOCATION: 4
(D) OTHER INFORMATION: /note= "Xaa = a positively charged
amino acid"

(ix) FEATURE:
(A) NAME/KEY: Peptide
(B) LOCATION: 7
(D) OTHER INFORMATION: /note= "Xaa = an amino acid that
provides an ionic or similar interaction with an
integrin receptor"

(ix) FEATURE:
(A) NAME/KEY: Peptide
(B) LOCATION: 8

(D) OTHER INFORMATION: /note= "Xaa = an amino acid having an aliphatic side chain or is an aliphatic non-natural amino acid that is hydrophobic"

(ix) FEATURE:
 (A) NAME/KEY: Peptide
 (B) LOCATION: 9
 (D) OTHER INFORMATION: /note= "Xaa = a residue capable of forming a bond with a bridging amino acid of Xaa at position 2, or with Xaa at position 3 when Xaa at position 2 is 0, or with Xaa at position 4 when Xaa at position 2 and Xaa at position 3 are 0, to conformationally restrain the peptide."

(ix) FEATURE:
 (A) NAME/KEY: Peptide
 (B) LOCATION: 10
 (D) OTHER INFORMATION: /note= "Xaa = -CONR3R4, (wherein R3 is an H or alkyl group and R4 is an H or alkyl group) or - COOR5 (wherein R5 is an H or alkyl group) or 1 to 10 amino acids, which can be protected as an amide at the C-terminus."

(xi) SEQUENCE DESCRIPTION: SEQ ID NO:26:

Xaa Xaa Xaa Xaa Gly Asp Xaa Xaa Xaa Xaa
1      5         10

(2) INFORMATION FOR SEQ ID NO:27:

(i) SEQUENCE CHARACTERISTICS:
  (A) LENGTH: 7 amino acids
  (B) TYPE: amino acid
  (D) TOPOLOGY: circular (ix) FEATURE:
  (A) NAME/KEY: Peptide
  (B) LOCATION: 1
  (D) OTHER INFORMATION: /note= "Amino acid is acetylated at the N- terminal."

(ix) FEATURE:
  (A) NAME/KEY: Peptide
  (B) LOCATION: 7
  (D) OTHER INFORMATION: /note= "Amino acid is amidated at the C- terminal."

(xi) SEQUENCE DESCRIPTION: SEQ ID NO:27:

Cys Arg Gly Asp Ser Pro Cys
1     5

(2) INFORMATION FOR SEQ ID NO:28:

(i) SEQUENCE CHARACTERISTICS:
  (A) LENGTH: 7 amino acids
  (B) TYPE: amino acid
  (D) TOPOLOGY: circular (ix) FEATURE:
  (A) NAME/KEY: Peptide
  (B) LOCATION: 1
  (D) OTHER INFORMATION: /note= "Xaa is Mpa"

(ix) FEATURE:
  (A) NAME/KEY: Peptide
  (B) LOCATION: 7
  (D) OTHER INFORMATION: /note= "Amino acid is amidated at the C- terminal."

(xi) SEQUENCE DESCRIPTION: SEQ ID NO:28:

Xaa Arg Gly Asp Asp Val Cys
1     5

(2) INFORMATION FOR SEQ ID NO:29:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at
        the N- terminal."

( i x ) FEATURE:
    ( A ) NAME/KEY: Peptide
    ( B ) LOCATION: 8
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at
        the C- terminal."

( x i ) SEQUENCE DESCRIPTION: SEQ ID NO:29:

Cys Ala Ala Arg Gly Asp Thr Xaa Cys
1               5

( 2 ) INFORMATION FOR SEQ ID NO:30:

( i ) SEQUENCE CHARACTERISTICS:
        ( A ) LENGTH: 11 amino acids
        ( B ) TYPE: amino acid
        ( D ) TOPOLOGY: circular ( i x ) FEATURE:
        ( A ) NAME/KEY: Peptide
        ( B ) LOCATION: 2
        ( D ) OTHER INFORMATION: /note= "Xaa is Pen"

( i x ) FEATURE:
        ( A ) NAME/KEY: Peptide
        ( B ) LOCATION: 11
        ( D ) OTHER INFORMATION: /note= "Amino acid is amidated at
            the C- terminal."

( x i ) SEQUENCE DESCRIPTION: SEQ ID NO:30:

Gly Xaa Ala Ala Arg Gly Asp Asp Val Cys Ala
1               5                   1 0

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 7
        ( D ) OTHER INFORMATION: /note= "Xaa is Pen"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:31:

Cys Arg Gly Asp Asn Pro Xaa
1               5

( 2 ) INFORMATION FOR SEQ ID NO:32:

( i ) SEQUENCE CHARACTERISTICS:
    ( A ) LENGTH: 10 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( i x ) FEATURE:
    ( A ) NAME/KEY: Peptide
    ( B ) LOCATION: 10
    ( D ) OTHER INFORMATION: /note= "Amino acid is amidated at
         the C- terminal."

( x i ) SEQUENCE DESCRIPTION: SEQ ID NO:32:

Gly  Xaa  Ala  Ala  Arg  Gly  Asp  Asp  Thr  Cys
  1                   5                        10

( 2 ) INFORMATION FOR SEQ ID NO:33:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:33:

Gly  Xaa  Arg  Ala  Arg  Gly  Asp  Asp  Val  Cys  Ala
  1                   5                        10

( 2 ) INFORMATION FOR SEQ ID NO:34:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:34:

Gly  Xaa  Ile  Ala  Arg  Gly  Asp  Asp  Leu  Cys  Ala
  1                   5                        10

( 2 ) INFORMATION FOR SEQ ID NO:35:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at
         the N- terminal."

( i x ) FEATURE:
    ( A ) NAME/KEY: Peptide
    ( B ) LOCATION: 8
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:35:

Cys Ala Ala Arg Gly Asp Asn Xaa Cys
1                          5

( 2 ) INFORMATION FOR SEQ ID NO:36:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 1
    ( D ) OTHER INFORMATION: /note= "Xaa is Pen"

( i x ) FEATURE:
    ( A ) NAME/KEY: Peptide
    ( B ) LOCATION: 8
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:36:

Xaa Phe Ala Arg Gly Asp Ser Xaa Cys
1                          5

( 2 ) INFORMATION FOR SEQ ID NO:37:

( i ) SEQUENCE CHARACTERISTICS:
    ( A ) LENGTH: 7 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Xaa is Tic"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:37:

Cys Arg Gly Asp Thr Xaa Cys
1                        5

( 2 ) INFORMATION FOR SEQ ID NO:38:

( i ) SEQUENCE CHARACTERISTICS:

(A) LENGTH: 9 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 8
(D) OTHER INFORMATION: /note= "Xaa is Tic"

(ix) FEATURE:
(A) NAME/KEY: Peptide
(B) LOCATION: 9
(D) OTHER INFORMATION: /note= "Amino acid is amidated at the C- terminal."

(xi) SEQUENCE DESCRIPTION: SEQ ID NO:38:

Cys Ala Ala Arg Gly Asp Thr Xaa Cys
1               5

(2) INFORMATION FOR SEQ ID NO:39:

(i) SEQUENCE CHARACTERISTICS:
(A) LENGTH: 7 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 6
(D) OTHER INFORMATION: /note= "Xaa is Tic"

(ix) FEATURE:
(A) NAME/KEY: Peptide
(B) LOCATION: 7
(D) OTHER INFORMATION: /note= "Xaa is Pen"

(ix) FEATURE:
(A) NAME/KEY: Peptide
(B) LOCATION: 7
(D) OTHER INFORMATION: /note= "Amino acid is amidated at the C- terminal."

(xi) SEQUENCE DESCRIPTION: SEQ ID NO:39:

Cys Arg Gly Asp Ser Xaa Xaa
1               5

(2) INFORMATION FOR SEQ ID NO:40:

(i) SEQUENCE CHARACTERISTICS:
(A) LENGTH: 9 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 1
(D) OTHER INFORMATION: /note= "Xaa is Pen"

( i x ) FEATURE:
  ( A ) NAME/KEY: Peptide
  ( B ) LOCATION: 8
  ( D ) OTHER INFORMATION: /note= "Xaa is Pgl"

( i x ) FEATURE:
  ( A ) NAME/KEY: Peptide
  ( B ) LOCATION: 9
  ( D ) OTHER INFORMATION: /note= "Amino acid is amidated at the C- terminal."

( x i ) SEQUENCE DESCRIPTION: SEQ ID NO:40:

Xaa Phe Ala Arg Gly Asp Asp Xaa Cys
1               5

( 2 ) INFORMATION FOR SEQ ID NO:41:

( i ) SEQUENCE CHARACTERISTICS:
    ( A ) LENGTH: 6 amino acids
    ( B ) TYPE: amino acid
    ( D ) TOPOLOGY: circular ( i x ) FEATURE:
    ( A ) NAME/KEY: Peptide
    ( B ) LOCATION: 5
    ( D ) OTHER INFORMATION: /note= "Xaa is Tic"

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:41:

Arg Gly Asp Ser Xaa Glu
1               5

( 2 ) INFORMATION FOR SEQ ID NO:42:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Xaa is Beta-Ala"

( i x ) FEATURE:
    ( A ) NAME/KEY: Peptide
    ( B ) LOCATION: 8
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:42:

Xaa Ala Ala Arg Gly Asp Asn Xaa Cys
1               5

( 2 ) INFORMATION FOR SEQ ID NO:43:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 9

(D) OTHER INFORMATION: /note= "Xaa is Tic"

(ix) FEATURE:
    (A) NAME/KEY: Peptide
    (B) LOCATION: 11
    (D) OTHER INFORMATION: /note= "Amino acid is amidated at the C- terminal."

(xi) SEQUENCE DESCRIPTION: SEQ ID NO:43:

Gly Cys Glu Pro Arg Gly Asp Asn Xaa Cys Ala
1               5                   10

(2) INFORMATION FOR SEQ ID NO:44:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa is Pen"

(xi) SEQUENCE DESCRIPTION: SEQ ID NO:44:

Gly Xaa Ala Ala Arg Gly Asp Ser Pro Cys Ala
1               5                   10

(2) INFORMATION FOR SEQ ID NO:45:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 1
        (D) OTHER INFORMATION: /note= "Xaa is Pen"

(ix) FEATURE:
        (A) NAME/KEY: Peptide
        (B) LOCATION: 8
        (D) OTHER INFORMATION: /note= "Xaa is Tic"

(ix) FEATURE:
        (A) NAME/KEY: Peptide
        (B) LOCATION: 9
        (D) OTHER INFORMATION: /note= "Amino acid is amidated at the C- terminal."

(xi) SEQUENCE DESCRIPTION: SEQ ID NO:45:

Xaa Phe Ala Arg Gly Asp Asn Xaa Cys
1               5

(2) INFORMATION FOR SEQ ID NO:46:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at the N- terminal."

( i x ) FEATURE:
    ( A ) NAME/KEY: Peptide
    ( B ) LOCATION: 1
    ( D ) OTHER INFORMATION: /note= "Xaa is Pen"

( i x ) FEATURE:
    ( A ) NAME/KEY: Peptide
    ( B ) LOCATION: 2
    ( D ) OTHER INFORMATION: /note= "Xaa is (YOme)"

( i x ) FEATURE:
    ( A ) NAME/KEY: Peptide
    ( B ) LOCATION: 8
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:46:

Xaa Xaa Ala Arg Gly Asp Asn Xaa Cys
1               5

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 8
        ( D ) OTHER INFORMATION: /note= "Xaa is Tic"

( i x ) FEATURE:
        ( A ) NAME/KEY: Peptide
        ( B ) LOCATION: 9
        ( D ) OTHER INFORMATION: /note= "Amino acid is amidated at the C- terminal."

( x i ) SEQUENCE DESCRIPTION: SEQ ID NO:47:

Xaa Ala Ala Arg Gly Asp Asn Xaa Cys
1               5

( 2 ) INFORMATION FOR SEQ ID NO:48:

( i ) SEQUENCE CHARACTERISTICS:
        ( A ) LENGTH: 7 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Xaa is Tic"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:48:

Cys Arg Gly Asp Ser Xaa Cys
1                       5

( 2 ) INFORMATION FOR SEQ ID NO:49:

( i ) SEQUENCE CHARACTERISTICS:
    ( A ) LENGTH: 7 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Xaa is Tic"

( i x ) FEATURE:
    ( A ) NAME/KEY: Peptide
    ( B ) LOCATION: 7
    ( D ) OTHER INFORMATION: /note= "Xaa is Pen"

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:49:

Cys Arg Gly Asp Asn Xaa Xaa
1                       5

( 2 ) INFORMATION FOR SEQ ID NO:50:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Xaa is Tic"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:50:

Cys Arg Gly Asp Ser Xaa Cys Ala Lys
1                       5

( 2 ) INFORMATION FOR SEQ ID NO:51:

( i ) SEQUENCE CHARACTERISTICS:

(A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
             the N- terminal."

(ix) FEATURE:
        (A) NAME/KEY: Peptide
        (B) LOCATION: 1
        (D) OTHER INFORMATION: /note= "Xaa is Pen"

(ix) FEATURE:
        (A) NAME/KEY: Peptide
        (B) LOCATION: 9
        (D) OTHER INFORMATION: /note= "Amino acid is amidated at
             the C- terminal."

(xi) SEQUENCE DESCRIPTION: SEQ ID NO:51:

Xaa  Phe  Ala  Arg  Gly  Asp  Asn  Pro  Cys
   1                   5

(2) INFORMATION FOR SEQ ID NO:52:

(i) SEQUENCE CHARACTERISTICS:
        (A) LENGTH: 10 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
             the N- terminal."

(ix) FEATURE:
        (A) NAME/KEY: Peptide
        (B) LOCATION: 8
        (D) OTHER INFORMATION: /note= "Xaa is Tic"

(ix) FEATURE:
        (A) NAME/KEY: Peptide
        (B) LOCATION: 10
        (D) OTHER INFORMATION: /note= "Amino acid is amidated at
             the C- terminal."

(xi) SEQUENCE DESCRIPTION: SEQ ID NO:52:

Cys  Ala  Ala  Arg  Gly  Asp  Asn  Xaa  Cys  Lys
   1                   5                        10

(2) INFORMATION FOR SEQ ID NO:53:

(i) SEQUENCE CHARACTERISTICS:
        (A) LENGTH: 7 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa is Mpa"

(ix) FEATURE:
        (A) NAME/KEY: Peptide
        (B) LOCATION: 6
        (D) OTHER INFORMATION: /note= "Xaa is (t-BuG)"

(ix) FEATURE:
        (A) NAME/KEY: Peptide
        (B) LOCATION: 7
        (D) OTHER INFORMATION: /note= "Amino acid is amidated at
             the C- terminal."

( x i ) SEQUENCE DESCRIPTION: SEQ ID NO:53:

Xaa Arg Gly Asp Asp Xaa Cys
1               5

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 8
        ( D ) OTHER INFORMATION: /note= "Xaa is Tic"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:54:

Gly Ala Ala Arg Gly Asp Ser Xaa Glu
1               5

( 2 ) INFORMATION FOR SEQ ID NO:55:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 8
        ( D ) OTHER INFORMATION: /note= "Xaa is Tic"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:55:

Cys Glu Pro Arg Gly Asp Asn Xaa Cys
1               5

( 2 ) INFORMATION FOR SEQ ID NO:56:

( i ) SEQUENCE CHARACTERISTICS:
        ( A ) LENGTH: 5 amino acids
        ( B ) TYPE: amino acid
        ( D ) TOPOLOGY: linear ( i x ) FEATURE:
        ( A ) NAME/KEY: Peptide
        ( B ) LOCATION: 5
        ( D ) OTHER INFORMATION: /note= "Xaa is Tic"

( x i ) SEQUENCE DESCRIPTION: SEQ ID NO:56:

Arg Gly Asp Asn Xaa
1               5

( 2 ) INFORMATION FOR SEQ ID NO:57:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is Pmc"

( x i ) SEQUENCE DESCRIPTION: SEQ ID NO:57:

```
Gly  Xaa  Arg  Gly  Asp  Cys  Ala
1                   5
```

( 2 ) INFORMATION FOR SEQ ID NO:58:

( i ) SEQUENCE CHARACTERISTICS:
    ( A ) LENGTH: 10 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:58:

```
Gly  Xaa  Gly  Arg  Gly  Asp  Asn  Tyr  Cys  Ala
1                   5                        10
```

( 2 ) INFORMATION FOR SEQ ID NO:59:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:59:

```
Gly  Xaa  Gly  Glu  Arg  Gly  Asp  Asn  Tyr  Cys  Ala
1                   5                             10
```

( 2 ) INFORMATION FOR SEQ ID NO:60:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 11
    ( D ) OTHER INFORMATION: /note= "Amino acid is amidated at
        the C- terminal."

( x i ) SEQUENCE DESCRIPTION: SEQ ID NO:60:

```
Gly  Xaa  Ala  Ala  Arg  Gly  Asp  Val  Pro  Cys  Ala
1                   5                             10
```

( 2 ) INFORMATION FOR SEQ ID NO:61:

( i ) SEQUENCE CHARACTERISTICS:
    ( A ) LENGTH: 10 amino acids
    ( B ) TYPE: amino acid
    ( D ) TOPOLOGY: circular ( i x ) FEATURE:
    ( A ) NAME/KEY: Peptide (B) LOCATION: 2
(D) OTHER INFORMATION: /note= "Xaa is Pen"

(ix) FEATURE:
(A) NAME/KEY: Peptide
(B) LOCATION: 10
(D) OTHER INFORMATION: /note= "Amino acid is amidated at the C- terminal."

(xi) SEQUENCE DESCRIPTION: SEQ ID NO:61:

| Gly | Xaa | Glu | Leu | Arg | Gly | Asp | Gly | Trp | Cys |
|-----|-----|-----|-----|-----|-----|-----|-----|-----|-----|
| 1   |     |     |     | 5   |     |     |     |     | 10  |

(2) INFORMATION FOR SEQ ID NO:62:

(i) SEQUENCE CHARACTERISTICS:
(A) LENGTH: 10 amino acids
(B) TYPE: amino acid
(D) TOPOLOGY: circular (ix) FEATURE:
(A) NAME/KEY: Peptide
(B) LOCATION: 2
(D) OTHER INFORMATION: /note= "Xaa is Pen"

(ix) FEATURE:
(A) NAME/KEY: Peptide
(B) LOCATION: 10
(D) OTHER INFORMATION: /note= "Amino acid is amidated at the C- terminal."

(xi) SEQUENCE DESCRIPTION: SEQ ID NO:62:

| Gly | Xaa | Gly | Phe | Arg | Gly | Asp | Glu | Pro | Cys |
|-----|-----|-----|-----|-----|-----|-----|-----|-----|-----|
| 1   |     |     |     | 5   |     |     |     |     | 10  |

(2) INFORMATION FOR SEQ ID NO:63:

(i) SEQUENCE CHARACTERISTICS:
(A) LENGTH: 11 amino acids
(B) TYPE: amino acid
(D) TOPOLOGY: circular (ix) FEATURE:
(A) NAME/KEY: Peptide
(B) LOCATION: 2
(D) OTHER INFORMATION: /note= "Xaa is Pen"

(xi) SEQUENCE DESCRIPTION: SEQ ID NO:63:

| Lys | Xaa | Gly | Phe | Arg | Gly | Asp | Glu | Pro | Cys | Arg |
|-----|-----|-----|-----|-----|-----|-----|-----|-----|-----|-----|
| 1   |     |     |     | 5   |     |     |     |     | 10  |     |

(2) INFORMATION FOR SEQ ID NO:64:

(i) SEQUENCE CHARACTERISTICS:
(A) LENGTH: 11 amino acids
(B) TYPE: amino acid
(D) TOPOLOGY: circular (ix) FEATURE:
(A) NAME/KEY: Peptide
(B) LOCATION: 2
(D) OTHER INFORMATION: /note= "Xaa is Pen"

(xi) SEQUENCE DESCRIPTION: SEQ ID NO:64:

| Lys | Xaa | Gly | Phe | Arg | Gly | Asp | Asp | Pro | Cys | Arg |
|-----|-----|-----|-----|-----|-----|-----|-----|-----|-----|-----|
| 1   |     |     |     | 5   |     |     |     |     | 10  |     |

(2) INFORMATION FOR SEQ ID NO:65:

(i) SEQUENCE CHARACTERISTICS:
(A) LENGTH: 9 amino acids
(B) TYPE: amino acid (D) TOPOLOGY: circular (ix) FEATURE:
    (A) NAME/KEY: Peptide
    (B) LOCATION: 1
    (D) OTHER INFORMATION: /note= "Amino acid is acetylated at the N- terminal."

(ix) FEATURE:
    (A) NAME/KEY: Peptide
    (B) LOCATION: 1
    (D) OTHER INFORMATION: /note= "Xaa is Pen"

(ix) FEATURE:
    (A) NAME/KEY: Peptide
    (B) LOCATION: 7
    (D) OTHER INFORMATION: /note= "Xaa is Orn"

(ix) FEATURE:
    (A) NAME/KEY: Peptide
    (B) LOCATION: 9
    (D) OTHER INFORMATION: /note= "Amino acid is amidated at the C- terminal."

(xi) SEQUENCE DESCRIPTION: SEQ ID NO:65:

Xaa Ala Ala Arg Gly Asp Xaa Pro Cys
1                      5

(2) INFORMATION FOR SEQ ID NO:66:

(i) SEQUENCE CHARACTERISTICS:
        (A) LENGTH: 6 amino acids
        (B) TYPE: amino acid
        (D) TOPOLOGY: linear (ix) FEATURE:
    (A) NAME/KEY: Peptide
    (B) LOCATION: 4
    (D) OTHER INFORMATION: /note= "Xaa is (YOMe)"

(ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:66:

Arg Gly Asp Xaa Arg Glu
1               5

(2) INFORMATION FOR SEQ ID NO:67:

(i) SEQUENCE CHARACTERISTICS:
        (A) LENGTH: 11 amino acids
        (B) TYPE: amino acid
        (D) TOPOLOGY: circular (ix) FEATURE:
    (A) NAME/KEY: Peptide
    (B) LOCATION: 2
    (D) OTHER INFORMATION: /note= "Xaa is Pen"

(xi) SEQUENCE DESCRIPTION: SEQ ID NO:67:

Gly Xaa Arg Ala Arg Gly Asp Asp Leu Cys Ala
1              5                    10

(2) INFORMATION FOR SEQ ID NO:68:

(i) SEQUENCE CHARACTERISTICS:
        (A) LENGTH: 11 amino acids
        (B) TYPE: amino acid
        (D) TOPOLOGY: circular (ix) FEATURE:

(A) NAME/KEY: Peptide
(B) LOCATION: 2
(D) OTHER INFORMATION: /note= "Xaa is Pen"

(ix) FEATURE:
(A) NAME/KEY: Peptide
(B) LOCATION: 9
(D) OTHER INFORMATION: /note= "Xaa is nL"

(xi) SEQUENCE DESCRIPTION: SEQ ID NO:68:

Gly Xaa Arg Ala Arg Gly Asp Asp Xaa Cys Ala
1               5                   10

(2) INFORMATION FOR SEQ ID NO:69:

(i) SEQUENCE CHARACTERISTICS:
(A) LENGTH: 11 amino acids
(B) TYPE: amino acid
(D) TOPOLOGY: circular (ix) FEATURE:
(A) NAME/KEY: Peptide
(B) LOCATION: 2
(D) OTHER INFORMATION: /note= "Xaa is Pen"

(xi) SEQUENCE DESCRIPTION: SEQ ID NO:69:

Gly Xaa Ala Ala Arg Gly Asp Asp Ile Cys Ala
1               5                   10

(2) INFORMATION FOR SEQ ID NO:70:

(i) SEQUENCE CHARACTERISTICS:
(A) LENGTH: 9 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Xaa is Beta-Ala"

(ix) FEATURE:
(A) NAME/KEY: Peptide
(B) LOCATION: 9
(D) OTHER INFORMATION: /note= "Amino acid is amidated at
        the C- terminal."

(xi) SEQUENCE DESCRIPTION: SEQ ID NO:70:

Xaa Arg Ala Arg Gly Asp Asn Pro Asp
1               5

(2) INFORMATION FOR SEQ ID NO:71:

(i) SEQUENCE CHARACTERISTICS:
(A) LENGTH: 9 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at
        the N- terminal."

(ix) FEATURE:
(A) NAME/KEY: Peptide
(B) LOCATION: 1
(D) OTHER INFORMATION: /note= "Xaa is Pen"

(ix) FEATURE:
(A) NAME/KEY: Peptide
(B) LOCATION: 8
(D) OTHER INFORMATION: /note= "Xaa is Pgl"

( i x ) FEATURE:
  ( A ) NAME/KEY: Peptide
  ( B ) LOCATION: 9
  ( D ) OTHER INFORMATION: /note= "Amino acid is amidated at the C- terminal."

( x i ) SEQUENCE DESCRIPTION: SEQ ID NO:71:

Xaa Phe Ala Arg Gly Asp Asn Xaa Cys
1               5

( 2 ) INFORMATION FOR SEQ ID NO:72:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 1
    ( D ) OTHER INFORMATION: /note= "Xaa is Pen"

( i x ) FEATURE:
    ( A ) NAME/KEY: Peptide
    ( B ) LOCATION: 3
    ( D ) OTHER INFORMATION: /note= "Xaa is (p-Cl-F)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:72:

Xaa Ile Xaa Arg Gly Asp Thr Phe Cys
1               5

( 2 ) INFORMATION FOR SEQ ID NO:73:

( i ) SEQUENCE CHARACTERISTICS:
    ( A ) LENGTH: 10 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:73:

Gly Xaa Gly Arg Gly Asp Ser Pro Cys Ala
1               5                   10

( 2 ) INFORMATION FOR SEQ ID NO:74:

( i ) SEQUENCE CHARACTERISTICS:
    ( A ) LENGTH: 11 amino acids
    ( B ) TYPE: amino acid
    ( D ) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:74:

Gly Xaa Gly His Arg Gly Asp Ser Pro Cys Ala (2) INFORMATION FOR SEQ ID NO:75:

(i) SEQUENCE CHARACTERISTICS:
        (A) LENGTH: 11 amino acids
        (B) TYPE: amino acid
        (D) TOPOLOGY: circular (ix) FEATURE:
        (A) NAME/KEY: Peptide
        (B) LOCATION: 2
        (D) OTHER INFORMATION: /note= "Xaa is Pen"

(xi) SEQUENCE DESCRIPTION: SEQ ID NO:75:

Gly Xaa Arg Ala Arg Gly Asp Asn Pro Cys Ala
1               5                   10

(2) INFORMATION FOR SEQ ID NO:76:

(i) SEQUENCE CHARACTERISTICS:
        (A) LENGTH: 8 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa is Pmp"

(ix) FEATURE:
        (A) NAME/KEY: Peptide
        (B) LOCATION: 7
        (D) OTHER INFORMATION: /note= "Xaa is Pen"

(xi) SEQUENCE DESCRIPTION: SEQ ID NO:76:

Xaa Arg Gly Asp Ser Pro Xaa Gly
1               5

(2) INFORMATION FOR SEQ ID NO:77:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Amino acid is acetylated at
            the N- terminal."

(ix) FEATURE:
        (A) NAME/KEY: Peptide
        (B) LOCATION: 7
        (D) OTHER INFORMATION: /note= "Xaa is (YOMe)"

(ix) FEATURE:
        (A) NAME/KEY: Peptide
        (B) LOCATION: 9
        (D) OTHER INFORMATION: /note= "Amino acid is amidated at
            the C- terminal."

(xi) SEQUENCE DESCRIPTION: SEQ ID NO:77:

Cys Asn Pro Arg Gly Asp Xaa Arg Cys
1               5

(2) INFORMATION FOR SEQ ID NO:78:

(i) SEQUENCE CHARACTERISTICS:
        (A) LENGTH: 11 amino acids
        (B) TYPE: amino acid
        (D) TOPOLOGY: circular ( i x ) FEATURE:
    ( A ) NAME/KEY: Peptide
    ( B ) LOCATION: 2
    ( D ) OTHER INFORMATION: /note= "Xaa is Pen"

( x i ) SEQUENCE DESCRIPTION: SEQ ID NO:78:

Gly Xaa Ala Ala Arg Gly Asp Asn Pro Cys Ala
1               5                   10

( 2 ) INFORMATION FOR SEQ ID NO:79:

( i ) SEQUENCE CHARACTERISTICS:
        ( A ) LENGTH: 11 amino acids
        ( B ) TYPE: amino acid
        ( D ) TOPOLOGY: circular ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:79:

Gly Xaa Ile Phe Arg Gly Asp Thr Phe Cys Ala
1               5                   10

( 2 ) INFORMATION FOR SEQ ID NO:80:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 8
        ( D ) OTHER INFORMATION: /note= "Xaa is (dhP)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:80:

Xaa Ala Ala Arg Gly Asp Asn Xaa Cys
1               5

( 2 ) INFORMATION FOR SEQ ID NO:81:

( i ) SEQUENCE CHARACTERISTICS:
        ( A ) LENGTH: 11 amino acids
        ( B ) TYPE: amino acid
        ( D ) TOPOLOGY: circular ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:81:

Gly Xaa Arg Ala Arg Gly Asp Asp Val Cys Ala ( 2 ) INFORMATION FOR SEQ ID NO:82:

( i ) SEQUENCE CHARACTERISTICS:
        ( A ) LENGTH: 11 amino acids
        ( B ) TYPE: amino acid
        ( D ) TOPOLOGY: circular ( i x ) FEATURE:
        ( A ) NAME/KEY: Peptide
        ( B ) LOCATION: 2
        ( D ) OTHER INFORMATION: /note= "Xaa is Pen"

( x i ) SEQUENCE DESCRIPTION: SEQ ID NO:82:

Gly Xaa Glu Ala Arg Gly Asp Asn Pro Cys Ala
1               5                   10

( 2 ) INFORMATION FOR SEQ ID NO:83:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:83:

Xaa Ala Ala Arg Gly Asp Asn Ile Cys
1               5

( 2 ) INFORMATION FOR SEQ ID NO:84:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:84:

Xaa Thr Ala Arg Gly Asp Asn Pro Cys
1               5

( 2 ) INFORMATION FOR SEQ ID NO:85:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 8
        ( D ) OTHER INFORMATION: /note= "Xaa is (Tic)"

( i x ) FEATURE:
        ( A ) NAME/KEY: Peptide
        ( B ) LOCATION: 9
        ( D ) OTHER INFORMATION: /note= "Amino acid is amidated at the C- terminal."

( x i ) SEQUENCE DESCRIPTION: SEQ ID NO:85:

Cys Ala Ala Arg Gly Asp Tyr Xaa Cys
1                         5

( 2 ) INFORMATION FOR SEQ ID NO:86:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 9
        ( D ) OTHER INFORMATION: /note= "Amino acid is amidated at the C- terminal."

( x i ) SEQUENCE DESCRIPTION: SEQ ID NO:86:

Xaa Phe Ala Arg Gly Asp Ser Pro Cys
1                         5

( 2 ) INFORMATION FOR SEQ ID NO:87:

( i ) SEQUENCE CHARACTERISTICS:
        ( A ) LENGTH: 9 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:

( A ) NAME/KEY: Peptide
( B ) LOCATION: 2
( D ) OTHER INFORMATION: /note= "Xaa is (YOMe)"

( i x ) FEATURE:
( A ) NAME/KEY: Peptide
( B ) LOCATION: 9
( D ) OTHER INFORMATION: /note= "Amino acid is amidated at the C- terminal."

( x i ) SEQUENCE DESCRIPTION: SEQ ID NO:87:

Xaa Xaa Ala Arg Gly Asp Asn Pro Cys
1               5

( 2 ) INFORMATION FOR SEQ ID NO:88:

( i ) SEQUENCE CHARACTERISTICS:
( A ) LENGTH: 7 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note= "Xaa is (p-Cl-F)"

( i x ) FEATURE:
( A ) NAME/KEY: Peptide
( B ) LOCATION: 7
( D ) OTHER INFORMATION: /note= "Amino acid is amidated at the C- terminal."

( x i ) SEQUENCE DESCRIPTION: SEQ ID NO:88:

Xaa Arg Gly Asp Thr Pro Asp
1               5

( 2 ) INFORMATION FOR SEQ ID NO:89:

( i ) SEQUENCE CHARACTERISTICS:
( A ) LENGTH: 10 amino acids
( B ) TYPE: amino acid
( D ) TOPOLOGY: circular ( i x ) FEATURE:
( A ) NAME/KEY: Peptide
( B ) LOCATION: 2
( D ) OTHER INFORMATION: /note= "Xaa is Pen"

( i x ) FEATURE:
( A ) NAME/KEY: Peptide
( B ) LOCATION: 10
( D ) OTHER INFORMATION: /note= "Amino acid is amidated at the C- terminal."

( x i ) SEQUENCE DESCRIPTION: SEQ ID NO:89:

Gly Xaa Ala Ala Arg Gly Asp Glu Pro Cys
1               5                   10

( 2 ) INFORMATION FOR SEQ ID NO:90:

( i ) SEQUENCE CHARACTERISTICS:
( A ) LENGTH: 9 amino acids
( B ) TYPE: amino acid
( D ) TOPOLOGY: circular ( i x ) FEATURE:
( A ) NAME/KEY: Peptide
( B ) LOCATION: 1
( D ) OTHER INFORMATION: /note= "Xaa is Beta-Ala"

( i x ) FEATURE:
( A ) NAME/KEY: Peptide
( B ) LOCATION: 8
( D ) OTHER INFORMATION: /note= "Xaa is Tic"

( i x ) FEATURE:
     ( A ) NAME/KEY: Peptide
     ( B ) LOCATION: 9
     ( D ) OTHER INFORMATION: /note= "Amino acid is amidated at
          the C- terminal."

( x i ) SEQUENCE DESCRIPTION: SEQ ID NO:90:

Xaa  Ala  Ala  Arg  Gly  Asp  Asn  Xaa  Asp
1                  5

( 2 ) INFORMATION FOR SEQ ID NO:91:

( i ) SEQUENCE CHARACTERISTICS:
          ( A ) LENGTH: 9 amino acids
          ( B ) TYPE: amino acid
          ( D ) TOPOLOGY: circular ( i x ) FEATURE:
          ( A ) NAME/KEY: Peptide
          ( B ) LOCATION: 1
          ( D ) OTHER INFORMATION: /note= "Amino acid is acetylated at
               the N- terminal"

( i x ) FEATURE:
          ( A ) NAME/KEY: Peptide
          ( B ) LOCATION: 8
          ( D ) OTHER INFORMATION: /note= "Xaa is Tic"

( i x ) FEATURE:
          ( A ) NAME/KEY: Peptide
          ( B ) LOCATION: 9
          ( D ) OTHER INFORMATION: /note= "Amino acid is amidated at
               the C- terminal."

( x i ) SEQUENCE DESCRIPTION: SEQ ID NO:91:

Cys  Ala  Ala  Arg  Gly  Asp  Thr  Xaa  Cys
1                  5

( 2 ) INFORMATION FOR SEQ ID NO:92:

( i ) SEQUENCE CHARACTERISTICS:
          ( A ) LENGTH: 9 amino acids
          ( B ) TYPE: amino acid
          ( D ) TOPOLOGY: circular ( i x ) FEATURE:
          ( A ) NAME/KEY: Peptide
          ( B ) LOCATION: 1
          ( D ) OTHER INFORMATION: /note= "Amino acid is acetylated at
               the N- terminal."

( i x ) FEATURE:
          ( A ) NAME/KEY: Peptide
          ( B ) LOCATION: 2
          ( D ) OTHER INFORMATION: /note= "Xaa is Pen"

( i x ) FEATURE:
          ( A ) NAME/KEY: Peptide
          ( B ) LOCATION: 8
          ( D ) OTHER INFORMATION: /note= "Xaa is (1-Nal)"

( i x ) FEATURE:
          ( A ) NAME/KEY: Peptide
          ( B ) LOCATION: 9
          ( D ) OTHER INFORMATION: /note= "Amino acid is amidated at
               the C- terminal."

( x i ) SEQUENCE DESCRIPTION: SEQ ID NO:92:

Xaa  Ala  Ala  Arg  Gly  Asp  Asn  Xaa  Cys
1                  5

( 2 ) INFORMATION FOR SEQ ID NO:93:

```
        ( i ) SEQUENCE CHARACTERISTICS:
                ( A ) LENGTH: 9 amino acids
                ( B ) TYPE: amino acid
                ( D ) TOPOLOGY: circular ( i x ) FEATURE:
                ( A ) NAME/KEY: Peptide
                ( B ) LOCATION: 1
                ( D ) OTHER INFORMATION: /note= "Amino acid is acetylated at
                        the N- terminal."

( i x ) FEATURE:
                ( A ) NAME/KEY: Peptide
                ( B ) LOCATION: 8
                ( D ) OTHER INFORMATION: /note= "Xaa is (fp)"

( i x ) FEATURE:
                ( A ) NAME/KEY: Peptide
                ( B ) LOCATION: 9
                ( D ) OTHER INFORMATION: /note= "Amino acid is amidated at
                        the C- terminal."

( x i ) SEQUENCE DESCRIPTION: SEQ ID NO:93:

Cys  Ala  Ala  Arg  Gly  Asp  Asn  Xaa  Cys
    1                     5
```

( 2 ) INFORMATION FOR SEQ ID NO:94:

```
        ( i ) SEQUENCE CHARACTERISTICS:
                ( A ) LENGTH: 10 amino acids
                ( B ) TYPE: amino acid
                ( D ) TOPOLOGY: circular ( i x ) FEATURE:
                ( A ) NAME/KEY: Peptide
                ( B ) LOCATION: 2
                ( D ) OTHER INFORMATION: /note= "Xaa is Pen"

( i x ) FEATURE:
                ( A ) NAME/KEY: Peptide
                ( B ) LOCATION: 10
                ( D ) OTHER INFORMATION: /note= "Amino acid is amidated at
                        the C- terminal."

( x i ) SEQUENCE DESCRIPTION: SEQ ID NO:94:

Gly  Xaa  Gly  Phe  Arg  Gly  Asp  Ser  Pro  Cys
    1                     5                       10
```

( 2 ) INFORMATION FOR SEQ ID NO:95:

```
        ( i ) SEQUENCE CHARACTERISTICS:
                ( A ) LENGTH: 9 amino acids
                ( B ) TYPE: amino acid
                ( D ) TOPOLOGY: circular ( i x ) FEATURE:
                ( A ) NAME/KEY: Peptide
                ( B ) LOCATION: 1
                ( D ) OTHER INFORMATION: /note= "Amino acid is acetylated at
                        the N- terminal."

( i x ) FEATURE:
                ( A ) NAME/KEY: Peptide
                ( B ) LOCATION: 1
                ( D ) OTHER INFORMATION: /note= "Xaa is Pen"

( i x ) FEATURE:
                ( A ) NAME/KEY: Peptide
                ( B ) LOCATION: 9
                ( D ) OTHER INFORMATION: /note= "Amino acid is amidated at
                        the C- terminal."

( x i ) SEQUENCE DESCRIPTION: SEQ ID NO:95:

Xaa  Phe  Ala  Arg  Gly  Asp  Asp  Val  Cys
    1                     5
```

( 2 ) INFORMATION FOR SEQ ID NO:96:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 1
        ( D ) OTHER INFORMATION: /note= "Xaa is Pen"

( i x ) FEATURE:
        ( A ) NAME/KEY: Peptide
        ( B ) LOCATION: 2
        ( D ) OTHER INFORMATION: /note= "Xaa is (2-Nal)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:96:

```
Xaa  Xaa  Ala  Arg  Gly  Asp  Asn  Pro  Cys
 1                   5
```

( 2 ) INFORMATION FOR SEQ ID NO:97:

( i ) SEQUENCE CHARACTERISTICS:
        ( A ) LENGTH: 9 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 8
        ( D ) OTHER INFORMATION: /note= "Xaa is (7-OMeTic)"

( i x ) FEATURE:
        ( A ) NAME/KEY: Peptide
        ( B ) LOCATION: 9
        ( D ) OTHER INFORMATION: /note= "Amino acid is amidated at
            the C- terminal."

( x i ) SEQUENCE DESCRIPTION: SEQ ID NO:97:

```
Cys  Ala  Ala  Arg  Gly  Asp  Asn  Xaa  Cys
 1                   5
```

( 2 ) INFORMATION FOR SEQ ID NO:98:

( i ) SEQUENCE CHARACTERISTICS:
        ( A ) LENGTH: 8 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
  ( A ) NAME/KEY: Peptide
  ( B ) LOCATION: 8
  ( D ) OTHER INFORMATION: /note= "Xaa is (Pen)"

( i x ) FEATURE:
  ( A ) NAME/KEY: Peptide
  ( B ) LOCATION: 8
  ( D ) OTHER INFORMATION: /note= "Amino acid is amidated at the C- terminal."

( x i ) SEQUENCE DESCRIPTION: SEQ ID NO:98:

Ala Cys Arg Gly Asp Ser Pro Xaa
1               5

( 2 ) INFORMATION FOR SEQ ID NO:99:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 1
    ( D ) OTHER INFORMATION: /note= "Xaa is Pen"

( i x ) FEATURE:
    ( A ) NAME/KEY: Peptide
    ( B ) LOCATION: 3
    ( D ) OTHER INFORMATION: /note= "Xaa is (nMeF)"

( i x ) FEATURE:
    ( A ) NAME/KEY: Peptide
    ( B ) LOCATION: 9
    ( D ) OTHER INFORMATION: /note= "Amino acid is amidated at the C- terminal."

( x i ) SEQUENCE DESCRIPTION: SEQ ID NO:99:

Xaa Ile Xaa Arg Gly Asp Thr Phe Cys
1               5

( 2 ) INFORMATION FOR SEQ ID NO:100:

( i ) SEQUENCE CHARACTERISTICS:
    ( A ) LENGTH: 18 amino acids
    ( B ) TYPE: amino acid
    ( D ) TOPOLOGY: circular ( i x ) FEATURE:
    ( A ) NAME/KEY: Peptide
    ( B ) LOCATION: 17
    ( D ) OTHER INFORMATION: /note= "Xaa is (Tic)"

( i x ) FEATURE:
    ( A ) NAME/KEY: Peptide
    ( B ) LOCATION: 18
    ( D ) OTHER INFORMATION: /note= "Amino acid is amidated at the C- terminal."

( x i ) SEQUENCE DESCRIPTION: SEQ ID NO:100:

Thr Ala Pro Gly Lys His Pro Asn Arg Cys Ala Ala Arg Gly Asp Asn
1               5                   10                  15
Xaa Cys ( 2 ) INFORMATION FOR SEQ ID NO:101:

( i ) SEQUENCE CHARACTERISTICS:
  ( A ) LENGTH: 9 amino acids
  ( B ) TYPE: amino acid
  ( D ) TOPOLOGY: circular ( i x ) FEATURE:
  ( A ) NAME/KEY: Peptide
  ( B ) LOCATION: 1
  ( D ) OTHER INFORMATION: /note= "Amino acid is acetylated at
      the N- terminal."

( i x ) FEATURE:
  ( A ) NAME/KEY: Peptide
  ( B ) LOCATION: 1
  ( D ) OTHER INFORMATION: /note= "Xaa is Pen"

( i x ) FEATURE:
  ( A ) NAME/KEY: Peptide
  ( B ) LOCATION: 8
  ( D ) OTHER INFORMATION: /note= "Xaa is (Pgl)"

( i x ) FEATURE:
  ( A ) NAME/KEY: Peptide
  ( B ) LOCATION: 9
  ( D ) OTHER INFORMATION: /note= "Amino acid is amidated at
      the C- terminal."

( x i ) SEQUENCE DESCRIPTION: SEQ ID NO:101:

Xaa  Phe  Ala  Arg  Gly  Asp  Asp  Xaa  Cys
1                    5

( 2 ) INFORMATION FOR SEQ ID NO:102:

( i ) SEQUENCE CHARACTERISTICS:
    ( A ) LENGTH: 9 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Amino acid is acetylated at
        the N- terminal."

( i x ) FEATURE:
    ( A ) NAME/KEY: Peptide
    ( B ) LOCATION: 8
    ( D ) OTHER INFORMATION: /note= "Xaa is (Tic)"

( i x ) FEATURE:
    ( A ) NAME/KEY: Peptide
    ( B ) LOCATION: 9
    ( D ) OTHER INFORMATION: /note= "Amino acid is amidated at
        the C- terminal."

( x i ) SEQUENCE DESCRIPTION: SEQ ID NO:102:

Cys  Phe  Ala  Arg  Gly  Asp  Thr  Xaa  Cys
1                    5

( 2 ) INFORMATION FOR SEQ ID NO:103:

( i ) SEQUENCE CHARACTERISTICS:
    ( A ) LENGTH: 7 amino acids
    ( B ) TYPE: amino acid
    ( D ) TOPOLOGY: circular ( i x ) FEATURE:
    ( A ) NAME/KEY: Peptide
    ( B ) LOCATION: 1
    ( D ) OTHER INFORMATION: /note= "Xaa is (Mpa)"

( i x ) FEATURE:
    ( A ) NAME/KEY: Peptide
    ( B ) LOCATION: 6
    ( D ) OTHER INFORMATION: /note= "Xaa is (Cha)"

( i x ) FEATURE:
    ( A ) NAME/KEY: Peptide
    ( B ) LOCATION: 7
    ( D ) OTHER INFORMATION: /note= "Amino acid is amidated at
        the C- terminal."

( x i ) SEQUENCE DESCRIPTION: SEQ ID NO:103:

Xaa Arg Gly Asp Asp Xaa Cys
1               5

( 2 ) INFORMATION FOR SEQ ID NO:104:

( i ) SEQUENCE CHARACTERISTICS:
        ( A ) LENGTH: 6 amino acids
        ( B ) TYPE: amino acid
        ( D ) TOPOLOGY: circular ( i x ) FEATURE:
        ( A ) NAME/KEY: Peptide
        ( B ) LOCATION: 5
        ( D ) OTHER INFORMATION: /note= "Xaa is (Tic)"

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:104:

Arg Gly Asp Asn Xaa Glu
1               5

( 2 ) INFORMATION FOR SEQ ID NO:105:

( i ) SEQUENCE CHARACTERISTICS:
        ( A ) LENGTH: 11 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 8
        ( D ) OTHER INFORMATION: /note= "Xaa is (Tic)"

( i x ) FEATURE:
        ( A ) NAME/KEY: Peptide
        ( B ) LOCATION: 11
        ( D ) OTHER INFORMATION: /note= "Amino acid is amidated at
            the C- terminal."

( x i ) SEQUENCE DESCRIPTION: SEQ ID NO:105:

Cys Ala Ala Arg Gly Asp Asn Xaa Cys Ala Lys
1               5                   10

( 2 ) INFORMATION FOR SEQ ID NO:106:

( i ) SEQUENCE CHARACTERISTICS:
        ( A ) LENGTH: 7 amino acids
        ( B ) TYPE: amino acid
        ( D ) TOPOLOGY: circular ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:

(A) NAME/KEY: Peptide
(B) LOCATION: 6
(D) OTHER INFORMATION: /note= "Xaa is (Tca)"

(ix) FEATURE:
(A) NAME/KEY: Peptide
(B) LOCATION: 7
(D) OTHER INFORMATION: /note= "Amino acid is amidated at the C- terminal."

(xi) SEQUENCE DESCRIPTION: SEQ ID NO:106:

Cys Arg Gly Asp Thr Xaa Cys
1                   5

(2) INFORMATION FOR SEQ ID NO:107:

(i) SEQUENCE CHARACTERISTICS:
(A) LENGTH: 7 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 6
(D) OTHER INFORMATION: /note= "Xaa is (Olc)"

(ix) FEATURE:
(A) NAME/KEY: Peptide
(B) LOCATION: 7
(D) OTHER INFORMATION: /note= "Amino acid is amidated at the C- terminal."

(xi) SEQUENCE DESCRIPTION: SEQ ID NO:107:

Cys Arg Gly Asp Thr Xaa Cys
1                   5

(2) INFORMATION FOR SEQ ID NO:108:

(i) SEQUENCE CHARACTERISTICS:
(A) LENGTH: 9 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 1
(D) OTHER INFORMATION: /note= "Xaa is (Pen)"

(ix) FEATURE:
(A) NAME/KEY: Peptide
(B) LOCATION: 9
(D) OTHER INFORMATION: /note= "Amino acid is amidated at the C- terminal."

(xi) SEQUENCE DESCRIPTION: SEQ ID NO:108:

Xaa Glu Ala Arg Gly Asp Asp Val Cys
1                   5

(2) INFORMATION FOR SEQ ID NO:109:

(i) SEQUENCE CHARACTERISTICS:
(A) LENGTH: 9 amino acids (B) TYPE: amino acid
(D) TOPOLOGY: circular (ix) FEATURE:
(A) NAME/KEY: Peptide
(B) LOCATION: 1
(D) OTHER INFORMATION: /note= "Amino acid is acetylated at the N- terminal."

(ix) FEATURE:
(A) NAME/KEY: Peptide
(B) LOCATION: 1
(D) OTHER INFORMATION: /note= "Xaa is (Pen)"

(ix) FEATURE:
(A) NAME/KEY: Peptide
(B) LOCATION: 8
(D) OTHER INFORMATION: /note= "Xaa is (homoP)"

(ix) FEATURE:
(A) NAME/KEY: Peptide
(B) LOCATION: 9
(D) OTHER INFORMATION: /note= "Amino acid is amidated at the C- terminal."

(xi) SEQUENCE DESCRIPTION: SEQ ID NO:109:

Xaa Ala Ala Arg Gly Asp Asn Xaa Cys
1               5

(2) INFORMATION FOR SEQ ID NO:110:

(i) SEQUENCE CHARACTERISTICS:
(A) LENGTH: 5 amino acids
(B) TYPE: amino acid
(D) TOPOLOGY: circular (ix) FEATURE:
(A) NAME/KEY: Peptide
(B) LOCATION: 5
(D) OTHER INFORMATION: /note= "Xaa is (Adp)"

(ix) FEATURE:
(A) NAME/KEY: Peptide
(B) LOCATION: 5
(D) OTHER INFORMATION: /note= "Amino acid is amidated at the C- terminal."

(xi) SEQUENCE DESCRIPTION: SEQ ID NO:110:

Arg Gly Asp Ser Xaa
1               5

(2) INFORMATION FOR SEQ ID NO:111:

(i) SEQUENCE CHARACTERISTICS:
(A) LENGTH: 10 amino acids
(B) TYPE: amino acid
(D) TOPOLOGY: circular (ix) FEATURE:
(A) NAME/KEY: Peptide
(B) LOCATION: 1
(D) OTHER INFORMATION: /note= "Xaa is (Pmp)"

(ix) FEATURE:
(A) NAME/KEY: Peptide
(B) LOCATION: 9
(D) OTHER INFORMATION: /note= "Xaa is (Tic)"

(ix) FEATURE:
(A) NAME/KEY: Peptide
(B) LOCATION: 10
(D) OTHER INFORMATION: /note= "Amino acid is amidated at the C- terminal."

(xi) SEQUENCE DESCRIPTION: SEQ ID NO:111:

-continued

```
Xaa  Ala  Ala  Arg  Gly  Asp  Asp  Asn  Xaa  Cys
 1                  5                       10
```

(2) INFORMATION FOR SEQ ID NO:112:

(i) SEQUENCE CHARACTERISTICS:
      (A) LENGTH: 8 amino acids
      (B) TYPE: amino acid
      (D) TOPOLOGY: circular (ix) FEATURE:
      (A) NAME/KEY: Peptide
      (B) LOCATION: 8
      (D) OTHER INFORMATION: /note= "Xaa is (Adp)"

(ix) FEATURE:
      (A) NAME/KEY: Peptide
      (B) LOCATION: 8
      (D) OTHER INFORMATION: /note= "Amino acid is amidated at the C- terminal."

(xi) SEQUENCE DESCRIPTION: SEQ ID NO:112:

```
Ala  Ala  Arg  Gly  Asp  Asp  Val  Xaa
 1              5
```

(2) INFORMATION FOR SEQ ID NO:113:

(i) SEQUENCE CHARACTERISTICS:
      (A) LENGTH: 9 amino acids
      (B) TYPE: amino acid
      (D) TOPOLOGY: circular (ix) FEATURE:
      (A) NAME/KEY: Peptide
      (B) LOCATION: 1
      (D) OTHER INFORMATION: /note= "Amino acid is acetylated at the N- terminal."

(ix) FEATURE:
      (A) NAME/KEY: Peptide
      (B) LOCATION: 1
      (D) OTHER INFORMATION: /note= "Xaa is (Pen)"

(ix) FEATURE:
      (A) NAME/KEY: Peptide
      (B) LOCATION: 9
      (D) OTHER INFORMATION: /note= "Amino acid is amidated at the C- terminal."

(xi) SEQUENCE DESCRIPTION: SEQ ID NO:113:

```
Xaa  Glu  Pro  Arg  Gly  Asp  Asp  Val  Cys
 1              5
```